United States Patent
Hasuoka et al.

(10) Patent No.: US 8,013,008 B2
(45) Date of Patent: Sep. 6, 2011

(54) CYCLIC AMINE COMPOUND

(75) Inventors: Atsushi Hasuoka, Ibaraki (JP); Satoshi Yamamoto, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 71 days.

(21) Appl. No.: 12/516,733

(22) PCT Filed: Nov. 29, 2007

(86) PCT No.: PCT/JP2007/073057
§ 371 (c)(1),
(2), (4) Date: May 28, 2009

(87) PCT Pub. No.: WO2008/066117
PCT Pub. Date: Jun. 5, 2008

(65) Prior Publication Data
US 2010/0087506 A1    Apr. 8, 2010

(30) Foreign Application Priority Data

Nov. 30, 2006  (JP) ................................. 2006-324538
Aug. 7, 2007   (JP) ................................. 2007-205966

(51) Int. Cl.
*A61K 31/402* (2006.01)
*C07D 207/12* (2006.01)
(52) U.S. Cl. ...................................... 514/424; 548/541
(58) Field of Classification Search ................. 514/424; 548/543
See application file for complete search history.

(56) References Cited

U.S. PATENT DOCUMENTS
2004/0083559 A1    5/2004   Sabelle et al.

FOREIGN PATENT DOCUMENTS
| | | |
|---|---|---|
| JP | 2002-088073 | 3/2002 |
| JP | 2003/252854 | 9/2003 |
| WO | 2004/016576 | 2/2004 |
| WO | 2005/090282 | 9/2005 |
| WO | 2005/108351 | 11/2005 |
| WO | 2005/115361 | 12/2005 |
| WO | 2006/076317 | 7/2006 |
| WO | 2006/124447 | 11/2006 |
| WO | WO-2006/117677 A1 | 11/2006 |
| WO | 2007/015567 | 2/2007 |
| WO | 2007/097289 | 8/2007 |

OTHER PUBLICATIONS

Wolff et al., Burger's Medicinal Chemistry and Drug Discovery, 1994, Wiley-Interscience, Fifth Edition, vol. I: Principles and Practice, pp. 975-977.*
Extended/Supplementary European Search Report for corresponding EP07832772 application (mailed Mar. 7, 2007).

* cited by examiner

*Primary Examiner* — Golam M M Shameem
*Assistant Examiner* — Kristin Bianchi
(74) *Attorney, Agent, or Firm* — Edwards Angell Palmer & Dodge LLP; Kongsik Kim

(57) ABSTRACT

A compound represented by the formula (I)

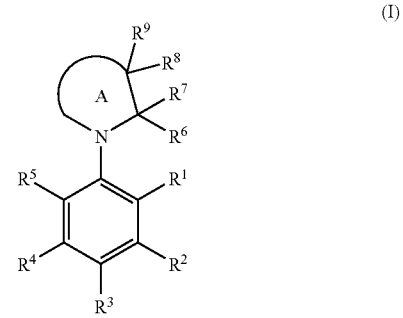

each symbol of which is defined in the specification, or a salt thereof which has a superior androgen receptor regulating activity.

8 Claims, No Drawings

CYCLIC AMINE COMPOUND

CROSS-REFERENCES TO RELATED APPLICATIONS

This application is a U.S. national phase application, pursuant to 35 U.S.C. §371, of PCT/JP2007/073057, filed Nov. 29, 2007, designating the United States, which claims priority to Japanese Application No. 2006-324538, filed Nov. 30, 2006, and Japanese Application No. 2007-205966, filed Aug. 7, 2007. The entire contents of the aforementioned patent applications are incorporated herein by this reference.

TECHNICAL FIELD

The present invention relates to a cyclic amine compound useful as an androgen receptor modulator and the like.

BACKGROUND OF THE INVENTION

Androgen is synthesized in the testis and adrenal cortex, bound to an androgen receptor in a target organ, and shows various physiological activities. Chemically, any natural androgen belongs to C19 steroid. The major androgen is testosterone mainly synthesized in the testis, which shows strong uptake in a target cell and strong physiological activity. In female, adrenal cortex is a major androgen supply source.

Androgen is involved in the growth and function maintenance of genital organ (prostate, vesicular gland, epididymis, vas deferens and the like), sex differentiation in the embryonic stage, spermatozoon formation, expression of secondary sexual characteristics (induction of masculinization in, for example, muscle-skeleton, voice, fat distribution etc., and the like), promotion of protein elaboration in muscle and the like, bone metabolism and the like. Therefore, shortage of androgen due to testis dysfunction, castration and the like results in insufficient actions mentioned above, thus leading to various diseases and degraded QOL (quality of life). To deal with the situation, a treatment method to supplement androgen is generally employed. Besides testosterone, synthetic androgen showing different balance of androgen action has been studied and put to practical use in clinical situations.

On the other hand, when androgen is involved in the progression of pathology, a treatment to decrease androgen is employed. For example, in androgen-dependent prostate cancer, castration and administration of GnRH agonist decrease testosterone and increase a treatment effect.

For supplementing androgen, testosterone and synthetic androgen are generally used. However, they have a steroid skeleton, which places much burden on the liver or shows other steroid hormone action. Therefore, an androgen receptor modulator (particularly agonist) having a non-steroidal skeleton is considered to be useful for the improvement of pathology caused by insufficient androgen action (hypogonadism, male climacteric disorder and the like) and pathology expected to show improvement by the action of androgen (osteoporosis and the like).

It is known that a naphthalene derivative having a pyrrolidine ring has a superior androgen receptor modulator action (patent reference 1). However, this reference does not disclose a pyrrolidinobenzene derivative having a substituent at the 3-position of pyrrolidine ring.

In addition, benzene derivatives having a pyrrolidine ring, which have an anti-androgen action (patent document 2 and 3), and a benzene derivatives having a pyrrolidine ring, which are used for osteoporosis and the like (patent document 4) are known. However, a compound having substituent(s) at the 3-position of pyrrolidine ring has not been disclosed.

patent document 1: WO2004/16576
patent document 2: JP-A-2002-88073
patent document 3: WO2005/090282
patent document 4: WO2005/108351

DISCLOSURE OF THE INVENTION

Problems to be Solved by the Invention

The present invention aims at providing a compound having a more superior androgen receptor regulating action.

Means of Solving the Problems

The present inventors have conducted intensive studies in view of the aforementioned problems and found that a cyclic aminobenzene compound represented by the formula (I) unexpectedly has a superior androgen receptor regulating action, which resulted in the completion of the present invention.

Accordingly, the present invention relates to
[1] a compound represented by the formula (I)

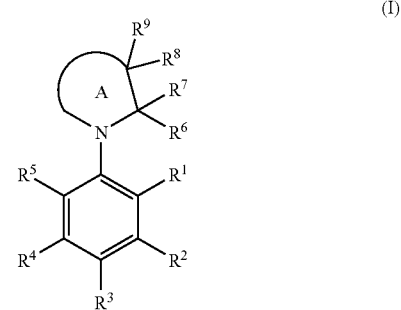

wherein
$R^1$ is a hydrogen atom, a halogen atom, a group via a carbon atom, a group via a nitrogen atom, a group via an oxygen atom or a group via a sulfur atom;
$R^2$ is a hydrogen atom, a halogen atom, a group via a carbon atom, a group via a nitrogen atom, a group via an oxygen atom or a group via a sulfur atom;
$R^3$ is an electron-withdrawing group;
$R^4$ is a hydrogen atom, a halogen atom, a group via a carbon atom, a group via a nitrogen atom, a group via an oxygen atom or a group via a sulfur atom;
$R^5$ is a hydrogen atom, a halogen atom, a group via a carbon atom, a group via a nitrogen atom, a group via an oxygen atom or a group via a sulfur atom;
$R^6$ is a hydrogen atom, a halogen atom, a group via a carbon atom, a group via a nitrogen atom, a group via an oxygen atom or a group via a sulfur atom;
$R^7$ is alkyl optionally having substituent(s);
$R^8$ is a hydrogen atom, alkyl optionally having substituent(s), alkenyl optionally having substituent(s) or cycloalkyl optionally having substituent(s);
$R^9$ is a group via an oxygen atom; and ring A is a 5- or 6-membered ring optionally having substituent(s) other than $R^6$ to $R^9$(except 2-chloro-4-[(2S,3S)-3-hydroxy-2-methylpyrrolidin-1-yl]-3-methylbenzonitrile, 2-chloro-4-[(2S,3S)-3-hydroxy-2-methylpyrrolidin-1-yl]benzonitrile, 4-[(2S,3S)-3-hydroxy-2-methylpyrrolidin-1-yl]

benzonitrile, 2-chloro-4-[(2S,3S)-3-hydroxy-2-methylpyrrolidin-1-yl]-5-methylbenzonitrile, 2-chloro-3-ethyl-4-[(2S,3S)-3-hydroxy-2-methylpyrrolidin-1-yl]benzonitrile, 4-[(2S,3S)-3-hydroxy-2-methylpyrrolidin-1-yl]-2-(trifluoromethyl)benzonitrile, 2,3-dichloro-4-[(2S,3S)-3-hydroxy-2-methylpyrrolidin-1-yl]-5-methylbenzonitrile, 2,3-dichloro-4-[(2S,3S)-3-hydroxy-2-methylpyrrolidin-1-yl]benzonitrile, 4-[(2S,3S)-3-hydroxy-2-methylpyrrolidin-1-yl]-3-(trifluoromethyl)benzonitrile, 4-[(2S,3S)-3-hydroxy-2-isopropylpyrrolidin-1-yl]-2-(trifluoromethyl)benzonitrile, 4-[(2S,3R)-3-hydroxy-2-isopropylpyrrolidin-1-yl]-2-(trifluoromethyl)benzonitrile, and 2-chloro-4-[(2S)-3-hydroxy-2-methylpiperidin-1-yl]benzonitrile) (hereinafter to be abbreviated as compound (I)), or a salt thereof,

[2] the compound of the above-mentioned [1], wherein $R^1$ is a hydrogen atom or alkyl optionally having substituent(s);

$R^2$ is a hydrogen atom, a halogen atom, alkyl optionally having substituent(s) or alkoxy optionally having substituent(s);

$R^3$ is cyano;

$R^4$ is a hydrogen atom or a halogen atom;

$R^5$ is a hydrogen atom;

$R^6$ is a hydrogen atom;

$R^7$ is alkyl optionally having substituent(s);

$R^8$ is a hydrogen atom, alkyl optionally having substituent(s), alkenyl optionally having substituent(s) or cycloalkyl optionally having substituent(s);

$R^9$ is hydroxy; and ring A is a 5-membered ring optionally having $C_{1-6}$ alkyl(s) other than $R^6$ to $R^9$,

[3] the compound of claim 1, wherein $R^1$ is (i) a hydrogen atom or (ii) $C_{1-6}$ alkyl optionally having halogen atom(s);

$R^2$ is a hydrogen atom, a halogen atom, $C_{1-6}$ alkyl optionally having halogen atom(s) or $C_{1-6}$ alkoxy;

$R^3$ is cyano;

$R^4$ is a hydrogen atom or a halogen atom;

$R^5$ is a hydrogen atom;

$R^6$ is a hydrogen atom;

$R^7$ is $C_{1-6}$ alkyl;

$R^8$ is a hydrogen atom, $C_{1-6}$ alkyl optionally having halogen atom(s), $C_{2-6}$ alkenyl or $C_{3-8}$ cycloalkyl;

$R^9$ is hydroxy; and ring A is a pyrrolidine ring optionally having 1 or 2 $C_{1-6}$ alkyl(s) other than $R^6$ to $R^9$,

[4] a compound below or a salt thereof:

2-fluoro-4-[(2S,3S)-3-hydroxy-2,3-dimethylpyrrolidin-1-yl]benzonitrile, 2-fluoro-4-[(2S,3S)-3-hydroxy-2,3-dimethylpyrrolidin-1-yl]-3-methylbenzonitrile, 4-[(2S,3S)-3-ethyl-3-hydroxy-2-methylpyrrolidin-1-yl]-2,6-difluorobenzonitrile, 2-chloro-4-[(2S,3S)-3-hydroxy-2-methyl-3-(trifluoromethyl)pyrrolidin-1-yl]benzonitrile, 2,6-difluoro-4-[(2S,3S)-3-hydroxy-2-isopropyl-3-methylpyrrolidin-1-yl]benzonitrile, or 4-[(2S,3R)-3-cyclopropyl-3-hydroxy-2-methylpyrrolidin-1-yl]-2-fluorobenzonitrile,

[5] a prodrug of a compound represented by the formula (I)

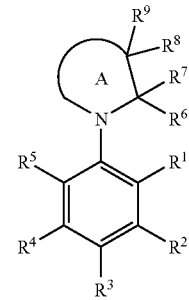

(I)

wherein $R^1$ is a hydrogen atom, a halogen atom, a group via a carbon atom, a group via a nitrogen atom, a group via an oxygen atom or a group via a sulfur atom;

$R^2$ is a hydrogen atom, a halogen atom, a group via a carbon atom, a group via a nitrogen atom, a group via an oxygen atom or a group via a sulfur atom;

$R^3$ is an electron-withdrawing group;

$R^4$ is a hydrogen atom, a halogen atom, a group via a carbon atom, a group via a nitrogen atom, a group via an oxygen atom or a group via a sulfur atom;

$R^5$ is a hydrogen atom, a halogen atom, a group via a carbon atom, a group via a nitrogen atom, a group via an oxygen atom or a group via a sulfur atom;

$R^6$ is a hydrogen atom, a halogen atom, a group via a carbon atom, a group via a nitrogen atom, a group via an oxygen atom or a group via a sulfur atom;

$R^7$ is alkyl optionally having substituent(s);

$R^8$ is a hydrogen atom, alkyl optionally having substituent(s), alkenyl optionally having substituent(s) or cycloalkyl optionally having substituent(s);

$R^9$ is a group via an oxygen atom; and ring A is a 5- or 6-membered ring optionally having substituent(s) other than $R^6$ to $R^9$(except 2-chloro-4-[(2S,3S)-3-hydroxy-2-methylpyrrolidin-1-yl]-3-methylbenzonitrile, 2-chloro-4-[(2S,3S)-3-hydroxy-2-methylpyrrolidin-1-yl]benzonitrile, 4-[(2S,3S)-3-hydroxy-2-methylpyrrolidin-1-yl]benzonitrile, 2-chloro-4-[(2S,3S)-3-hydroxy-2-methylpyrrolidin-1-yl]-5-methylbenzonitrile, 2-chloro-3-ethyl-4-[(2S,3S)-3-hydroxy-2-methylpyrrolidin-1-yl]benzonitrile, 4-[(2S,3S)-3-hydroxy-2-methylpyrrolidin-1-yl]-2-(trifluoromethyl)benzonitrile, 2,3-dichloro-4-[(2S,3S)-3-hydroxy-2-methylpyrrolidin-1-yl]-5-methylbenzonitrile, 2,3-dichloro-4-[(2S,3S)-3-hydroxy-2-methylpyrrolidin-1-yl]benzonitrile, 4-[(2S,3S)-3-hydroxy-2-methylpyrrolidin-1-yl]-3-(trifluoromethyl)benzonitrile, 4-[(2S,3S)-3-hydroxy-2-isopropylpyrrolidin-1-yl]-2-(trifluoromethyl)benzonitrile, 4-[(2S,3R)-3-hydroxy-2-isopropylpyrrolidin-1-yl]-2-(trifluoromethyl)benzonitrile, and 2-chloro-4-[(2S)-3-hydroxy-2-methylpiperidin-1-yl]benzonitrile),

[6] a medicament comprising a compound represented by the formula (I)

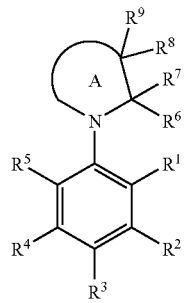

wherein
$R^1$ is a hydrogen atom, a halogen atom, a group via a carbon atom, a group via a nitrogen atom, a group via an oxygen atom or a group via a sulfur atom;
$R^2$ is a hydrogen atom, a halogen atom, a group via a carbon atom, a group via a nitrogen atom, a group via an oxygen atom or a group via a sulfur atom;
$R^3$ is an electron-withdrawing group;
$R^4$ is a hydrogen atom, a halogen atom, a group via a carbon atom, a group via a nitrogen atom, a group via an oxygen atom or a group via a sulfur atom;
$R^5$ is a hydrogen atom, a halogen atom, a group via a carbon atom, a group via a nitrogen atom, a group via an oxygen atom or a group via a sulfur atom;
$R^6$ is a hydrogen atom, a halogen atom, a group via a carbon atom, a group via a nitrogen atom, a group via an oxygen atom or a group via a sulfur atom;
$R^7$ is alkyl optionally having substituent(s);
$R^8$ is a hydrogen atom, alkyl optionally having substituent(s), alkenyl optionally having substituent(s) or cycloalkyl optionally having substituent(s);
$R^9$ is a group via an oxygen atom; and
ring A is a 5- or 6-membered ring optionally having substituent(s) other than $R^6$ to $R^9$ (except 2-chloro-4-[(2S,3S)-3-hydroxy-2-methylpyrrolidin-1-yl]-3-methylbenzonitrile, 2-chloro-4-[(2S,3S)-3-hydroxy-2-methylpyrrolidin-1-yl]benzonitrile, 4-[(2S,3S)-3-hydroxy-2-methylpyrrolidin-1-yl]benzonitrile, 2-chloro-4-[(2S,3S)-3-hydroxy-2-methylpyrrolidin-1-yl]-5-methylbenzonitrile, 2-chloro-3-ethyl-4-[(2S,3S)-3-hydroxy-2-methylpyrrolidin-1-yl]benzonitrile, 4-[(2S,3S)-3-hydroxy-2-methylpyrrolidin-1-yl]-2-(trifluoromethyl)benzonitrile, 2,3-dichloro-4-[(2S,3S)-3-hydroxy-2-methylpyrrolidin-1-yl]-5-methylbenzonitrile, 2,3-dichloro-4-[(2S,3S)-3-hydroxy-2-methylpyrrolidin-1-yl]benzonitrile, 4-[(2S,3S)-3-hydroxy-2-methylpyrrolidin-1-yl]-3-(trifluoromethyl)benzonitrile, 4-[(2S,3S)-3-hydroxy-2-isopropylpyrrolidin-1-yl]-2-(trifluoromethyl)benzonitrile, 4-[(2S,3R)-3-hydroxy-2-isopropylpyrrolidin-1-yl]-2-(trifluoromethyl)benzonitrile, and 2-chloro-4-[(2S)-3-hydroxy-2-methylpiperidin-1-yl]benzonitrile), or a salt thereof or a prodrug thereof,
[7] the medicament of the above-mentioned [6], which is an androgen receptor modulator,
[8] the medicament of the above-mentioned [6], which is an androgen receptor agonist,
[9] the medicament of the above-mentioned [6], which is an organ selective androgen receptor modulator,
[10] the medicament of the above-mentioned [6], which is an agent for the prophylaxis or treatment of hypogonadism, male climacteric disorder, frailty, cachexia or osteoporosis,
[11] the medicament of the above-mentioned [6], which is a frailty suppressive agent, a muscle enhancing agent, a muscle increasing agent, a cachexia suppressive agent, a body weight decrease suppressive agent, an agent for the prophylaxis or treatment of prostatomegaly, muscular atrophy disorder or muscle decrease caused by a disease, or a prostate weight decreasing agent,
[12] a method for the prophylaxis or treatment of hypogonadism, male climacteric disorder, frailty, cachexia or osteoporosis, comprising administering, to a mammal, an effective amount of a compound represented by the formula (I)

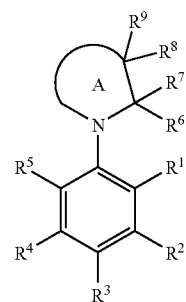

wherein
$R^1$ is a hydrogen atom, a halogen atom, a group via a carbon atom, a group via a nitrogen atom, a group via an oxygen atom or a group via a sulfur atom;
$R^2$ is a hydrogen atom, a halogen atom, a group via a carbon atom, a group via a nitrogen atom, a group via an oxygen atom or a group via a sulfur atom;
$R^3$ is an electron-withdrawing group;
$R^4$ is a hydrogen atom, a halogen atom, a group via a carbon atom, a group via a nitrogen atom, a group via an oxygen atom or a group via a sulfur atom;
$R^5$ is a hydrogen atom, a halogen atom, a group via a carbon atom, a group via a nitrogen atom, a group via an oxygen atom or a group via a sulfur atom;
$R^6$ is a hydrogen atom, a halogen atom, a group via a carbon atom, a group via a nitrogen atom, a group via an oxygen atom or a group via a sulfur atom;
$R^7$ is alkyl optionally having substituent(s);
$R^8$ is a hydrogen atom, alkyl optionally having substituent(s), alkenyl optionally having substituent(s) or cycloalkyl optionally having substituent(s);
$R^9$ is a group via an oxygen atom; and
ring A is a 5- or 6-membered ring optionally having substituent(s) other than $R^6$ to $R^9$ (except 2-chloro-4-[(2S,3S)-3-hydroxy-2-methylpyrrolidin-1-yl]-3-methylbenzonitrile, 2-chloro-4-[(2S,3S)-3-hydroxy-2-methylpyrrolidin-1-yl]benzonitrile, 4-[(2S,3S)-3-hydroxy-2-methylpyrrolidin-1-yl]benzonitrile, 2-chloro-4-[(2S,3S)-3-hydroxy-2-methylpyrrolidin-1-yl]-5-methylbenzonitrile, 2-chloro-3-ethyl-4-[(2S,3S)-3-hydroxy-2-methylpyrrolidin-1-yl]benzonitrile, 4-[(2S,3S)-3-hydroxy-2-methylpyrrolidin-1-yl]-2-(trifluoromethyl)benzonitrile, 2,3-dichloro-4-[(2S,3S)-3-hydroxy-2-methylpyrrolidin-1-yl]-5-methylbenzonitrile, 2,3-dichloro-4-[(2S,3S)-3-hydroxy-2-methylpyrrolidin-1-yl]benzonitrile, 4-[(2S,3S)-3-hydroxy-2-methylpyrrolidin-1-yl]-3-(trifluoromethyl)

benzonitrile, 4-[(2S,3S)-3-hydroxy-2-isopropylpyrrolidin-1-yl]-2-(trifluoromethyl)benzonitrile, 4-[(2S,3R)-3-hydroxy-2-isopropylpyrrolidin-1-yl]-2-(trifluoromethyl)benzonitrile, and 2-chloro-4-[(2S)-3-hydroxy-2-methylpiperidin-1-yl]benzonitrile), or a salt thereof or a prodrug thereof,

[13] use of a compound represented by the formula (I)

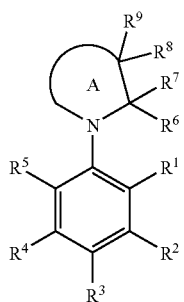

(I)

wherein
$R^1$ is a hydrogen atom, a halogen atom, a group via a carbon atom, a group via a nitrogen atom, a group via an oxygen atom or a group via a sulfur atom;
$R^2$ is a hydrogen atom, a halogen atom, a group via a carbon atom, a group via a nitrogen atom, a group via an oxygen atom or a group via a sulfur atom;
$R^3$ is an electron-withdrawing group;
$R^4$ is a hydrogen atom, a halogen atom, a group via a carbon atom, a group via a nitrogen atom, a group via an oxygen atom or a group via a sulfur atom;
$R^5$ is a hydrogen atom, a halogen atom, a group via a carbon atom, a group via a nitrogen atom, a group via an oxygen atom or a group via a sulfur atom;
$R^6$ is a hydrogen atom, a halogen atom, a group via a carbon atom, a group via a nitrogen atom, a group via an oxygen atom or a group via a sulfur atom;
$R^7$ is alkyl optionally having substituent(s);
$R^8$ is a hydrogen atom, alkyl optionally having substituent(s), alkenyl optionally having substituent(s) or cycloalkyl optionally having substituent(s);
$R^9$ is a group via an oxygen atom; and
ring A is a 5- or 6-membered ring optionally having substituent(s) other than $R^6$ to $R^9$ (except 2-chloro-4-[(2S,3S)-3-hydroxy-2-methylpyrrolidin-1-yl]-3-methylbenzonitrile, 2-chloro-4-[(2S,3S)-3-hydroxy-2-methylpyrrolidin-1-yl]benzonitrile, 4-[(2S,3S)-3-hydroxy-2-methylpyrrolidin-1-yl]benzonitrile, 2-chloro-4-[(2S,3S)-3-hydroxy-2-methylpyrrolidin-1-yl]-5-methylbenzonitrile, 2-chloro-3-ethyl-4-[(2S,3S)-3-hydroxy-2-methylpyrrolidin-1-yl]benzonitrile, 4-[(2S,3S)-3-hydroxy-2-methylpyrrolidin-1-yl]-2-(trifluoromethyl)benzonitrile, 2,3-dichloro-4-[(2S,3S)-3-hydroxy-2-methylpyrrolidin-1-yl]-5-methylbenzonitrile, 2,3-dichloro-4-[(2S,3S)-3-hydroxy-2-methylpyrrolidin-1-yl]benzonitrile, 4-[(2S,3S)-3-hydroxy-2-methylpyrrolidin-1-yl]-3-(trifluoromethyl)benzonitrile, 4-[(2S,3S)-3-hydroxy-2-isopropylpyrrolidin-1-yl]-2-(trifluoromethyl)benzonitrile, 4-[(2S,3R)-3-hydroxy-2-isopropylpyrrolidin-1-yl]-2-(trifluoromethyl)benzonitrile, and 2-chloro-4-[(2S)-3-hydroxy-2-methylpiperidin-1-yl]benzonitrile), or a salt thereof or a prodrug thereof, for the production of an agent for the prophylaxis or treatment of hypogonadism, male climacteric disorder, frailty, cachexia or osteoporosis, and the like.

The definition of the substituents of compound (I) is explained in the following. The "halogen atom" for $R^1$, $R^2$, $R^4$, $R^5$ or $R^6$ is, for example, a fluorine atom, a chlorine atom, a bromine atom or an iodine atom.

Examples of the "group via a carbon atom" for $R^1$, $R^2$, $R^4$, $R^5$ or $R^6$ include cyano, a hydrocarbon group optionally having substituent(s), acyl, optionally esterified carboxyl, imidoyl optionally having substituent(s), amidino optionally having substituent(s), carbamoyl optionally having substituent(s), thiocarbamoyl optionally having substituent(s), a heterocyclic group via a carbon atom and optionally having substituent(s) and the like.

Examples of the above-mentioned "hydrocarbon group optionally having substituent(s)" include alkyl optionally having substituent(s), alkenyl optionally having substituent(s), alkynyl optionally having substituent(s), cycloalkyl optionally having substituent(s), aryl optionally having substituent(s), aralkyl optionally having substituent(s), and the like.

Examples of the "alkyl" of the above-mentioned "alkyl optionally having substituent(s)" include $C_{1-6}$ alkyl (e.g., methyl, ethyl, propyl, isopropyl, butyl, isobutyl, sec-butyl, tert-butyl, pentyl, hexyl etc.) and the like.

Examples of the substituent that the above-mentioned "alkyl optionally having substituent(s)" may have include
(i) a halogen atom (e.g., fluorine atom, chlorine atom, bromine atom and iodine atom),
(ii) $C_{1-6}$ alkoxy (e.g., methoxy, ethoxy, propoxy, isopropoxy, butoxy, isobutoxy, sec-butoxy, tert-butoxy etc.),
(iii) $C_{2-6}$ alkenyl (e.g., vinyl, allyl etc.),
(iv) $C_{2-6}$ alkynyl (e.g., ethynyl, propargyl etc.),
(v) amino,
(vi) mono-$C_{1-6}$ alkylamino (e.g., methylamino, ethylamino, propylamino etc.),
(vii) di-$C_{1-6}$ alkylamino (e.g., dimethylamino, diethylamino, dipropylamino etc.),
(viii) mono-$C_{1-6}$ alkyl-carbonylamino (e.g., acetylamino, ethylcarbonylamino etc.),
(ix) di($C_{1-6}$ alkyl-carbonyl)amino (e.g., di(acetyl)amino, di(ethylcarbonyl)amino, di(propylcarbonyl)amino etc.),
(x) hydroxy,
(xi) cyano,
(xii) amidino,
(xiii) carboxyl,
(xiv) $C_{1-6}$ alkoxy-carbonyl (e.g., methoxycarbonyl, ethoxycarbonyl, propoxycarbonyl etc.),
(xv) carbamoyl,
(xvi) mono-$C_{1-6}$ alkyl-carbamoyl (e.g., methylcarbamoyl, ethylcarbamoyl etc.),
(xvii) di-$C_{1-6}$ alkyl-carbamoyl (e.g., dimethylcarbamoyl, diethylcarbamoyl etc.),
(xviii) cyclic aminocarbonyl (e.g., 1-azetinylcarbonyl, piperidinocarbonyl, morpholinocarbonyl etc.),
(xix) ureido,
(xx) $C_{1-6}$ alkyl-ureido (e.g., methylureido, ethylureido etc.) and the like, and 1 to 3 substituents may be present at substitutable position(s).

Examples of the "alkenyl" of the above-mentioned "alkenyl optionally having substituent(s)" include $C_{2-6}$ alkenyl (e.g., vinyl, allyl etc.) and the like.

Examples of the substituent that the above-mentioned "alkenyl optionally having substituent(s)" may have include those similar to the substituent that the above-mentioned "alkyl optionally having substituent(s)" may have and $C_{1-6}$ alkyl (e.g., methyl, ethyl, propyl, isopropyl, butyl, isobutyl, sec-butyl, tert-butyl, pentyl, hexyl etc.) and the like, and 1 to 3 substituents may be present at substitutable position(s).

Examples of the "alkynyl" of the above-mentioned "alkynyl optionally having substituent(s)" include $C_{2-6}$ alkynyl (e.g., ethynyl, propargyl etc.) and the like.

Examples of the substituent that the above-mentioned "alkynyl optionally having substituent(s)" may have include those similar to the substituent that the above-mentioned "alkenyl optionally having substituent(s)" may have and the like, and 1 to 3 substituents may be present at substitutable position(s).

Examples of the "cycloalkyl" of the above-mentioned "cycloalkyl optionally having substituent(s)" include $C_{3-8}$ cycloalkynyl (e.g., cyclopropyl, cyclobutyl, cyclopentyl, cyclohexyl, cycloheptyl, cyclooctyl etc.) and the like.

Examples of the substituent that the above-mentioned "cycloalkyl optionally having substituent(s)" may have include those similar to the substituent that the above-mentioned "alkenyl optionally having substituent(s)" may have and the like, and 1 to 3 substituents may be present at substitutable position(s).

Examples of the above-mentioned "aryl optionally having substituent(s)" include $C_{6-14}$ aryl (e.g., phenyl, naphthyl, anthryl etc.) and the like.

Examples of the substituent that the above-mentioned "aryl optionally having substituent(s)" may have include those similar to the above-mentioned "alkenyl optionally having substituent(s)" may have and the like, and 1 to 3 substituents may be present at substitutable position(s).

Examples of the "aralkyl" of the above-mentioned "aralkyl optionally having substituent(s)" include $C_{7-14}$ aralkyl (e.g., benzyl, phenylethyl, naphthylmethyl etc.) and the like.

Examples of the substituent that the above-mentioned "aralkyl optionally having substituent(s)" may have include those similar to the above-mentioned "alkenyl optionally having substituent(s)" may have and the like, and 1 to 3 substituents may be present at substitutable position(s).

Examples of the above-mentioned "acyl" include a group formed by binding of the above-mentioned "hydrocarbon group optionally having substituent(s)" to carbonyl.

Examples of the above-mentioned "optionally esterified carboxyl" include carboxyl optionally esterified by the above-mentioned "hydrocarbon group optionally having substituent(s)".

Examples of the above-mentioned "imidoyl optionally having substituent(s)" include imidoyl optionally having 1 or 2 of the above-mentioned "hydrocarbon group optionally having substituent(s)".

Examples of the above-mentioned "amidino optionally having substituent(s)" include amidino optionally having 1 to 3 of the above-mentioned "hydrocarbon group optionally having substituent(s)".

Examples of the above-mentioned "carbamoyl optionally having substituent(s)" include carbamoyl optionally having 1 or 2 of the above-mentioned "hydrocarbon group optionally having substituent(s)".

Examples of the above-mentioned "thiocarbamoyl optionally having substituent(s)" include thiocarbamoyl optionally having 1 or 2 of the above-mentioned "hydrocarbon group optionally having substituent(s)".

Examples of the above-mentioned "heterocyclic group via a carbon atom" of the "heterocyclic group via a carbon atom and optionally having substituent(s)" include an aromatic heterocyclic group, a saturated or unsaturated nonaromatic heterocyclic group (aliphatic heterocyclic group) having, as a ring system-constituting atom (ring atom), 1 to 3 kinds (preferably 1 or two kinds) of at least one (preferably 1 to 4, more preferably 1 or 2) hetero atom selected from oxygen atom, sulfur atom and nitrogen atom etc., and having a bond on a carbon atom and the like.

As the "aromatic heterocyclic group", for example, a 5- or 6-membered monocyclic aromatic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like and, for example, a 8- to 12-membered condensed polycyclic aromatic heterocyclic group such as benzofuranyl, isobenzofuranyl, benzo[b]thienyl, indolyl, isoindolyl, 1H-indazolyl, benzindazolyl, benzoxazolyl, 1,2-benzoisoxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acrydinyl, phenoxazinyl, phenothiazinyl, phenazinyl, phenoxathiinyl, thianthrenyl, phenanthridinyl, phenathrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like, and the like are used.

As the "nonaromatic heterocyclic group", for example, a 3- to 8-membered (preferably 5- or 6-membered) saturated or unsaturated (preferably saturated) nonaromatic heterocyclic group (aliphatic heterocyclic group) such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl and the like, and the like, or a nonaromatic heterocyclic group wherein the double bond of the aforementioned monocyclic aromatic heterocyclic group or condensed polycyclic aromatic heterocyclic group is partly or entirely saturated such as 1,2,3,4-tetrahydroquinolyl, 1,2,3,4-tetrahydroisoquinolyl and the like, and the like are used.

Examples of the substituent that the above-mentioned "heterocyclic group via a carbon atom and optionally having substituent(s)" may have include those similar to the substituents that the above-mentioned "alkenyl optionally having substituent(s)" may have and the like, and 1 to 3 substituents may be present at substitutable position(s).

Examples of the "group via nitrogen atom" for $R^1$, $R^2$, $R^4$, $R^5$ or $R^6$ include (i) amino, (ii) amino monosubstituted by the above-mentioned "group via a carbon atom", (iii) amino disubstituted by the above-mentioned "group via a carbon atom" and $C_{1-6}$ alkyl (e.g., methyl, ethyl, propyl etc.) and the like.

Examples of the "group via an oxygen atom" for $R^1$, $R^2$, $R^4R^5$, $R^6$ or $R^9$ include hydroxy optionally substituted by the above-mentioned "group via a carbon atom" and the like.

Examples of the "group via a sulfur atom" for $R^1$, $R^2$, $R^4$, $R^5$ or $R^6$ include mercapto optionally substituted by the above-mentioned "group via a carbon atom" and the like. The mercapto may be oxidized.

The electron-withdrawing group for $R^3$ generally refers to a group that tends to draw electrons from others in a molecule based on hydrogen as a standard, and is not particularly limited as long as it can be used for organic chemistry. Examples thereof include cyano, nitro, a halogen atom (e.g., fluorine atom, chlorine atom, bromine atom, iodine atom), acyl (those similar to the above-mentioned "acyl"), optionally esterified carboxyl (those similar to the above-mentioned "optionally esterified carboxyl"), optionally substituted carbamoyl (those similar to the above-mentioned "optionally substituted carbamoyl"), $C_{1-6}$ alkyl substituted by 1 to 5 halogen atoms (e.g., fluoromethyl, chloromethyl, difluoromethyl, dichloromethyl, trifluoromethyl, trichloromethyl etc.) and the like.

Examples of the "alkyl optionally having substituent(s)" for $R^7$ or $R^8$ include those similar to the above-mentioned "alkyl optionally having substituent(s)".

Examples of the "alkenyl optionally having substituent(s)" for $R^8$ include those similar to the above-mentioned "alkenyl optionally having substituent(s)".

Examples of the "cycloalkyl optionally having substituent(s)" for $R^8$ include those similar to the above-mentioned "cycloalkyl optionally having substituent(s)".

Ring A is a 5- or 6-membered ring optionally having substituent(s) other than $R^6$ to $R^9$. Examples of ring A include pyrrolidine ring and piperidine ring.

Examples of the substituent that ring A may further have include those similar to the substituent that the above-mentioned "alkenyl optionally having substituent(s)" may have and the like, and 1 to 3 substituents may be present at substitutable position(s).

$R^1$ is preferably a hydrogen atom or alkyl optionally having substituent(s), and (i) a hydrogen atom or (ii) $C_{1-6}$ alkyl optionally having halogen atom(s) is more preferable. Particularly, (i) a hydrogen atom or (ii) methyl optionally having fluorine atom(s) is preferable.

$R^2$ is preferably a hydrogen atom, a halogen atom, alkyl optionally having substituent(s) or alkoxy optionally having substituent(s). Among these, a hydrogen atom, a halogen atom, or $C_{1-6}$ alkyl optionally having halogen atom(s) or $C_{1-6}$ alkoxy is preferable. Particularly, a hydrogen atom, a fluorine atom, a chlorine atom, methyl optionally having a fluorine atom or methoxy is preferable.

$R^3$ is preferably cyano.

$R^4$ is preferably a hydrogen atom or a halogen atom. Of these, a hydrogen atom or a fluorine atom is preferable.

$R^5$ is preferably a hydrogen atom.

$R^6$ is preferably a hydrogen atom.

$R^7$ is preferably alkyl optionally having substituent(s). Among these, $C_{1-6}$ alkyl is preferable. Particularly, methyl, ethyl or isopropyl is preferable.

$R^8$ is preferably a hydrogen atom, alkyl optionally having substituent(s), alkenyl optionally having substituent(s) or cycloalkyl optionally having substituent(s). Of these, a hydrogen atom, $C_{1-6}$ alkyl, $C_{2-6}$ alkenyl or $C_{3-8}$ cycloalkyl optionally having a halogen atom is preferable. Particularly, a hydrogen atom, methyl optionally having a fluorine atom, ethyl, propyl, vinyl or cyclopropyl is preferable.

$R^9$ is preferably hydroxy.

Ring A is preferably a 5-membered ring (pyrrolidine ring) optionally having, other than $R^6$ to $R^9$, 1 to 3 substituents selected from a halogen atom and $C_{1-6}$ alkyl. Among these, a 5-membered ring (pyrrolidine ring) optionally having, other than $R^6$ to $R^9$, 1 or 2 methyl is preferable.

As compound (I), a compound wherein $R^1$ is a hydrogen atom or alkyl optionally having substituent(s);

$R^2$ is a hydrogen atom, a halogen atom, alkyl optionally having substituent(s) or alkoxy optionally having substituent(s);

$R^3$ is cyano;

$R^4$ is a hydrogen atom or a halogen atom;

$R^5$ is a hydrogen atom;

$R^6$ is a hydrogen atom;

$R^7$ is alkyl optionally having substituent(s);

$R^8$ is a hydrogen atom, alkyl optionally having substituent(s), alkenyl optionally having substituent(s) or cycloalkyl optionally having substituent(s);

$R^9$ is hydroxy; and ring A is a 5-membered ring optionally having, other than $R^6$ to $R^9$, $C_{1-6}$ alkyl is preferable.

Particularly, a compound wherein $R^1$ is (i) a hydrogen atom or (ii) $C_{1-6}$ alkyl optionally having halogen atom(s);

$R^2$ is a hydrogen atom, a halogen atom, $C_{1-6}$ alkyl optionally having halogen atom(s), or $C_{1-6}$ alkoxy;

$R^3$ is cyano;

$R^4$ is a hydrogen atom or a halogen atom;

$R^5$ is a hydrogen atom;

$R^6$ is a hydrogen atom;

$R^7$ is $C_{1-6}$ alkyl;

$R^8$ is a hydrogen atom, $C_{1-6}$ alkyl, $C_{2-6}$ alkenyl or $C_{3-8}$ cycloalkyl;

$R^9$ is hydroxy; and ring A is a pyrrolidine ring optionally having, other than $R^6$ to $R^9$, 1 or 2 methyl is preferable.

More particularly, a compound wherein $R^1$ is (i) a hydrogen atom or (ii) methyl optionally having fluorine atom(s);

$R^2$ is a hydrogen atom, a fluorine atom, a chlorine atom, methyl optionally having fluorine atom(s) or methoxy;

$R^3$ is cyano;

$R^4$ is a hydrogen atom or a fluorine atom;

$R^5$ is a hydrogen atom;

$R^6$ is a hydrogen atom;

$R^7$ is methyl, ethyl or isopropyl;

$R^8$ is a hydrogen atom, methyl, ethyl, propyl, vinyl or cyclopropyl;

$R^9$ is hydroxy; and ring A is a pyrrolidine ring optionally having, other than $R^6$ to $R^9$, 1 or 2 methyl is preferable.

More specifically, the below-mentioned compounds described in Examples 1-63 or a salt thereof is preferable.

Particularly, 2-fluoro-4-[(2S,3S)-3-hydroxy-2,3-dimethylpyrrolidin-1-yl]benzonitrile (Example 1), 2-fluoro-4-[(2S,3S)-3-hydroxy-2,3-dimethylpyrrolidin-1-yl]-3-methylbenzonitrile (Example 2), 4-[(2S,3S)-3-ethyl-3-hydroxy-2-methylpyrrolidin-1-yl]-2,6-difluorobenzonitrile (Example 7), 2-chloro-4-[(2S,3S)-3-hydroxy-2-methyl-3-(trifluoromethyl)pyrrolidin-1-yl]benzonitrile (Example 18), 2,6-difluoro-4-[(2S,3S)-3-hydroxy-2-isopropyl-3-methylpyrrolidin-1-yl]benzonitrile (Example 20), 4-[(2S,3R)-3-cyclopropyl-3-hydroxy-2-methylpyrrolidin-1-yl]-2-fluorobenzonitrile (Example 32), or a salt thereof is preferable.

The production methods of compound (I) are described in the following. Compound (I) can be produced by general organic synthetic methods, or according to known synthetic methods (e.g., WO2004/016576).

Compound (I) can be produced, for example, by reacting a compound represented by the formula (II)

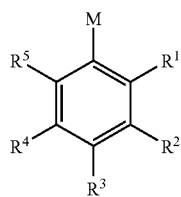

(II)

wherein M is a leaving group, and other symbols are as defined above, or a salt thereof, with a compound represented by the formula (III)

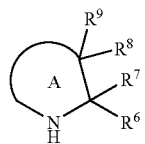

(III)

wherein each symbol is as defined above, or a salt thereof, and, when a protecting group is present, removal of the protecting group should be done.

As the "leaving group" for M, for example, a halogen such as fluorine, chlorine, bromine, iodine and the like, trifluoromethanesulfonyloxy, p-toluenesulfonyloxy, methanesulfonyloxy and the like can be used.

The compound (III) or a salt thereof is generally used in an amount of 1 to 3 mol per 1 mol of compound (II). The reaction also proceeds smoothly by, where necessary, the addition of a base such as lithium carbonate, potassium carbonate, sodium carbonate, cesium carbonate, sodium hydrogen carbonate, sodium hydroxide, sodium tert-butoxide, potassium tert-butoxide, triethylamine, diisopropylethylamine (DIEA), pyridine, 4-(dimethylamino)pyridine (DMAP), 1,8-diazabicyclo[5,4,0]undec-7-ene (DBU), 1,5-diazabicyclo[4,3,0]non-5-ene(DBN) and the like. Furthermore, the use of a transition metal catalyst (e.g., J.O.C., 1997, 62, pp 1264-1267) as a catalyst is also preferable.

The reaction can be performed in an inert solvent, for example, methanol, ethanol, propanol, isopropanol, n-butanol, tetrahydrofuran, diethyl ether, acetonitrile, acetone, ethyl acetate, 1,2-dimethoxyethane, 1,4-dioxane, toluene, benzene, xylene, dichloromethane, chloroform, 1,2-dichloroethane, N,N-dimethylformamide (DMF), dimethyl sulfoxide (DMSO) etc., or a mixed solvent thereof. The reaction can be performed in a temperature range of about 0° C. to 180° C. The reaction time is not particularly limited but it is generally 0.1 hr to 100 hr, preferably 0.5 hr to 72 hr.

Moreover, one or more substituents on ring A in compound (I) can be converted to other substituents. For example, it is possible to reduce a carbonyl group to alcohol, lead alcohol to olefin by dehydration, or alkylate alcohol to ether according to a method known per se.

The compounds (II) and (III) used as starting substances can be synthesized by a known method or a method analogous thereto and, for example, can be produced by a method shown in the Reference Examples shown below.

Here, the group in the above-mentioned formulas may be protected by a protecting group generally used for organic synthesis. Where desired, the protecting group can be removed after the reaction by a known method.

Thus-obtained compound (I) can be isolated and purified by a separation means known per se, such as concentration, concentration under reduced pressure, solvent extraction, liquid conversion, salting out, crystallization, recrystallization, phase transfer, chromatography and the like.

When compound (I) is obtained as a free form, it can be converted to a desired salt by a method known per se or a modification thereof; conversely, when compound (I) is obtained as a salt, it can be converted to a free form or other desired salt by a method known per se or a modification thereof.

The compound (I) may be a hydrate or a non-hydrate.

When compound (I) is obtained as a mixture of optically active substances, it can be separated into a desired optically active substances by an optical resolution means known per se.

Compound (I) may be labeled with an isotope (e.g., $^2H$, $^3H$, $^{14}C$ etc.) and the like.

A prodrug of the compound (I) means a compound which is converted to the compound (I) with a reaction due to an enzyme, an gastric acid, etc. under physiological conditions in the living body, that is, a compound which is converted to the compound (I) with oxidation, reduction, hydrolysis, etc. according to an enzyme; a compound which is converted to the compound (I) by hydrolysis etc. due to gastric acid, etc. A prodrug of compound (I) may be a compound obtained by subjecting amino in compound (I) to an acylation, alkylation or phosphorylation (e.g., a compound obtained by subjecting amino in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation, dimethylaminomethylcarbonylation, etc.); a compound obtained by subjecting carboxyl in compound (I) to an esterification or amidation (e.g., a compound obtained by subjecting carboxy in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a method known per se.

A prodrug for compound (I) may also be one which is converted into compound (I) under a physiological condition, such as those described in IYAKUHIN no KAIHATSU (Development of Pharmaceuticals), Vol. 7, Design of Molecules, p. 163-198, 1990, Published by HIROKAWA SHOTEN.

The compound (including prodrug) of the present invention may form a salt. A salt of the compound is not particularly limited as long as it does not inhibit the reaction. For example, a salt with inorganic base, an ammonium salt, a salt with organic base, a salt with inorganic acid, a salt with organic acid, a salt with amino acid and the like can be mentioned. Preferable examples of salts with inorganic base include alkali metal salt such as sodium salt, potassium salt and the like, alkaline earth metal salt such as calcium salt, magnesium salt and the like, and aluminum salt, ammonium salt and the like. Preferable examples of salts with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of salts with inorganic acid include salts with hydrochloric acid, hydrobromic acid, nitric acid, sulfuric acid, phosphoric acid and the like. Preferable examples of salts with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of salts with basic amino acid include salts with arginine, lysine, ornithine and the like, and preferable examples of salts with acidic amino acid include salts with aspartic acid, glutamic acid and the like.

The compound of the present invention (I) or a salt thereof or a prodrug thereof (hereinafter sometimes to be abbreviated as the compound of the present invention) has an androgen receptor regulating action, particularly an androgen receptor agonist action, and can be used for the prophylaxis or treatment of a disease in a mammal, for which administration of an androgen receptor agonist is effective. The disease for which administration of an androgen receptor agonist is effective includes hypogonadism, osteoporosis, hormone resistant cancer (particularly LHRH agonist resistant cancer), climacteric disorder (particularly male climacteric disorder), frailty, cachexia, anemia, arteriosclerosis, Alzheimer's disease, erectile dysfunction, depression, wasting disease, and hypertriglyceridemia (hyperlipidemia) and the like. It can be particularly used for the prophylaxis or treatment of hypogonadism, male climacteric disorder, frailty, cachexia or osteoporosis.

The compound of the present invention has an organ selective androgen receptor regulating action and shows, for example, an antagonist action on prostate and an agonist action on muscle. Specifically, the compound of the present invention has an action to not increase the weight of the prostate at a dose that increases the weight of the muscle (e.g., levator ani muscle and the like). More specifically, the prostate weight increases by about 10% or below (preferably 0% or below) at a dose that increases the weight of levator ani muscle by about 20% or above (preferably about 20%-about 50%). Here, "the prostate weight increases by 0% or below" means no increase or decrease in the prostate weight when an increase in the weight of the prostate is 0%, and when an increase in the prostate weight is less than 0%, it means that the prostate weight decreases by its absolute value. Accordingly, the compound of the present invention can be used as the following medicaments.

(1) frailty suppressive agent.
(2) muscle enhancing agent or muscle increasing agent (providing effects of preventing elderly hospitalized patients from being bedridden, shortening rehabilitation period and the like).
(3) suppressive agent for cachexia caused by, for example, AIDS, cancer and the like.
(4) body weight decrease suppressive agent.
(5) agent for the prophylaxis or treatment of prostatomegaly (decrease prostate weight).
(6) agent for the prophylaxis or treatment of muscular atrophy disorder.
(7) prostate weight decreasing agent.
(8) agent for the prophylaxis or treatment of muscle decrease due to diseases (e.g., muscular dystrophy, muscular atrophy, X-linkage spinal cord medulla oblongata muscular atrophy (SBMA), cachexia, malnutrition, Hansen's disease, diabetes, renal diseases, COPD (chronic obliterative pulmonary diseases), cancer, late stage renal failure, sarcopenia (loss of muscle due to old age), emphysema, osteomalacia, HIV infection, AIDS, cardiomyopathy and the like).
(9) suppressive agent for loss of muscle strength in postmenopausal female.
(10) suppressive agent for bone mineral content lowering in postmenopausal female.
(11) suppressive agent for hot flash (e.g., glow (hot flash) sweating and the like) in postmenopausal female.
(12) mitigator of side effects of LHRH modulator such as LHRH agonist (leuprorelin, goserelin, buserelin, nafarelin, triptorelin, gonadorelin and the like), LHRH antagonist (ganirelix, cetrorelix, antarelix, abarelix, sufugolix and the like) and the like.
(13) suppressive agent for loss of muscle strength after administration of medicaments such as LHRH modulator and the like.
(14) suppressive agent for bone mineral content lowering after administration of medicaments such as LHRH modulator and the like.
(15) suppressive agent for hot flash (e.g., glow (hot flash) sweating and the like) after administration of medicaments such as LHRH modulator and the like.

In addition, the compound of the present invention shows effect as a frailty suppresser, a muscle strength enhancer or a muscle increasing agent while using as an agent for the prophylaxis or treatment of prostatomegaly or an agent for reducing the weight of the prostate. Accordingly, it is expected to shorten the period of rehabilitation without leaving aged inpatients bedridden. Without the side effect of increasing the weight of the prostate, it is expected to provide an agent for the prophylaxis or treatment of prostate cancer in patients with high possibility of prostate cancer. Without the side effect of virilization, moreover, it can be applied to female, and is expected to provide a suppressant of loss of muscle strength or bone mineral density loss in postmenopausal female, or a suppressant of hot flash (hot flash, sweating etc.) in postmenopausal female. Furthermore, it also is expected as an agent for reducing the side effects of LHRH agonists (leuprorelin, goserelin, buserelin, nafarelin, triptorelin, gonadorelin and the like), and LHRH antagonists (ganirelix, cetrorelix, antarelix, abarelix, sufogorikkusu and the like), a suppressant of loss of muscle strength or bone mineral density loss after administration of these medicaments, or a suppressant of hot flash (hot flash, sweating and the like) after administration of these medicaments.

The compound of the present invention achieves growth inhibition and cell death by conversely placing an excessive stimulation on cancer that has acquired resistance to a hormone treatment by being hypersensitive to androgen. Thus, it can be used as an agent for the prophylaxis or treatment of, from various cancers, breast cancer, prostate cancer, endometrial cancer, cancer of the uterine cervix, ovarian cancer, urinary bladder cancer, thyroid cancer, bone tumor and penile cancer, that acquired hormone resistance, and is particularly useful as an agent for the prophylaxis or treatment of prostate cancer.

As hormone resistant cancer, for example, LHRH derivative resistant cancer, preferably LHRH agonist resistant cancer can be mentioned.

The compound of the present invention shows low toxicity and can be used as a medicament as it is, or as a pharmaceutical composition in admixture with a commonly known pharmaceutically acceptable carrier etc. in mammals (e.g., humans, horses, bovines, dogs, cats, rats, mice, rabbits, pigs, monkeys, and the like).

In addition to the compound of the present invention, said pharmaceutical composition may contain other active ingredients, e.g., the following hormonal therapeutic agents, anti-cancer agent (e.g., chemotherapeutic agents, immunotherapeutic agents, or medicaments inhibiting the action of cell growth factors or cell growth factor receptors), antiemetic and the like.

As a medicament for mammals such as humans, the compound of the present invention can be administered orally in the form of, for example, tablets, capsules (including soft capsules and microcapsules), powders, granules and the like, or parenterally in the form of injections, suppositories, pellets and the like. Examples of the "parenteral administration route" include intravenous, intramuscular, subcutaneous, intra-tissue, intranasal, intradermal, instillation, intracerebral, intrarectal, intravaginal, intraperitoneal, intratumoral, juxtaposition of tumor and administration directly to the lesion.

The dose of the compound of the present invention varies depending on the route of administration, symptoms, etc. For example, when it is administered orally as an anticancer agent to a patient (body weight 40 to 80 kg) with breast cancer or prostate cancer, its dose is, for example, 0.1 to 200 mg/kg body weight per day, preferably 1 to 100 mg/kg body weight per day, and more preferably 1 to 50 mg/kg body weight per day. This amount may be administered once or in 2 to 3 divided portions daily.

The compound of the present invention can be orally or parenterally administered in the form of a solid dosage form such as tablet, capsule, granule, powder and the like; or a liquid preparation such as syrup, injection and the like, by admixing with a pharmaceutically acceptable carrier.

As a pharmaceutically acceptable carrier, various organic or inorganic carrier substances conventionally used as preparation materials can be used. For example, excipient, lubricant, binder and disintegrant for solid preparations, solvent, solubilizing agents, suspending agent, isotonicity agent, buffer and soothing agent for liquid preparations and the like can be mentioned. Where necessary, conventional preparation additives such as preservatives, antioxidants, colorants, sweetening agents and the like can be used.

Preferable examples of the excipient include lactose, sucrose, D-mannitol, starch, crystalline cellulose, light anhydrous silicic acid and the like.

Preferable examples of the lubricant include magnesium stearate, calcium stearate, talc, colloidal silica and the like.

Preferable examples of the binder include crystalline cellulose, sucrose, D-mannitol, dextrin, hydroxypropylcellulose, hydroxypropylmethylcellulose, polyvinylpyrrolidone and the like.

Preferable examples of the disintegrant include starch, carboxymethylcellulose, calcium carboxymethylcellulose, croscarmellose sodium, sodium carboxymethyl starch and the like.

Preferable examples of the solvent include water for injection, alcohol, propylene glycol, macrogol, sesame oil, corn oil and the like.

Preferable examples of the solubilizing agents include polyethylene glycol, propylene glycol, D-mannitol, benzyl benzoate, ethanol, trisaminomethane, cholesterol, triethanolamine, sodium carbonate, sodium citrate and the like.

Preferable examples of the suspending agent include surfactants such as stearyltriethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; and the like.

Preferable examples of the isotonicity agent include sodium chloride, glycerol, D-mannitol and the like.

Preferable examples of the buffer include buffers such as phosphate, acetate, carbonate, citrate and the like; and the like.

Preferable examples of the soothing agent include benzyl alcohol and the like.

Preferable examples of the preservative include paraoxybenzoates, chlorobutanol, benzyl alcohol, phenethyl alcohol, dehydroacetic acid, sorbic acid and the like.

Preferable examples of the antioxidant include sulfite, ascorbic acid and the like.

A pharmaceutical composition can be produced according to a conventional method by adding the compound of the present invention generally in a proportion of 0.1 to 95% (w/w) relative to the total amount of the preparation, though subject to change depending on the dosage form, administration method, carrier and the like.

In addition, cancer can be prevented or treated more effectively by a combination of (1) administration of an effective amount of the compound of the present invention and (2) 1 to 3 kinds selected from the group consisting of (i) administration of an effective amount of other anti-cancer agent, (ii) administration of an effective amount of other hormonal therapeutic agent, and (iii) non-medicament therapy. Examples of non-medicament therapy include operation, induced hypertension chemotherapy using angiotensin II and the like, irradiation therapy, gene therapy, thermotherapy, cryotherapy, laser ablation therapy and the like, and two or more kinds thereof can also be combined.

For example, the compound of the present invention can be used in combination with other hormonal therapeutic agents, other anti-cancer agents (e.g., chemotherapeutic agent, immunotherapeutic agent (including vaccines), antibodies, gene therapy drugs, medicaments inhibiting the action of cell growth factors and receptors thereof, medicaments inhibiting angiogenesis), antiemetics and the like (hereinafter to be abbreviated as concomitant drug).

While the compound of the present invention exhibits excellent anticancer action even when used as a simple agent, its effect can be still more enhanced or QOL of patients can be improved by using it in combination with one or more of the concomitant drug(s) mentioned above (multi-agent co-administration).

Examples of the "hormonal therapeutic agent" include fosfestrol, diethylstylbestrol, chlorotrianisene, medroxyprogesterone acetate, acetic acid megestrol, chlormadinone acetate, cyproterone acetate, danazol, dienogest, asoprisnil, allylestrenol, gestrinone, nomegestrol, tadenan, mepartricin, raloxifene, ormeloxifene, levormeloxifene, anti-estrogen (e.g., tamoxifen citrate, toremifene citrate etc.), ER down-regulator(for example, fulvestrant etc.), human postmenopausal gonadotropin, follitropin, pill preparation, mepitiostane, testrolactone, aminoglutethimide, LH-RH derivative (e.g., LH-RH agonist (e.g., goserelin acetate, buserelin, leuprorelin etc.), LH-RH antagonist), droloxifene, epitiostanol, ethinylestradiol sulfonate, aromatase inhibitor (e.g., fadrozole hydrochloride, anastrozole, retrozole, exemestane, vorozole, formestane etc.), anti-androgen agent (e.g., flutamide, bicartamide, nilutamide etc.), 5α-reductase inhibitor (e.g., finasteride, dutasteride, episteride etc.), corticosteroid (e.g., dexamethasone, prednisolone, betamethasone, triamcinolone etc.), androgen synthesis inhibitor (e.g., abiraterone etc.), retinoid and drugs that retard retinoid metabolism (e.g., liarozole etc.) and the like. Preferred is LH-RH derivative.

Examples of the "chemotherapeutic agents" include alkylating agents, antimetabolites, anticancer antibiotics, plant-derived anticancer agents, other chemotherapeutic agents and the like.

Examples of the "alkylating agent" include nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, carboquone, adozelesin, cystemustine, bizelesin, and the like.

Examples of the "antimetabolites" include mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emitefur etc.), aminopterine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine and the like.

Examples of the "antitumor antibiotics" include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride and the like.

Examples of the "plant-derived antitumor agent" include etoposide, etoposide phosphate, vinblastine sulfate, vincristine sulfate, vindesine sulfate, teniposide, paclitaxel, docetaxel, DJ-927, vinorelbine, irinotecan, topotecan and the like.

Examples of the "other chemotherapeutic agents" include sobuzoxane and the like.

Examples of the "immunotherapeutic agent (BRM)" include picibanil, krestin, schizophyllan, lentinan, ubenimex, interferon, interleukin, macrophage colony stimulating agent, granulocyte colony stimulating factor, erythropoietin, lymphotoxin, Corynebacterium parvum, levamisole, polysaccharide K, procodazole and the like. As the vaccine, BCG vaccine, PROVENGE, Onyvax-P, PROSTVAC-VF, GVAX, DCVax-Prostate, SAPOIMMUNE, VPM-4-001 and the like are used.

As the "antibody", antibody against EpiCAM, antibody against PSCA, and antibody against PSMA are used.

The "growth factor" in said "medicaments inhibiting the action of cell growth factors and receptors thereof" may be any as long as it promotes cell proliferation, which is normally peptide having a molecular weight of not more than 20,000 that is capable of exhibiting its activity at low concentrations by binding to a receptor. Examples thereof include (1) EGF (epidermal growth factor) or substances possessing substantially the same activity as it [e.g., EGF, heregulin (HER2 ligand), TGF-α, HB-EGF and the like], (2) insulin or substances possessing substantially the same activity as it [e.g., insulin, IGF (insulin-like growth factor)-1, IGF-2, and the like], (3) FGF (fibroblast growth factor) or substances possessing substantially the same activity as it [e.g., acidic FGF, basic FGF, KGF (keratinocyte growth factor), FGF-10, and the like], (4) other cell growth factors [e.g., CSF (colony stimulating factor), EPO (erythropoietin), IL-2(interleukin-2), NGF (nerve growth factor), PDGF (platelet-derived growth factor), TGFβ (transforming growth factor β) HGF (hepatocyte growth factor), VEGF (vascular endothelial cell growth factor), and the like], and the like.

The "receptor of cell growth factor" may be any as long as it can bind to the above-mentioned cell growth factor, and specific examples thereof include EGF receptor and HER2, HER3 and HER4 belonging to the same family, insulin receptor, IGF receptor, FGF receptor-1, FGF receptor-2 and the like.

Examples of the "medicaments inhibiting the action of cell growth factors and receptors thereof" include trastuzumab (herceptin (trademark); HER2 antibody), imatinib mesylate, ZD1839, cetuximab, gefitinib, erlotinib and the like.

As the "medicaments inhibiting angiogenesis", antibody to VEGF (e.g., bevacizumab), antibody to VEGF receptor, VEGF receptor kinase inhibitor (e.g., SU11248 etc.), PDGF receptor kinase inhibitor, Tie2 kinase inhibitor, thalidomide and the like are used.

Besides the aforementioned medicament, L-asparaginase, aceglatone, procarbazine hydrochloride, protoporphyrin-cobalt complex salt, mercuric hematoporphyrin-sodium, differentiation inducer (e.g., retinoid, vitamin D etc.), α-blocker (e.g., tamsulosin hydrochloride, naftopidil, urapidil, alfuzosin, terazosin, prazosin, silodosin etc.) serine/threonine kinase inhibitor, endothelin receptor antagonist (e.g., atrasentan etc.), proteasome inhibitor (e.g., bortezomib etc.), Hsp90 inhibitor (e.g., 17-AAG etc.), spironolactone, minoxidil, 11α-hydroxyprogesterone, bone resorption inhibitory metastasis suppressing agent (e.g., zoledronic acid, alendronic acid, pamidronic acid, etidronic acid, ibandronic acid, clodronic acid) and the like can also be used.

As the "antiemetic", gastric motility enhancers such as 5-$HT_3$ antagonist such as ondansetron, tropisetron hydrochloride, azasetron, ramosetron, granisetron, dolasetron mesylate, palonosetron and the like, 5-$HT_4$ antagonists such as domperidone, mosapride, metoclopramide and the like, and the like; gastrointestinal tract motility regulators such as trimebutine and the like; phenothiazine medicaments such as prochlorperazine maleate, promethazine, thiethylperazine and the like; tranquilizers such as haloperidol, chlorpromazine phenolphthalinate, diazepam, droperidol and the like; steroids such as dexamethasone, prednisolone, betamethasone, triamcinolone and the like; as well as dimethylhydrin acid, diphenhydramine, hyoscine, hyoscine hydrobromide, tetrabenazine and the like can be used.

As the aforementioned LH-RH derivative, an LH-RH derivative or a salt thereof effective for hormone-dependent disease, particularly sex hormone-dependent disease such as sex hormone-dependent cancer (e.g., prostate cancer, uterus cancer, breast cancer, pituitary gland tumor, liver cancer and the like), prostatomegaly, endometriosis, hysteromyoma, precocity, dysmenorrhea, amenorrhea, premenstrual syndrome, polycystic ovary syndrome and the like and contraception (or infertility when rebound effect after cessation of the drug is used) are used. In addition, an LH-RH derivative or a salt thereof effective for benignant or malignant tumor, which is sex hormone independent but LH-RH sensitive, and the like is also used.

Specific examples of the LH-RH derivative or a salt thereof include peptides described in Treatment with GnRH analogs: Controversies and perspectives (The Parthenon Publishing Group Ltd., published in 1996), JP-A-3-503165, JP-A-3-101695, JP-A-7-97334, JP-A-8-259460 and the like.

Examples of the LH-RH derivative include an LH-RH agonist and an LH-RH antagonist. As the LH-RH antagonist, for example, physiologically active peptide represented by the formula

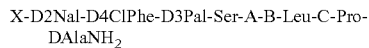

wherein X is N(4H$_2$-furoyl)Gly or NAc, A is a residue selected from NMeTyr, Tyr, Aph(Atz) and NMeAph(Atz), B is a residue selected from DLys(Nic), DCit, DLys(AzaglyNic), DLys(AzaglyFur), DhArg(Et$_2$), DAph(Atz) and DhCi, and C is Lys(Nisp), Arg or hArg(Et$_2$), or a salt thereof and the like are used, particularly preferably abarelix, ganirelix, cetrorelix, 5-(N-benzyl-N-methylaminomethyl)-1-(2,6-difluorobenzyl)-6-[4-(3-methoxyureido)phenyl]-3-phenylthieno[2,3-d]pyrimidine-2,4(1H, 3H)-dione, 5-(N-benzyl-N-methylaminomethyl)-1-(2,6-difluorobenzyl)-6-[4-(3-ethylureido)phenyl]-3-phenylthieno[2,3-d]pyrimidine-2,4(1H, 3H)-dione, 5-(N-benzyl-N-methylaminomethyl)-1-(2,6-difluorobenzyl)-6-[4-(3-ethylureido)phenyl]-3-phenylthieno[2,3-d]pyrimidine-2,4(1H, 3H)-dione hydrochloride and the like are used.

As the LH-RH agonist, for example, physiologically active peptides represented by the formula

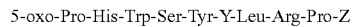

wherein Y is a residue selected from DLeu, DAla, DTrp, DSer(tBu), D2Nal and DHis(ImBzl), and Z is NH—C$_2$H$_5$ or Gly-NH$_2$, or a salt thereof and the like are used. For example, they are goserelin acetate, buserelin and the like. Particularly, peptide wherein Y is DLeu and Z is NH—C$_2$H$_5$ (i.e., peptide A represented by 5-oxo-Pro-His-Trp-Ser-Tyr-DLeu-Leu-Arg-Pro-NH—C$_2$H$_5$; leuprorelin) or a salt thereof (e.g., acetate) is preferable.

When the amino acid, peptide, protecting group and the like of the polypeptide described in the present specification are indicated using abbreviations, they are based on the abbreviations according to the IUPAC-IUB Commission on Biochemical Nomenclature or conventional abbreviations in the field. When an optical isomer due to amino acid is present, it means an L substance unless otherwise specified.

Examples of the abbreviations are as follows.
Abu: aminobutyric acid
Aibu: 2-aminobutyric acid
Ala: alanine
Arg: arginine
Gly: glycine
His: histidine
Ile: isoleucine
Leu: leucine
Met: methionine
Nle: norleucine
Nval: norvaline
Phe: phenylalanine
Phg: phenylglycine
Pro: proline
(Pyr)Glu: pyroglutamic acid
Ser: serine
Thr: threonine
Trp: tryptophan
Tyr: tyrosine
Val: valine
D2Nal: D-3-(2-naphthyl)alanine residue
DSer(tBu): O-tert-butyl-D-serine
DHis(ImBzl): N$^{im}$-benzyl-D-histidine
PAM: phenylacetamidomethyl
Boc: t-butyloxycarbonyl
Fmoc: 9-fluorenylmethyloxycarbonyl
Cl—Z: 2-chloro-benzyloxycarbonyl
Br—Z: 2-bromo-benzyloxycarbonyl
Bzl: benzyl
Cl$_2$-Bzl: 2,6-dichlorobenzyl
Tos: p-toluenesulfonyl
HONb: N-hydroxy-5-norbornane-2,3-dicarboxylmide
HOBt: 1-hydroxybenzotriazole
HOOBt: 3-hydroxy-3,4-dihydro-4-oxo-1,2,3-benzotriazine
MeBzl: 4-methylbenzyl
Bom: benzyloxymethyl
Bum: t-butoxy methyl
Trt: trityl
DNP: dinitrophenyl
DCC: N,N'-dicyclohexylcarbodiimide Of the aforementioned drugs, preferable concomitant drugs are an LH-RH agonist (e.g., goserelin acetate, buserelin, leuprorelin etc.) and the like.

When using the compound of the present invention and a concomitant drug in combination, the administration time of the compound of the present invention and the concomitant drug is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the compound of the present invention and the concomitant drug is not particularly limited, and the compound of the present invention and the concomitant drug only need to be combined on administration. Examples of such administration mode include the following: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like. In the following, these administration modes are collectively abbreviated as the concomitant drug of the present invention.

The concomitant drug of the present invention has low toxicity, and for example, the compound of the present invention and/or the above-mentioned concomitant drug can be mixed, according to a method known per se, with a pharmacologically acceptable carrier to give pharmaceutical compositions, such as tablets (including sugar-coated tablet, film-coated tablet), powders, granules, capsules (including soft capsule), solutions, injections, suppositories, sustained release agents and the like, which can be safely administered orally or parenterally (e.g., local, rectum, vein, and the like). An injection can be administered intravenously, intramuscularly, subcutaneously, into the organ, intranasally, intradermally, by instillation, intracerebrally, intrarectally, vaginally and intraperitoneally, intratumorally, proximally to the tumor and the like, or directly to the lesion.

As a pharmacologically acceptable carrier which may be used for producing the concomitant drug of the present invention, those similar to the aforementioned pharmacologically acceptable carriers that can be used for the pharmaceutical composition of the present invention can be used.

The compounding ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to 100% by weight, preferably from about 0.1 to 50% by weight, further preferably from about 0.5 to 20% by weight, based on the entire preparation.

The content of the concomitant drug in the combination agent of the present invention differs depending on the form of a preparation, and usually from about 0.01 to 100% by weight, preferably from about 0.1 to 50% by weight, further preferably from about 0.5 to 20% by weight, based on the entire preparation.

The content of additives such as carrier and the like in the combination agent of the present invention differs depending on the form of a preparation, and usually from about 1 to 99.99% by weight, preferably from about 10 to 90% by weight, based on the entire preparation.

In the case when the compound of the present invention and the concomitant drug are separately prepared respectively, the same contents may be adopted.

These preparations can be produced by a method known per se usually used in a preparation process.

For example, the compound of the present invention and the concomitant drug can be made into an aqueous injection together with a dispersing agent (e.g., Tween 80(manufactured by Atlas Powder, US), HCO 60(manufactured by Nikko Chemicals), polyethylene glycol, carboxymethylcellulose, sodium alginate, hydroxypropylmethylcellulose, dextrin and the like), a stabilizer (e.g., ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, mannitol, sorbitol, glucose and the like), a pH regulator (e.g., hydrochloric acid, sodium hydroxide and the like), a preservative (e.g., ethyl parahydroxybenzoate, benzoic acid, methylparaben, propylparaben, benzyl alcohol and the like), a dissolving agent (e.g., conc. glycerin, meglumine and the like), a solubilizing agent (e.g., propylene glycol, sucrose and the like), a soothing agent (e.g., glucose, benzyl alcohol and the like), and the like, or can be dissolved, suspended or emulsified in a vegetable oil such as olive oil, sesame oil, cotton seed oil, corn oil and the like or a solubilizing agent such as propylene glycol and prepared into an oily injection, whereby an injection is afforded.

To produce a preparation for oral administration, an excipient (e.g., lactose, sucrose, starch and the like), a disintegrating agent (e.g., starch, calcium carbonate and the like), a binder (e.g., starch, gum Arabic, carboxymethylcellulose, polyvinylpyrrolidone, hydroxypropylcellulose and the like), a lubricant (e.g., talc, magnesium stearate, polyethylene glycol 6000 and the like) and the like, for example, can be added to the compound of the present invention or the concomitant drug, according to a method known per se, and the mixture can be compression-molded, then if desirable, the molder product can be coated by a method known per se for the purpose of masking of taste, enteric property or durability, to obtain a preparation for oral administration. As the coating agent, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudoragit (methacrylic acid·acrylic acid copolymer, manufactured by Rohm, DE), pigment (e.g., iron oxide red, titanium dioxide, etc.) and the like can be used. The preparation for oral administration may be any of a immediate-release preparation and a sustained release preparation.

For example, to give a suppository, the compound of the present invention and the concomitant drug can be made into an oily or aqueous solid, semisolid or liquid suppository according to a method known per se. As the oily substrate to be used for the aforementioned composition, for example, glycerides of higher fatty acids [e.g., cacao butter, Witepsols (manufactured by Dynamit Nobel, Germany), etc.], medium chain fatty acid [e.g., Miglyols (manufactured by Dynamit Nobel, Germany), etc.], or vegetable oils (e.g., sesame oil, soybean oil, cotton seed oil and the like), and the like are listed. Further, as the aqueous substrate, for example, polyethylene glycols, propylene glycol are listed, and as the aqueous gel substrate, for example, natural gums, cellulose derivatives, vinyl polymers, acrylic acid polymers and the like are listed.

As the above-mentioned sustained release preparation, sustained release microcapsules and the like are used.

The sustained release microcapsule can be produced by a method known per se and, for example, a sustained-release preparation such as the one shown in the following [2] is preferably formed and administered.

The compound of the present invention is preferably molded into an oral administration preparation such as a solid preparation (e.g., powder, granule, tablet, capsule) and the like, or molded into a rectal administration preparation such as a suppository. Particularly, an oral administration preparation is preferable.

The concomitant drug can be made into the above-mentioned drug form depending on the kind of the drug.

[1] An injection of the compound of the present invention or the concomitant drug, and preparation thereof, [2] a sustained release preparation or immediate-release preparation of the compound of the present invention or the concomitant drug, and preparation thereof, [3] a sublingual, buccal or intraoral quick integrating agent of the compound of the present invention or the concomitant drug, and preparation thereof, will be specifically described in the following.

[1] Injection and Preparation Thereof

An injection prepared by dissolving the compound of the present invention or the concomitant drug into water is preferable. This injection may be allowed to contain a benzoate and/or salicylate.

The injection is obtained by dissolving the compound of the present invention or the concomitant drug, and if desirable, a benzoate and/or salicylate, into water.

As the above-mentioned salts of benzoic acid and salicylic acid, for example, salts of alkali metals such as sodium, potassium and the like, salts of alkaline earth metals such as calcium, magnesium and the like, ammonium salts, meglumine salts, salts with organic acid such as tromethamol and the like, etc. are used.

The concentration of the compound of the present invention or the concomitant drug in an injection is from 0.5 to 50 w/v %, preferably from 3 to 20 w/v %. The concentration of a benzoate or/and salicylate is from 0.5 to 50 w/v %, preferably from about 3 to 20 w/v %.

Into this injection, additives usually used in an injection, for example, a stabilizer (e.g., ascorbic acid, sodium pyrosulfite and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride and the like), a dispersing agent (e.g., hydroxypropylmethylcellulose, dextrin), a pH regulator (e.g., hydrochloric acid, sodium hydroxide and the like), a preservative (e.g., ethyl parahydroxybenzoate, benzoic acid and the like), a dissolving agent (e.g., conc. glycerin, meglumine and the like), a solubilizing agent (e.g., propylene glycol, sucrose and the like), a soothing agent (e.g., glucose, benzyl alcohol and the like), and the like, can be appropriately blended. These additives are generally blended in a proportion usually used in an injection.

It is advantageous that pH of an injection is controlled from pH 2 to 12, preferably from pH 2.5 to 8.0 by addition of a pH regulator.

An injection is obtained by dissolving the compound of the present invention or the concomitant drug and if desirable, a benzoate and/or a salicylate, and if necessary, the above-mentioned additives into water. These may be dissolved in any order, and can be appropriately dissolved in the same manner as in a conventional method of producing an injection.

An aqueous solution for injection is advantageously heated, alternatively, for example, filter sterilization, high pressure heat sterilization and the like can be conducted in the same manner as for a usual injection, to provide an injection.

It is advantageous that an aqueous solution for injection be subjected to high pressure heat sterilization at 100 to 121° C. for 5 to 30 min.

Further, a preparation endowed with an antibacterial property of a solution may also be produced so that it can be used as a preparation which is divided and administered multiple-times.

[2] Sustained Release Preparation or Immediate-release Preparation, and Preparation Thereof A sustained release preparation is preferable, which is obtained, if desirable, by coating a nucleus containing the compound of the present invention or the concomitant drug with a film agent such as a water-insoluble substance, swellable polymer and the like. For example, a sustained release preparation for oral administration of once administration per day type is preferable.

As the water-insoluble substance used in a film agent, there are listed, for example, cellulose ethers such as ethylcellulose, butylcellulose and the like, cellulose esters such as cellulose acetate, cellulose propionate and the like, polyvinyl esters such as polyvinyl acetate, polyvinyl butyrate and the like, acrylic acid/methacrylic acid copolymers, methyl methacrylate copolymers, ethoxyethyl methacrylate/cinnamoethyl methacrylate/aminoalkyl methacrylate copolymers, polyacrylic acid, polymethacrylic acid, methacrylic acid alkylamide copolymers, poly(methyl methacrylate), polymethacrylates, polymethacrylamides, aminoalkyl methacrylate copolymers, poly(methacrylic anhydride), glycidyl methacrylate copolymers, particularly, acrylic acid-based polymers such as Eudoragit (Rohm Pharma) such as Eudoragit RS-100, RL-100, RS-30D, RL-30D, RL-PO, RS-PO (ethyl acrylate/methyl methacrylate/trimethylammonium-ethyl methacrylate chloride copolymer), Eudoragit NE-30D (methyl methacrylate/ethyl acrylate copolymer), and the like, hydrogenated oils such as hydrogenated castor oil (e.g., Lubri wax (Freund Corporation) and the like) and the like, waxes such as carnauba wax, glycerin fatty acid ester, paraffin and the like, polyglycerin fatty esters, and the like.

As the swellable polymer, polymers having an acidic dissociating group and showing pH-dependent swelling are preferable, and polymers having an acidic dissociating group, which manifest small swelling in acidic regions such as in stomach and large swelling in neutral regions such as in small intestine and large intestine, are preferable.

As such a polymer having an acidic dissociating group and showing pH-dependent swelling, cross-linkable polyacrylic acid polymers such as, for example, Carbomer 934P, 940, 941, 974P, 980, 1342 and the like, polycarbophil, calcium polycarbophil (last two are manufactured by BF Goodrich), Hiviswako 103, 104, 105, 304(all are manufactured by Wako Pure Chemical Industries, Ltd.), and the like, are listed.

The film agent used in a sustained release preparation may further contain a hydrophilic substance.

As the hydrophilic substance, for example, polysaccharides which may contain a sulfate group such as pullulan, dextrin, alkali metal alginate and the like, polysaccharides having hydroxyalkyl or carboxyalkyl such as hydroxypropylcellulose, hydroxypropylmethylcellulose, carboxymethylcellulose sodium and the like, methylcellulose, polyvinylpyrrolidone, polyvinyl alcohol, polyethylene glycol and the like can be mentioned.

The content of a water-insoluble substance in the film agent of a sustained release preparation is from about 30 to about 90% (w/w), preferably from about 35 to about 80% (w/w), further preferably from about 40 to about 75% (w/w), the content of a swellable polymer is from about 3 to about 30% (w/w), preferably from about 3 to about 15% (w/w). The film agent may further contain a hydrophilic substance, and in which case, the content of a hydrophilic substance in the film agent is about 50% (w/w) or less, preferably about 5 to 40% (w/w), further preferably from about 5 to 35% (w/w). This % (w/w) indicates % by weight based on a film agent composition which is obtained by removing a solvent (e.g., water, lower alcohols such as methanol, ethanol and the like) from a film agent solution.

The sustained release preparation is produced by preparing a nucleus containing a drugs as exemplified below, then, coating the resulted nucleus with a film agent solution prepared by heat-solving a water-insoluble substance, swellable polymer and the like or by dissolving or dispersing it in a solvent.

I. Preparation of Nucleus Containing Drug

The form of nucleus containing a drug to be coated with a film agent (hereinafter, sometimes simply referred to as nucleus) is not particularly restricted, and preferably, the nucleus is formed into particles such as a granule or fine particle.

When the nucleus is composed of granules or fine particles, the average particle size thereof is preferably from about 150 to about 2000 μm, further preferably, from about 500 to about 1400 μm.

Preparation of the nucleus can be effected by a usual production method. For example, a suitable excipient, binding agent, disintegrating agent, lubricant, stabilizer and the like are mixed with a drug, and the mixture is subjected to a wet extrusion granulating method, fluidized bed granulating method or the like, to prepare a nucleus.

The content of drugs in a nucleus is from about 0.5 to about 95% (w/w), preferably from about 5.0 to about 80% (w/w), further preferably from about 30 to about 70% (w/w).

As the excipient contained in the nucleus, for example, saccharides such as sucrose, lactose, mannitol, glucose and the like, starch, crystalline cellulose, calcium phosphate, corn starch and the like are used. Among them, crystalline cellulose, corn starch are preferable.

As the binding agent, for example, polyvinyl alcohol, hydroxypropylcellulose, polyethylene glycol, polyvinyl pyrrolidone, Pluronic F68, gum Arabic, gelatin, starch and the like are used. As the disintegrating agent, for example, carboxymethylcellulose calcium (ECG505), croscarmelose sodium (Ac-Di-Sol), crosslinked polyvinylpyrrolidone (Crospovidone), low substituted hydroxypropylcellulose (L-HPC) and the like are used. Among them, hydroxypropylcellulose, polyvinylpyrrolidone, lower substituted hydroxypropylcellulose are preferable. As the lubricant and coagulation inhibitor, for example, talc, magnesium stearate and inorganic salts thereof are used, and as the lubricant, polyethylene glycol and the like are used. As the stabilizer, acids such as tartaric acid, citric acid, succinic acid, fumaric acid, maleic acid and the like, are used.

A nucleus can also be prepared by, in addition to the above-mentioned, for example, a rolling granulation method in which a drug or a mixture of a drug with an excipient, lubricant and the like are added portionwise onto an inert carrier particle which is the core of the nucleus while spraying a binder dissolved in a suitable solvent such as water, lower alcohol (e.g., methanol, ethanol and the like) and the like, a pan coating method, a fluidized bed coating method or a melt granulating method. As the inert carrier particle, for example, those made of sucrose, lactose, starch, crystalline cellulose or waxes can be used, and the average particle size thereof is preferably from about 100 μm to about 1500 μm.

For separating a drug contained in a nucleus and a film agent, the surface of the nucleus may be coated with a protective agent. As the protective agent, for example, the above-mentioned hydrophilic substances, water-insoluble substances and the like are used. As the protective agent, preferably polyethylene glycol, and polysaccharides having hydroxyalkyl or carboxyalkyl are used, more preferably, hydroxypropylmethylcellulose and hydroxypropylcellulose are used. The protective agent may contain, as stabilizer, acids such as tartaric acid, citric acid, succinic acid, fumaric acid, maleic acid and the like, and lubricants such as talc and the like. When the protective agent is used, the coating amount is from about 1 to about 15% (w/w), preferably from about 1 to about 10% (w/w), further preferably from about 2 to about 8% (w/w), based on the nucleus.

The protective agent can be coated by a usual coating method, and specifically, the protective agent can be coated by spray-coating the nucleus, for example, by a fluidized bed coating method, pan coating method and the like.

II. Coating of Nucleus with Film Agent

A nucleus obtained in the above-mentioned step I is coated with a film agent solution obtained by heat-solving the above-mentioned water-insoluble substance and pH-dependent swellable polymer, and a hydrophilic substance, or by dissolving or dispersing them in a solvent, to give a sustained release preparation.

As the method for coating a nucleus with a film agent solution, for example, a spray coating method and the like are listed.

The composition ratio of a water-insoluble substance, swellable polymer or hydrophilic substance in a film agent solution is appropriately selected so that the contents of these components in a coated film are the above-mentioned contents, respectively.

The coating amount of a film agent is from about 1 to about 90% (w/w), preferably from about 5 to about 50% (w/w), further preferably from about 5 to about 35% (w/w), based on a nucleus (not including coating amount of protective agent).

As the solvent in a film agent solution, water or an organic solvent can be used alone or in admixture thereof. In the case of use in admixture, the mixing ratio of water to an organic solvent (water/organic solvent: by weight) can be varied in the range from 1 to 100%, and is preferably from 1 to about 30%. The organic solvent is not particularly restricted providing it dissolves a water-insoluble substance, and for example, lower alcohols such as methyl alcohol, ethyl alcohol, isopropyl alcohol, n-butyl alcohol and the like, lower alkanone such as acetone and the like, acetonitrile, chloroform, methylene chloride and the like are used. Among them, lower alcohols are preferable, and ethyl alcohol and isopropyl alcohol are particularly preferable. Water, and a mixture of water with an organic solvent are preferably used as a solvent for a film agent. In this case, if necessary, an acid such as tartaric acid, citric acid, succinic acid, fumaric acid, maleic acid and the like may be added into a film agent solution for stabilizing the film agent solution.

An operation of coating by spray coating can be effected by a usual coating method, and specifically, it can be performed by spray-coating a film agent solution onto a nucleus by a fluidized bed coating method, pan coating method and the like. In this case, if necessary, talc, titanium oxide, magnesium stearate, calcium stearate, light anhydrous silicic acid and the like may also be added as a lubricant, and glycerin fatty acid ester, hydrogenated castor oil, triethyl citrate, cetyl alcohol, stearyl alcohol and the like may also be added as a plasticizer.

After coating with a film agent, if necessary, an antistatic agent such as talc and the like may be mixed.

The immediate-release preparation may be liquid (solution, suspension, emulsion and the like) or solid (particle, pill, tablet and the like). Oral agents and parenteral agents such as an injection and the like are used, and oral agents are preferable.

The immediate-release preparation, usually, may contain, in addition to an active component drug, also carriers, additives and excipients conventionally used in the production field (hereinafter, sometimes abbreviated as excipient). The preparation excipient to be used is not particularly restricted providing it is an excipient ordinarily used as a preparation excipient. For example, as the excipient for an oral solid preparation, lactose, starch, corn starch, crystalline cellulose (Avicel PH101, manufactured by Asahi Kasei Corporation, and the like), powder sugar, granulated sugar, mannitol, light anhydrous silicic acid, magnesium carbonate, calcium carbonate, L-cysteine and the like are used, and preferably, corn starch and mannitol and the like are used. These excipients can be used alone or in combination of two or more. The content of the excipient is, for example, from about 4.5 to about 99.4 w/w %, preferably from about 20 to about 98.5 w/w %, further preferably from about 30 to about 97 w/w %, based on the total amount of the immediate-release preparation.

The content of a drug in the immediate-release preparation can be appropriately selected in the range from about 0.5 to about 95%, preferably from about 1 to about 60% based on the total amount of the immediate-release preparation.

When the immediate-release preparation is an oral solid preparation, it usually contains, in addition to the above-mentioned components, also an additive. As this additive, for example, calcium carboxymethylcellulose (ECG-505, manufactured by Gotoku Yakuhin), croscarmelose sodium (e.g., Actisol, manufactured by Asahi Kasei Corporation), crospovidone (e.g., Kollidon CL, manufactured by BASF), low substituted hydroxypropylcellulose (manufactured by Shin-Etsu Chemical Co., Ltd.), carboxymethylstarch (manufactured by Matsutani Kagaku K.K.), sodium carboxymethylstarch (Exprotab, manufactured by Kimura Sangyo), partially pregelatinized starch (PCS, manufactured by Asahi Kasei Corporation), and the like are used, and for example, those which disintegrate a granule by adsorbing water in contact with water, causing swelling, or making a channel between an effective ingredient constituting the nucleus and an excipient, can be used. These disintegrating agents can be used alone or in combination of two or more. The amount of the disintegrating agent used is appropriately selected depending on the kind and blending amount of a drug used, design of releasing property, and the like, and for example, from about 0.05 to about 30 w/w %, preferably from about 0.5 to about 15 w/w %, based on the total amount of the quick releasing agent.

When the immediate-release preparation is an oral solid preparation, it may further contain, in addition to the above-mentioned composition in the case of the oral solid preparation, if desired, additives conventional in solid preparations. As such an additive, there are used, for example, a binder (e.g., sucrose, gelatin, gum Arabic powder, methylcellulose, hydroxypropylcellulose, hydroxypropylmethylcellulose, carboxymethylcellulose, polyvinylpyrrolidone, pullulan, dextrin and the like), a lubricant (e.g., polyethylene glycol, magnesium stearate, talc, light anhydrous silicic acid (e.g., Aerosil (Nippon Aerosil)), a surfactant (e.g., anionic surfactants such as sodium alkylsulfate and the like, nonionic surfactants such as polyoxyethylene fatty acid ester and polyoxyethylene sorbitan fatty acid ester, polyoxyethylene castor oil derivatives and the like), a colorant (e.g., tar coloring matter, caramel, iron oxide red, titanium oxide, riboflavins), if necessary, an appetizing agent (e.g., sweetening agent, flavoring agent and the like), an adsorbent, preservative, wetting agent, antistatic agent, and the like. Further, as the stabilizer, an organic acid such as tartaric acid, citric acid, succinic acid, fumaric acid and the like may also be added.

As the above-mentioned binder, hydroxypropylcellulose, polyethylene glycol and polyvinylpyrrolidone and the like are preferably used.

The immediate-release preparation can be prepared by, based on a usual technology of producing preparations, mixing the above-mentioned components, and if necessary, further kneading the mixture, and molding it. The above-mentioned mixing is conducted by generally used methods, for example, mixing, kneading and the like. Specifically, when a immediate-release preparation is formed, for example, into a particle, it can be prepared, according to the same means as in the above-mentioned method for preparing a nucleus of a sustained release preparation, by mixing the components using a vertical granulator, universal kneader (manufactured by Hata Tekkosho), fluidized bed granulator FD-5S (manufactured by Powrex Corporation), and the like, and then, granulating the mixture by a wet extrusion granulation method, fluidized bed granulation method and the like.

Thus obtained immediate-release preparation and sustained release preparation may be themselves made into products or made into products appropriately together with preparation excipients and the like, separately, by an ordinary method, then, may be administered simultaneously or may be administered in combination at any administration interval, or they may be themselves made into one oral preparation (e.g., granule, fine particle, tablet, capsule and the like) or made into one oral preparation appropriately together with preparation excipients and the like. It may also be permissible that they are made into granules or fine particles, and filled in the same capsule to be used as a preparation for oral administration.

[3] Sublingual, Buccal or Intraoral Quick Disintegrating Agent and Preparation Thereof Sublingual, buccal or intraoral quick disintegrating agents may be a solid preparation such as tablet and the like, or may be an oral mucosa membrane patch (film).

As the sublingual, buccal or intraoral quick disintegrating agent, a preparation containing the compound of the present invention or the concomitant drug and an excipient is preferable. It may contain also auxiliary agents such as a lubricant, isotonizing agent, hydrophilic carrier, water-dispersible polymer, stabilizer and the like. Further, for easy absorption and increased bioavailability, β-cyclodextrin or β-cyclodextrin derivatives (e.g., hydroxypropyl-β-cyclodextrin and the like) and the like may also be contained.

As the above-mentioned excipient, lactose, sucrose, D-mannitol, starch, crystalline cellulose, light anhydrous silicic acid and the like are listed. As the lubricant, magnesium stearate, calcium stearate, talc, colloidal silica and the like are listed, and particularly, magnesium stearate and colloidal silica are preferable. As the isotonizing agent, sodium chloride, glucose, fructose, mannitol, sorbitol, lactose, saccharose, glycerin, urea and the like are listed, and particularly, mannitol is preferable. As the hydrophilic carrier, swellable hydrophilic carriers such as crystalline cellulose, ethylcellulose, crosslinkable polyvinylpyrrolidone, light anhydrous silicic acid, silicic acid, dicalcium phosphate, calcium carbonate and the like are listed, and particularly, crystalline cellulose (e.g., crystalline cellulose and the like) is preferable. As the water-dispersible polymer, gums (e.g., gum tragacanth, acacia gum, guar gum), alginates (e.g., sodium alginate), cellulose derivatives (e.g., methylcellulose, carboxymethylcellulose, hydroxymethylcellulose, hydroxypropylcellulose, hydroxypropylmethylcellulose), gelatin, water-soluble starch, polyacrylic acids (e.g., Carbomer), polymethacrylic acid, polyvinyl alcohol, polyethylene glycol, polyvinylpyrrolidone, polycarbophil, ascorbate palmitates and the like are listed, and hydroxypropylmethylcellulose, polyacrylic acid, alginate, gelatin, carboxymethylcellulose, polyvinylpyrrolidone, polyethylene glycol and the like are preferable. Particularly, hydroxypropylmethylcellulose is preferable. As the stabilizer, cysteine, thiosorbitol, tartaric acid, citric acid, sodium carbonate, ascorbic acid, glycine, sodium sulfite and the like are listed, and particularly, citric acid and ascorbic acid are preferable.

The sublingual, buccal or intraoral quick disintegrating agent can be produced by mixing the compound of the present invention or the concomitant drug and an excipient by a method known per se. Further, if desired, the above-mentioned auxiliary agents such as a lubricant, isotonizing agent, hydrophilic carrier, water-dispersible polymer, stabilizer, colorant, sweetening agent, preservative and the like may be mixed. The sublingual, buccal or intraoral quick disintegrating agent is obtained by mixing the above-mentioned components simultaneously or at a time interval, then subjecting the mixture to tablet-making molding under pressure. For obtaining suitable hardness, it may also be permissible that the materials are moistened by using a solvent such as water, alcohol and the like if desired before and after the tablet making process, and after the molding, the materials are dried, to obtain a product.

In the case of molding into a mucosa membrane patch (film), the compound of the present invention or the concomitant drug and the above-mentioned water-dispersible polymer (preferably, hydroxypropylcellulose, hydroxypropylmethylcellulose), excipient and the like are dissolved in a solvent such as water and the like, and the resulted solution is cast to give a film. Further, additives such as a plasticizer, stabilizer, antioxidant, preservative, colorant, buffer, sweetening agent and the like may also be added. For imparting suitable elasticity to the film, glycols such as polyethylene glycol, propylene glycol and the like may be contained, or for enhancing adhesion of the film to an intraoral mucosa membrane lining, a bio-adhesive polymer (e.g., polycarbophil, carbopol) may also be contained. In the casting, a solution is poured on the non-adhesive surface, spread to uniform thickness (preferably, about 10 to 1000 micron) by an application tool such as a doctor blade and the like, then, the solution is dried to form a film. It may be advantageous that thus formed film is dried at room temperature or under heat, and cut into a desired area.

As the preferable intraoral quick disintegrating agent, there are listed solid quick scattering dose agents composed of a network body comprising the compound of the present invention or the concomitant drug, and a water-soluble or water-diffusible carrier which is inert to the compound of the present invention or concomitant drug, are listed. This network body is obtained by sublimating a solvent from the solid composition constituted of a solution prepared by dissolving the compound of the present invention or the concomitant drug in a suitable solvent.

It is preferable that the composition of an intraoral quick disintegrating agent contains a matrix forming agent and a secondary component, in addition to the compound of the present invention or the concomitant drug.

Examples of the matrix forming agent include animal proteins or vegetable proteins such as gelatins, dextrins, soybean, wheat and psyllium seed protein and the like; rubber substances such as gum Arabic, guar gum, agar, xanthane gum and the like; polysaccharides; alginic acids; carboxymethylcelluloses; carageenans; dextrans; pectines; synthetic polymers such as polyvinylpyrrolidone and the like; substances derived from a gelatin-gum Arabic complex, and the like. Further, saccharides such as mannitol, dextrose, lactose, galactose, trehalose and the like; cyclic saccharides such as cyclodextrin and the like; inorganic salts such as sodium phosphate, sodium chloride and aluminum silicate and the like; amino acids having 2 to 12 carbon atoms such as glycine, L-alanine, L-aspartic acid, L-glutamic acid, L-hydroxyproline, L-isoleucine, L-leucine, L-phenylalanine and the like, are contained.

One or more of the matrix forming agents can be introduced in a solution or suspension before solidification. Such as matrix forming agent may be present in addition to a surfactant, or may be present while a surfactant being excluded. The matrix forming agents aid to maintain the compound of the present invention or the concomitant drug in the solution or suspension in diffused condition, in addition to formation of the matrix.

The composition may contain secondary components such as a preservative, antioxidant, surfactant, thickening agent, colorant, pH controlling agent, flavoring agent, sweetening agent, food taste masking agent and the like. As the suitable colorant, there are listed red, black and yellow iron oxides, and FD & C dyes such as FD & C Blue 2, FD & C Red 40 and the like manufactured by Ellis and Everard. Examples of the suitable flavoring agent include mint, raspberry, licorice, orange, lemon, grapefruit, caramel, vanilla, cherry, grape flavor and combinations thereof. Examples of the suitable pH controlling agent include citric acid, tartaric acid, phosphoric acid, hydrochloric acid and maleic acid. Examples of the suitable sweetening agent include aspartame, acesulfame K and thaumatin and the like. Examples of the suitable food taste masking agent include sodium bicarbonate, ion exchange resin, cyclodextrin-inclusion compounds, adsorbent substances and microcapsulated apomorphine.

The preparation contains the compound of the present invention or the concomitant drug in an amount usually from about 0.1 to about 50% by weight, preferably from about 0.1 to about 30% by weight, and preferable are preparations (such as the above-mentioned sublingual agent, buccal and the like) which can dissolve 90% or more of the compound of the present invention or the concomitant drug (into water) within the time range of about 1 to about 60 min, preferably of about 1 to about 15 min, more preferably of about 2 to about 5 min, and intraoral quick disintegrating preparations which are disintegrated within the range of 1 to 60 sec, preferably of 1 to 30 sec, further preferably of 1 to 10 sec, after placed in an oral cavity.

The content of the above-mentioned excipient in the whole preparation is from about 10 to about 99% by weight, preferably from about 30 to about 90% by weight. The content of β-cyclodextrin or β-cyclodextrin derivative in the whole preparation is from 0 to about 30% by weight. The content of the lubricant in the whole preparation is from about 0.01 to about 10% by weight, preferably from about 1 to about 5% by weight. The content of the isotonizing agent in the whole preparation is from about 0.1 to about 90% by weight, preferably, from about 10 to about 70% by weight. The content of the hydrophilic carrier in the whole preparation is from about 0.1 to about 50% by weight, preferably, from about 10 to about 30% by weight. The content of the water-dispersible polymer in the whole preparation is from about 0.1 to about 30% by weight, preferably, from about 10 to about 25% by weight. The content of the stabilizer in the whole preparation is from about 0.1 to about 10% by weight, preferably, from about 1 to 5% by weight. The above-mentioned preparation may further contain additives such as a colorant, sweetening agent, preservative and the like, if necessary.

The dosage of a combination agent of the present invention differs depending on the kind of a compound of the present invention, age, body weight, condition, drug form, administration method, administration period and the like, and for example, for one prostate cancer patient (adult, body weight: about 60 kg), the combination agent is administered intravenously, at a dose of about 0.01 to about 1000 mg/kg/day, preferably about 0.01 to about 100 mg/kg/day, more preferably about 0.1 to about 100 mg/kg/day, particularly about 0.1 to about 50 mg/kg/day, especially about 1.5 to about 30 mg/kg/day, in terms of the compound of the present invention or the concomitant drug, respectively, once or several times in division a day. Of course, since the dose as described above varies depending on various conditions, amounts smaller than the above-mentioned dosage may sometimes be sufficient, further, amounts over that range sometimes have to be administered.

The amount of the concomitant drug can be set at any value unless side effects are problematical. The daily dosage in terms of the concomitant drug differs depending on the severity of the symptom, age, sex, body weight, sensitivity difference of the subject, administration period, interval, and nature, pharmacy, kind of the pharmaceutical preparation, kind of effective ingredient, and the like, and not particularly restricted, and the amount of a drug is, in the case of oral administration for example, usually from about 0.001 to 2000 mg, preferably from about 0.01 to 500 mg, further preferably from about 0.1 to 100 mg, per 1 kg of a mammal and this is usually administered once to 4-times in division a day.

In administration of a combination agent of the present invention, it may be permissible that the compound of the present invention is administered after the first administration of the concomitant drugs or vice versa, though they may be administered simultaneously. When administered at a time interval, the interval differs depending on the effective ingredient to be administered, drug form and administration method, and for example, when the concomitant drug is administered first, a method in which the compound of the present invention is administered within time range of from 1 min to 3 days, preferably from 10 min to 1 day, more preferably from 15 min to 1 hr after administration of the concomitant drug is exemplified. When the compound of the present invention is administered first, a method in which the concomitant drug is administered within time range of from 1 min to 1 day, preferably from 10 min to 6 hrs, more preferably from 15 min to 1 hr after administration of the compound of the present invention is exemplified.

In a preferable administration method, for example, the concomitant drug which has been molded into an oral administration preparation is administered orally at a daily dose of about 0.001 to 200 mg/kg, and about 15 min later, the compound of the present invention which has been molded into an oral administration preparation is administered orally at a daily dose of about 0.005 to 100 mg/kg.

Furthermore, the pharmaceutical composition or the concomitant drug of the present invention can be combined with a non-drug therapy such as (1) surgery, (2) hypertensive chemotherapy using angiotensin II etc., (3) gene therapy, (4) thermotherapy, (5) cryotherapy, (6) laser cauterization, (7) radiotherapy, and the like.

For example, by using the pharmaceutical composition of the present invention or the concomitant drug of the present invention before and after an operation and the like, or by using before and after a treatment combining two or three kinds thereof, effects of prevention of resistance expression, elongation of Disease-Free Survival, suppression of cancer metastasis or recurrence, apothanasia and the like can be obtained.

In addition, a treatment with the pharmaceutical composition of the present invention or the concomitant drug of the present invention can be combined with a supporting therapy [(i) administration of antibiotic (e.g., β-lactam such as pansporin and the like, macrolides such as clarithromycin and the like etc.) for complication with various infectious diseases, (ii) administration of high-calorie infusion, amino acid preparation or general vitamin preparation for malnutrition improvement, (iii) administration of morphine for pain mitigation, (iv) administration of medicament for ameliorating side effects such as nausea, vomiting, anorexia, diarrhea, leucopenia, thrombocytopenia, hemoglobin concentration decrease, hair loss, hepatopathy, renopathy, DIC, fever and the like, and (v) administration of medicament for suppressing multiple drug resistance of cancer etc.].

Specific examples of a medicament for such object, e.g., "antiemetic", include gastric motility enhancers such as 5-$HT_3$ antagonists (e.g., ondansetron, tropisetron hydrochloride, azasetron, ramosetron, granisetron, dolasetron mesylate, palonosetron and the like); NK1 receptor antagonists (e.g., sendide, CP-99994, CP-100263, CP-122721-1, CP-96345, FK224, RPR100893, NKP608, aprepitant (EMEND (trademark)) and the like; 5-$HT_4$ antagonists (e.g., domperidone, mosapride, metoclopramide and the like), and the like; gastrointestinal tract motility regulators such as trimebutine and the like; phenothiazine medicaments such as prochlorperazine maleate, promethazine, thiethylperazine and the like; tranquilizers such as haloperidol, chlorpromazine phenolphthalinate, diazepam, droperidol and the like; steroids such as dexamethasone, prednisolone, betamethasone, triamcinolone and the like; as well as dimethylhydrin acid, diphenhydramine, hyoscine, hyoscine hydrobromide, tetrabenazine and the like.

Preferably, the pharmaceutical composition of the present invention or the combination agent of the present invention is administered orally (including sustained-release preparations), intravenously (including boluses, infusions and clathrates), subcutaneously and intramuscularly (including boluses, infusions and sustained-release preparations), transdermally, intratumorally or proximally before or after the above-described treatment is conducted.

As a period for administration of the pharmaceutical composition of the present invention or the combination agent of the present invention before the surgery, etc., for example, it can be administrated once about 30 min to 24 hr before the surgery, etc., or in 1 to 3 cycles about 3 to 6 months before the surgery, etc. In this way, the surgery, etc. can be conducted easily because, for example, a cancer tissue can be reduced by administering the pharmaceutical composition of the present invention or the combination agent of the present invention before the surgery, and the like.

As a period for administration of the pharmaceutical composition of the present invention or the combination agent of the present invention after the surgery and the like, for example, it can be administrated repeatedly about 30 min to 24 hr after the surgery, and the like in a unit of several weeks to 3 months. In this way, the effect of the surgery and the like can be enhanced by administering the pharmaceutical composition of the present invention or the combination agent of the present invention after the surgery and the like.

EXAMPLES

The present invention is explained in detail in the following by referring to Reference Examples, Examples, Formulation Examples and Experimental Examples, which are not to be construed as limitative.

The elution by column chromatography in Reference Examples and Examples was performed under observation by TLC (Thin Layer Chromatography). In the observation by TLC, Kieselgel 60 $F_{254}$ plate manufactured by Merck was used as a TLC plate, the solvent used as an elution solvent in column chromatography was used as an eluent, and a UV detector was adopted as a detection method. The silica gel for the column used was also Kieselgel 60 $F_{254}$(70-230 mesh) manufactured by Merck. The NMR spectrum shows proton NMR, VARIAN Gemini-200 (200 MHz type spectrometer), VARIAN Mercury-300(300 MHz) or JMTCO 400/54(JEOL Ltd., 400 MHz) was used for the measurement with tetramethylsilane as the internal standard, and δ value is shown in ppm. The reaction using a microwave reaction apparatus was performed using Emrys Optimizer manufactured by Biotage Ltd.

The infrared absorption spectrum (IR) was measured using Paragon 1000 manufactured by PerkinElmer Inc.

The abbreviations used in the Reference Examples and Examples mean the following.
s: singlet
br: broad
d: doublet
t: triplet
q: quartet
dd: double doublet ddd: double double doublet
dt: double triplet
m: multiplet
J: coupling constant
Hz: hertz
THF: tetrahydrofuran
DMSO: dimethyl sulfoxide
DMF: N,N-dimethylformamide Reference Example 1 benzyl (2S,3S)-3-hydroxy-2-methylpyrrolidine-1-carboxylate

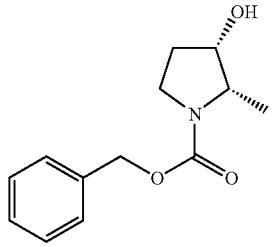

To a suspension (418 mL) of (4S,5S)-4-hydroxy-5-methylpyrrolidin-2-one (10.45 g) in dehydrated THF was added dropwise Red-Al (104.9 g: 363 mmol: 70% solution in toluene) under ice-cooling and a nitrogen stream. The mixture was stirred at room temperature for 20 min, and further refluxed for 3 hr. The reaction mixture was cooled again on ice, and sodium carbonate.10 hydrate (41.6 g) was added under a nitrogen stream. After stirring at room temperature overnight, insoluble material was filtered off through celite, and washed with THF. The filtrate and washing were combined and concentrated under reduced pressure to give (2S,3S)-3-hydroxy-2-methylpyrrolidine. The compound was not purified and diluted with DMSO to make 0.9 mol/L-DMSO solution. A solution (170 mL) of (2S,3S)-3-hydroxy-2-methylpyrrolidine in 0.9 mol/L-DMSO was diluted with water (200 mL), sodium hydrogen carbonate (24.6 g) and benzyl chloroformate (15 mL) were added, and the mixture was stirred at room temperature for 18 hr. Water was added to the reaction mixture, and the mixture was extracted with ethyl acetate. The extract was washed with saturated brine, dried over anhydrous sodium sulfate, and concentrated under reduced pressure to give the title compound as a pale-yellow oil (yield: 20.64 g, yield: 84%).

$^1$H-NMR(CDCl$_3$)δ: 1.10-1.30(3H,br), 1.60-2.20(3H,m), 3.40-4.40(5H,m), 7.20-7.40(5H,m).

Reference Example 2 benzyl (2S)-2-methyl-3-oxopyrrolidine-1-carboxylate

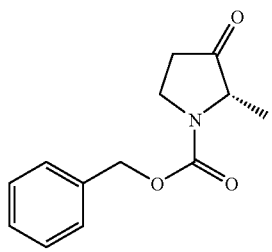

To a solution (150 mL) of benzyl (2S,3S)-3-hydroxy-2-methylpyrrolidine-1-carboxylate (20.5 g) in acetonitrile were added molecular sieves 4A powder (25 g) and 4-methylmorpholine-N-oxide (20.4 g), and the mixture was cooled to 0° C. tetra-n-Propylammonium perruthenate (3.0 g) was added, and the mixture was stirred at 0° C. for 1 hr and at room temperature for 18 hr. The reaction mixture was concentrated under reduced pressure, and the residue was suspended in ethyl acetate. The insoluble material was filtered through Hyflo Super-Cel. The filtrate was concentrated under reduced pressure, and the residue was purified by silica gel column chromatography (eluent: hexane/ethyl acetate=9/1→2/1) to give the title compound as a colorless oil (yield: 18.0 g, yield: 89%).

$^1$H-NMR(CDCl$_3$)δ: 1.34(3H,d,J=6.6 Hz), 2.50-2.70(2H,m), 3.60-3.75(1H,m), 3.90-4.10(2H,m), 5.15(1H,d,J=12.3 Hz), 5.20(1H,d,J=12.3 Hz), 7.30-7.40(5H,m).

Reference Example 3 benzyl (2S,3S)-3-hydroxy-2,3-dimethylpyrrolidine-1-carboxylate

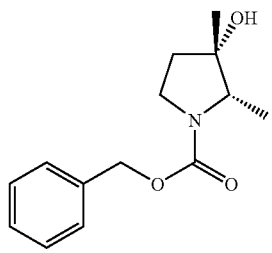

A suspension (300 mL) of cerium chloride (47 g) in THF was cooled to −78° C., and 3 mol/L methylmagnesium bromide-diethyl ether solution (56 mL) was added dropwise while adjusting the temperature of the solution to not higher than −70° C. After the completion of the dropwise addition, the mixture was stirred at −78° C. for 30 min, and a solution (60 mL) of benzyl (2S)-2-methyl-3-oxopyrrolidine-1-carboxylate (18 g) in THF was added dropwise while adjusting the temperature of the solution to not higher than −70° C. The reaction mixture was warmed to 0° C. over 2 hr, ethyl acetate (1 L) was added, and the insoluble material was filtered off. Water was added to the filtrate and then the mixture was partitioned. The organic layer was washed with saturated brine, dried over anhydrous sodium sulfate, and concentrated under reduced pressure. The residue was purified by silica gel column chromatography (eluent: hexane/ethyl acetate=9/1→1/1) to give the title compound as a colorless oil (yield: 16.2 g, yield: 84%).

$^1$H-NMR(CDCl$_3$)δ: 1.10-1.35(3H,br), 1.34(3H,s), 1.47(1H,s), 1.75-1.90(1H,m), 1.91-2.00(1H,m), 3.49(2H,t,J=7.2 Hz), 3.55-3.65(1H,m), 5.05-5.20(2H,m), 7.20-7.40(5H,m).

Reference Example 4

(2S,3S)-2,3-dimethylpyrrolidin-3-ol 0.5 oxalate

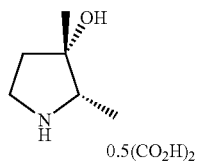

To a solution (200 mL) of benzyl (2S,3S)-3-hydroxy-2,3-dimethylpyrrolidine-1-carboxylate (16.1 g) in methanol was added 50% water containing-10% Pd/C (0.4 g), and the mixture was vigorously stirred under hydrogen atmosphere. The catalyst was filtered off, oxalic acid (2.90 g) was added to the filtrate and the mixture was concentrated under reduced pressure. The residual solid was suspended in ethyl acetate and filtered to give the title compound as a colorless solid (yield: 9.09 g, yield: 88%).

$^1$H-NMR(DMSO-$d_6$)δ: 1.05(3H,d,J=6.6 Hz), 1.18(3H,s), 1.74-1.86(2H,m), 2.80-2.95(2H,m), 2.98-3.10(1H,m), 4.00-5.20(3H,m).

Reference Example 5 benzyl (2S,3S)-3-ethyl-3-hydroxy-2-methylpyrrolidine-1-carboxylate

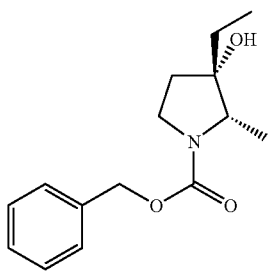

By an operation in the same manner as in Reference Example 3 and using cerium chloride (7.94 g), 3 mol/L ethylmagnesium bromide-diethyl ether solution (9.46 mL) and benzyl (2S)-2-methyl-3-oxopyrrolidine-1-carboxylate (3.0 g), the title compound was obtained as pale-yellow oil (yield: 1.96 g, yield: 58%).

$^1$H-NMR(CDCl$_3$)δ: 0.98(3H,t,J=7.5 Hz), 1.10-1.35(3H, br), 1.39(1H,s), 1.40-1.70(2H,m), 1.75-1.95(2H,m), 3.40-3.58(2H,m), 3.60-3.70(1H,m), 5.00-5.20(2H,m), 7.20-7.40 (5H,m).

Reference Example 6

(2S,3S)-3-ethyl-2-methylpyrrolidin-3-ol 0.5 oxalate

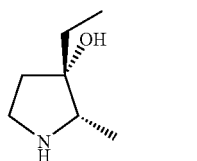

By an operation in the same manner as in Reference Example 4 and using benzyl (2S,3S)-3-ethyl-3-hydroxy-2-methylpyrrolidine-1-carboxylate (1.95 g) and 50% water containing-10% Pd/C (0.05 g), the title compound was obtained as a colorless solid (yield: 1.20 g, yield: 93%).

$^1$H-NMR(DMSO-$d_6$)δ: 0.91(3H,t,J=7.5 Hz), 1.07(3H,d, J=6.6 Hz), 1.30-1.45(1H,m), 1.46-1.60(1H,m), 1.78-1.83 (2H,m), 2.90-3.15(3H,m).

Reference Example 7 benzyl (2S,3S)-3-hydroxy-2-methyl-3-propylpyrrolidine-1-carboxylate

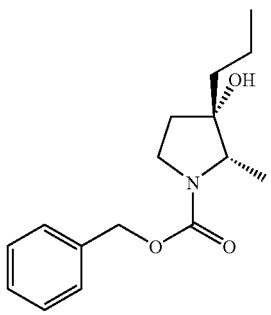

By an operation in the same manner as in Reference Example 3 and using cerium chloride (12.9 g), 2 mol/L propylmagnesium bromide—THF solution (20 mL) and benzyl (2S)-2-methyl-3-oxopyrrolidine-1-carboxylate (3.5 g), the title compound was obtained as pale-yellow oil (yield: 2.32 g, yield: 56%).

$^1$H-NMR(CDCl$_3$)δ: 0.90-1.00(3H,m), 1.10-1.35(3H,br), 1.30-1.70(5H,m), 1.75-1.95(2H,m), 3.40-3.70(3H,m), 5.00-5.20(2H,m), 7.20-7.40(5H,m).

Reference Example 8

(2S,3S)-2-methyl-3-propylpyrrolidin-3-ol 0.5 oxalate

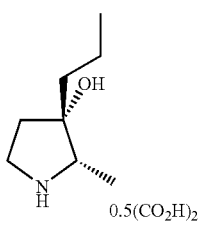

By an operation in the same manner as in Reference Example 4 and using benzyl (2S,3S)-3-hydroxy-2-methyl-3-propylpyrrolidine-1-carboxylate (2.32 g) and 50% water containing-10% Pd/C (0.10 g), the title compound was obtained as a colorless solid (yield: 1.50 g, yield: 96%).

$^1$H-NMR(DMSO-$d_6$)δ: 0.90(3H,t,J=6.6 Hz), 1.15(3H,d, J=6.6 Hz), 1.20-1.60(4H,m), 1.80-2.00(2H,m), 3.05-3.25 (3H,m).

Reference Example 9 benzyl (2S,3S)-3-hydroxy-2-methyl-3-(trifluoromethyl)pyrrolidine-1-carboxylate

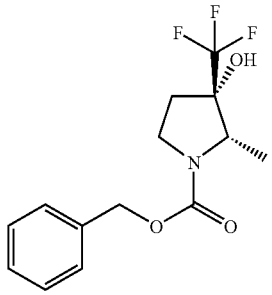

To a solution (10 mL) of benzyl (2S)-2-methyl-3-oxopyrrolidine-1-carboxylate (1.0 g) in THF were added trifluoromethyltrimethylsilane (0.95 mL) and 1 mol/L tetrabutylammonium fluoride—THF solution (0.43 mL) under ice-cooling, and the mixture was stirred at room temperature for 18 hr. A 1 mol/L tetrabutylammonium fluoride—THF solution (8.56 mL) was added to the reaction mixture, and the mixture was stirred at 50° C. for 1 hr. Water was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=9:1→2:1) to give the title compound as colorless oil (yield: 1.06 g, yield: 81%).

$^1$H-NMR(CDCl$_3$)δ: 1.20-1.40(3H,br), 1.95-2.05(1H,m), 2.17-2.35(1H,m), 3.45-3.56(1H,m), 3.66-3.80(1H,m), 4.10-4.25(1H,m), 5.05-5.20(2H,m), 7.20-7.40(5H,m).

Reference Example 10

(2S,3S)-2-methyl-3-(trifluoromethyl)pyrrolidin-3-ol 0.5 oxalate

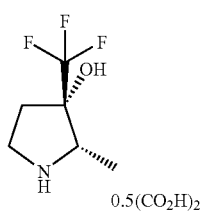

By an operation in the same manner as in Reference Example 4 and using benzyl (2S,3S)-3-hydroxy-2-methyl-3-(trifluoromethyl)pyrrolidine-1-carboxylate (1.05 g) and 50% water containing-10% Pd/C (0.05 g), the title compound was obtained as a colorless solid (yield: 0.65 g, yield: 88%).

$^1$H-NMR(DMSO-d$_6$)δ: 1.16(3H,d,J=6.6 Hz), 1.90-2.08 (1H,m), 2.15-2.30(1H,m), 2.95-3.05(1H,m), 3.10-3.20(1H, m), 3.34(1H,q,J=6.6 Hz), 6.00-7.00(1H,br).

Reference Example 11 benzyl (2S)-2-isopropyl-3-oxopyrrolidine-1-carboxylate

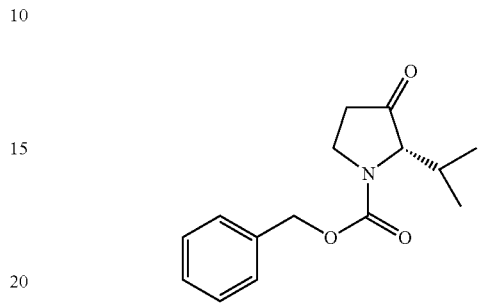

Under an argon atmosphere, a solution (315 mL) of diisopropylamine (31.2 g) in dehydrated THF was cooled to −10° C., 1.6 mol/L butyllithium-hexane solution (175.3 mL) was added at −5° C. or below, and the mixture was stirred at the same temperature for 30 min. Then the mixture was cooled to −78° C., and a solution (65 mL) of ethyl acetate (24.7 g) in dehydrated THF was added dropwise at −70° C. or below. After stirring at the same temperature for 1 hr, a solution (70 mL) of benzyl [(1S)-1-formyl-2-methylpropyl]carbamate (16.5 g) in dehydrated THF was added dropwise at −65° C. or below. After stirring at −70° C. for 1 hr, acetic acid (36 g) was added, and the mixture was warmed to 0° C. The reaction mixture was poured into ice water, the mixture was extracted with ethyl acetate, and the organic layer was washed with saturated brine, dried over anhydrous magnesium sulfate and concentrated. The residue was purified by silica gel column chromatography (eluent: hexane/ethyl acetate=19/1→3/2) to give ethyl (4S)-4-{[(benzyloxy)carbonyl]amino}-3-hydroxy-5-methylhexanoate as colorless oil (yield: 15.4 g).

Under an argon atmosphere, to a solution (228 mL) of ethyl (4S)-4-{[(benzyloxy)carbonyl]amino}-3-hydroxy-5-methylhexanoate (14.74 g) in dehydrated THF was added 2,6-lutidine (7.33 g) with stirring under ice-cooling, and tert-butyl dimethylsilyl trifluoromethanesulfonate (14.46 g) was added dropwise. The mixture was gradually warmed to room temperature and stirred for 1.5 hr. The reaction mixture was poured into ice water, and the mixture was extracted with ethyl acetate. The organic layer was washed with saturated brine, dried over anhydrous magnesium sulfate, and concentrated. The residue was purified by silica gel column chromatography (eluent: hexane/ethyl acetate=19/1→4/1) to give ethyl (4S)-4-{[(benzyloxy)carbonyl]amino}-3-{[tert-butyl (dimethyl)silyl]oxy}-5-methylhexanoate as colorless oil (yield: 17.7 g).

Under an argon atmosphere, to a suspension (303 mL) of ethyl (4S)-4-{[(benzyloxy)carbonyl]amino}-3-{[tert-butyl (dimethyl)silyl]oxy}-5-methylhexanoate (17.7 g), calcium chloride (6.73 g) and sodium borohydride (4.58 g) in dehydrated THF was added with stirring under ice-cooling dehydrated ethanol (152 mL), and the mixture was gradually warmed to room temperature and stirred for 15 hr. The reaction mixture was slowly poured into a mixture of ethyl acetate and ice water (containing 1 mol/L hydrochloric acid, 122 mL) and the mixture was partitioned. The organic layer was washed with saturated brine, dried over anhydrous magnesium sulfate, and concentrated. The residue was purified by silica gel column chromatography (eluent: hexane/ethyl acetate=19/1→1/1) to give benzyl ((1S)-2-{[tert-butyl(dimethyl)silyl]oxy}-4-hydroxy-1-isopropylbutyl)carbamate as colorless oil (yield: 14.9 g).

To a solution (188 mL) of benzyl ((1S)-2-{[tert-butyl(dimethyl)silyl]oxy}-4-hydroxy-1-isopropylbutyl)carbamate (14.9 g) in dehydrated THF was added triethylamine (5.07 g) and a solution (10 mL) of methanesulfonyl chloride (4.96 g) in dehydrated THF was added dropwise to the mixture under ice-cooling. After stirring at the same temperature for 1 hr, the reaction mixture was poured into a mixture of ethyl acetate and ice water and then the mixture was partitioned. The organic layer was washed with saturated brine, dried over anhydrous magnesium sulfate, and concentrated. To a solution (188 mL) of the residue in dehydrated THF was added with stirring under ice-cooling 1 mol/L potassium tert-butoxide—THF solution (37.7 mL), and the mixture was stirred at the same temperature for 1 hr. The reaction mixture was poured into a mixture of ethyl acetate and ice water and the mixture was partitioned. The organic layer was washed with saturated brine, dried over anhydrous magnesium sulfate, and concentrated. To a solution (188 mL) of the residue in dehydrated THF was added with stirring under ice-cooling 1 mol/L tetrabutylammonium fluoride—THF solution (37.7 mL), and the mixture was stirred at the same temperature for 1 hr and at room temperature for 5 hr. The reaction mixture was poured into a mixture of ethyl acetate and ice water and then the mixture was partitioned. The organic layer was washed with saturated brine, dried over anhydrous magnesium sulfate, and concentrated. The residue was purified by silica gel column chromatography (eluent: hexane-ethyl acetate/19/1→2/3) to give benzyl (2S)-3-hydroxy-2-isopropylpyrrolidine-1-carboxylate as colorless oil (yield: 3.22 g).

To a solution (26 mL) of benzyl (2S)-3-hydroxy-2-isopropylpyrrolidine-1-carboxylate (3.22 g) in dehydrating acetonitrile were added molecular sieves 4A powder (2.31 g) and 4-methylmorpholine-N-oxide (2.86 g), and the mixture was cooled to 0° C. tetra-n-Propylammonium perruthenate (0.16 g) was added, and the mixture was stirred at 0° C. for 1 hr and at room temperature for 18 hr. The reaction mixture was concentrated under reduced pressure, and the residue was suspended in ethyl acetate. The insoluble material was filtered through Hyflo Super-Cel. The filtrate was concentrated under reduced pressure, and the residue was purified by silica gel column chromatography (eluent: hexane-ethyl acetate=19:1→4:1) to give the title compound as colorless oil (yield: 2.74 g).

$^1$H-NMR(CDCl$_3$)δ: 0.93(3H,d,J=6.9 Hz), 1.02(3H,d,J=6.9 Hz), 2.14-2.39(1H,brs), 2.40-2.65(2H,m), 3.56-3.73 (1H,m), 3.89(1H,brs), 3.97-4.20(1H,brs), 5.17(2H,s), 7.36 (5H,brs).
IR(KBr):2963,1753,1703,1414 cm$^{-1}$.

Reference Example 12 benzyl (2S,3S)-3-hydroxy-2-isopropyl-3-methylpyrrolidine-1-carboxylate

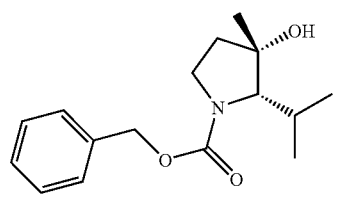

By an operation in the same manner as in Reference Example 3 and using cerium chloride (6.35 g), 3 mol/L methylmagnesium bromide-diethyl ether solution (7.55 mL) and benzyl (2S)-2-isopropyl-3-oxopyrrolidine-1-carboxylate (2.7 g), the title compound was obtained as pale-yellow oil (yield: 1.78 g, yield: 62%).

$^1$H-NMR(CDCl$_3$)δ: 0.87-1.13(6H,m), 1.34(3H,s), 1.62(1H,s), 1.76-1.89(1H,m), 1.99-2.09(2H,m), 3.34-3.54 (3H,m), 5.13(2H,s), 7.34(5H,brs).
IR(KBr):3432,2965,1682,1416 cm$^{-1}$.

Reference Example 13

(2S,3S)-2-isopropyl-3-methylpyrrolidin-3-ol 0.5 oxalate

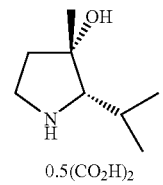

By an operation in the same manner as in Reference Example 4 and using benzyl (2S,3S)-3-hydroxy-2-isopropyl-3-methylpyrrolidine-1-carboxylate (1.78 g) and 50% water containing −10% Pd/C (0.09 g), the title compound was obtained as a colorless solid (yield: 1.07 g, yield: 89%).

$^1$H-NMR(DMSO-d$_6$+TFA)δ: 0.98(3H,d,J=6.6 Hz), 1.03 (3H,d,J=6.6 Hz), 1.37(3H,s), 1.91-1.97(2H,m), 2.00-2.12 (1H,m), 2.75-2.83(1H,m), 3.06-3.18(2H,m), 8.58(1H,brs), 9.32(1H,brs).

Reference Example 14 benzyl (2S,3S)-3-ethyl-3-hydroxy-2-isopropylpyrrolidine-1-carboxylate

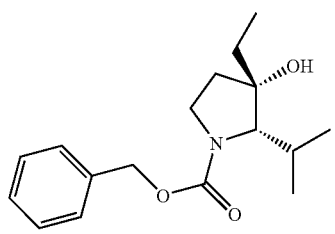

By an operation in the same manner as in Reference Example 3 and using cerium chloride (9.25 g), 3 mol/L ethylmagnesium bromide-diethyl ether solution (11.0 mL) and benzyl (2S)-2-isopropyl-3-oxopyrrolidine-1-carboxylate (3.92 g), the title compound was obtained as colorless oil (yield: 2.21 g, yield: 51%).

$^1$H-NMR(CDCl$_3$)δ: 0.92-1.10(9H,m), 1.43(1H,s), 1.50-1.60(2H,m), 1.91-2.14(3H,m), 3.30-3.60(3H,m), 5.12(2H,s), 7.34(5H,brs).

IR(KBr):3434,2963,1680,1416 cm$^{-1}$.

Reference Example 15

(2S,3S)-3-ethyl-2-isopropylpyrrolidin-3-ol 0.5 oxalate

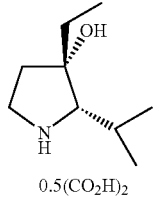

0.5(CO$_2$H)$_2$

By an operation in the same manner as in Reference Example 4 and using benzyl (2S,3S)-3-ethyl-3-hydroxy-2-isopropylpyrrolidine-1-carboxylate (2.2 g) and 50% water containing-10% Pd/C (0.11 g), the title compound was obtained as a colorless solid (yield: 1.33 g, yield: 83%).

$^1$H-NMR(DMSO-d$_6$+TFA)δ: 0.92(3H,t,J=7.2 Hz), 0.99 (3H,d,J=6.6 Hz), 1.01(3H,d,J=6.6 Hz), 1.49-1.61(1H,m), 1.70-1.80(1H,m), 1.88-1.95(2H,m), 1.99-2.13(1H,m), 2.78-2.86(1H,m), 3.06-3.20(2H,m), 8.55(1H,brs), 9.18(1H,brs).

Reference Example 16 benzyl (2S,3R)-3-cyclopropyl-3-hydroxy-2-isopropylpyrrolidine-1-carboxylate

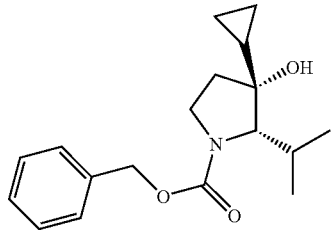

By an operation in the same manner as in Reference Example 3 and using cerium chloride (7.40 g), 0.5 mol/L cyclopropylmagnesium bromide—THF solution (52.8 mL) and benzyl (2S)-2-isopropyl-3-oxopyrrolidine-1-carboxylate (3.14 g), the title compound was obtained as colorless oil (yield: 2.31 g, yield: 63%).

$^1$H-NMR(CDCl$_3$)δ: 0.32-0.47(4H,m), 0.92-1.08(7H,m), 1.29(1H,s), 1.84-1.92(1H,m), 1.95-2.12(2H,br), 3.35-3.62 (3H,m), 5.14(2H,s), 7.34(5H,brs).

IR(KBr):3414,2959,1680,1416 cm$^{-1}$.

Reference Example 17

(2S,3R)-3-cyclopropyl-2-isopropylpyrrolidin-3-ol 0.5 oxalate

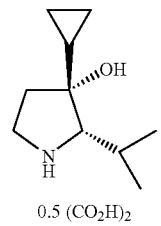

0.5 (CO$_2$H)$_2$

By an operation in the same manner as in Reference Example 4 and using benzyl (2S,3S)-3-cyclopropyl-3-hydroxy-2-isopropylpyrrolidine-1-carboxylate (1.98 g) and 50% water containing-10% Pd/C (0.10 g), the title compound was obtained as a colorless solid (yield: 1.22 g, yield: 88%).

$^1$H-NMR(DMSO-d$_6$+TFA)δ: 0.34-0.45(3H,m), 0.50-0.57 (1H,m), 0.93-1.03(1H,m), 0.99(3H,d,J=6.6 Hz), 1.08(3H,d, J=6.6 Hz), 1.75-1.97(2H,m), 2.00-2.12(1H,m), 2.87-2.95 (1H,m), 3.06-3.18(2H,m), 8.58(1H,brs), 9.22(1H,brs).

Reference Example 18 benzyl (2S,3R)-3-cyclopropyl-3-hydroxy-2-methylpyrrolidine-1-carboxylate

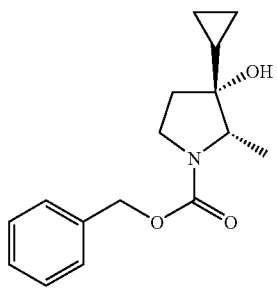

By an operation in the same manner as in Reference Example 3 and using cerium chloride (11.1 g), 0.5 mol/L cyclopropylmagnesium bromide—THF solution (72.0 mL) and benzyl (2S)-2-methyl-3-oxopyrrolidine-1-carboxylate (3.0 g), the title compound was obtained as colorless oil (yield: 1.64 g, yield: 46%).

$^1$H-NMR(CDCl$_3$)δ: 0.28-0.57(4H,m), 0.92-1.10(1H,m), 1.16-1.36(4H,m), 1.74-1.89(2H,m), 3.41-3.75(3H,m), 5.04-5.23(2H,m), 7.28-7.43(5H,m).

Reference Example 19 tert-butyl (2S,3S)-3-hydroxy-2-methylpyrrolidine-1-carboxylate

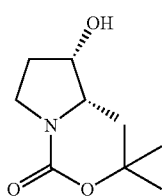

A solution (150 mL) of (2S,3S)-3-hydroxy-2-methylpyrrolidine (69 mmol) in THF was diluted with water (70 mL), and sodium carbonate (14.83 g) and di-tert-butyl bicarbonate (17.43 mL) were added, and the mixture was stirred at room temperature for 24 hr. The reaction mixture was partitioned between ethyl acetate and water, and the organic layer was dried over anhydrous magnesium sulfate and concentrated under reduced pressure. The residue was purified by silica gel column chromatography (eluent: hexane/ethyl acetate=3/1→1/3) to give the title compound as pale-yellow oil (yield: 11.09 g, yield: 80%).

$^1$H-NMR(CDCl$_3$)δ: 1.15-1.22(3H,m), 1.47(9H,s), 1.56-1.63(1H,m), 1.77-1.93(1H,m), 1.96-2.11(1H,m), 3.28-3.54(2H,m), 3.76-3.96(1H,m), 4.26-4.37(1H,m).

Reference Example 20 tert-butyl (2S)-2-methyl-3-oxopyrrolidine-1-carboxylate

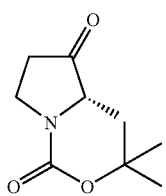

To a solution (75 mL) of (2S,3S)-3-hydroxy-2-methylpyrrolidine-1-carboxylate tert-butyl (9.04 g) in dehydrated acetonitrile were added molecular sieves 4A powder (11.5 g) and 4-methylmorpholine-N-oxide (10.5 g), and the mixture was cooled to 0° C. tetra-n-Propylammonium perruthenate (0.80 g) was added, and the mixture was stirred at room temperature for 4.5 hr. The reaction mixture was concentrated under reduced pressure, and the residue was suspended in ethyl acetate. The insoluble material was filtered through Hyflo Super-Cel. The filtrate was concentrated under reduced pressure, and the residue was purified by silica gel column chromatography (eluent: hexane/ethyl acetate=15/1→1/1) to give the title compound as colorless oil (yield: 7.67 g, yield: 85.7%).

$^1$H-NMR(CDCl$_3$)δ: 1.32(3H,d,J=7.2 Hz), 1.50(9H,s), 2.47-2.67(2H,m), 3.50-3.65(1H,m), 3.82-4.00(2H,m).

Reference Example 21 tert-butyl (2S,3R)-3-hydroxy-2-methyl-3-vinylpyrrolidine-1-carboxylate

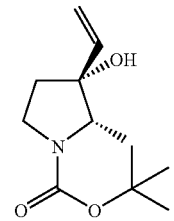

By an operation in the same manner as in Reference Example 3 and using cerium chloride (3.95 g), 1 mol/L vinyl-magnesium bromide—THF solution (12.5 mL) and tert-butyl (2S)-2-methyl-3-oxopyrrolidine-1-carboxylate (1.0 g), the title compound was obtained as colorless oil (yield: 0.648 g, yield: 57%).

$^1$H-NMR(CDCl$_3$)δ: 1.21(3H,d,J=6.4 Hz), 1.42-1.51(1H,m), 1.48(9H,s), 1.84-1.97(2H,m), 3.39-3.54(1H,m), 3.44-3.60(1H,m), 3.58-3.71(1H,m), 5.19(1H,dd,J=10.7, 1.0 Hz), 5.36(1H,dd,J=17.3, 1.0 Hz), 5.94(1H,dd,J=17.3, 10.7 Hz).

Reference Example 22 benzyl (2S)-2-ethyl-3-oxopyrrolidine-1-carboxylate

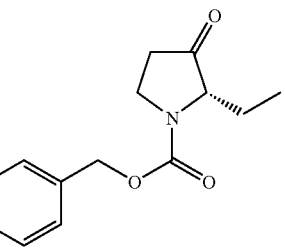

By an operation in the same manner as in Reference Example 11 and using benzyl [(1S)-1-formylpropyl]carbamate, the title compound was obtained as colorless oil.

$^1$H-NMR(CDCl$_3$)δ: 0.85(3H,t,J=7.6 Hz), 1.75-2.06(2H,m), 2.39-2.73(2H,m), 3.55-3.73(1H,m), 3.91-4.13(2H,m), 5.11-5.26(2H,m), 7.26-7.47(5H,m).

Reference Example 23 benzyl (2S,3S)-2-ethyl-3-hydroxy-3-methylpyrrolidine-1-carboxylate

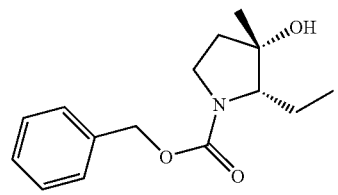

By an operation in the same manner as in Reference Example 3 and using cerium chloride (11.69 g), 3 mol/L methylmagnesium bromide-diethyl ether solution (13.55 mL) and benzyl (2S)-2-ethyl-3-oxopyrrolidine-1-carboxylate (3.35 g), the title compound was obtained as colorless oil (yield: 2.84 g, yield: 84%).

$^1$H-NMR(CDCl$_3$)δ: 0.88-1.07(3H,m), 1.36(3H,s), 1.42(1H,s), 1.47-1.90(3H,m), 1.91-2.07(1H,m), 3.34-3.58 (3H,m), 5.07-5.19(2H,m), 7.27-7.40(5H,m).

Reference Example 24

(2S,3S)-2-ethyl-3-methylpyrrolidin-3-ol 0.5 oxalate

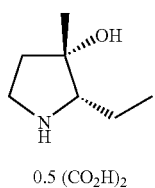

0.5 (CO$_2$H)$_2$

By an operation in the same manner as in Reference Example 4 and using benzyl (2S,3S)-2-ethyl-3-hydroxy-3-methylpyrrolidine-1-carboxylate (2.84 g) and 50% water containing-10% Pd/C (0.31 g), the title compound was obtained as a colorless solid (yield: 1.77 g, yield: 88%).

$^1$H-NMR(DMSO-d$_6$)δ: 0.82-1.02(4H,m), 1.24(3H,s), 1.38-1.76(2H,m), 1.81-1.97(2H,m), 2.81-2.91(1H,m), 3.01-3.20(2H,m), 4.94-6.34(1H,m).

Reference Example 25 benzyl (2S,3S)-2,3-diethyl-3-hydroxypyrrolidine-1-carboxylate

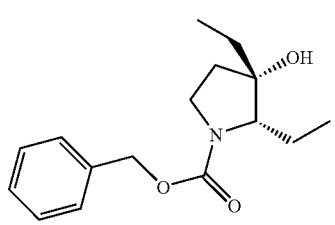

By an operation in the same manner as in Reference Example 3 and using cerium chloride (8.58 g), 3 mol/L ethylmagnesium bromide—diethyl ether solution (9.6 mL) and benzyl (2S)-2-ethyl-3-oxopyrrolidine-1-carboxylate (2.37 g), the title compound was obtained as colorless oil (yield: 2.19 g, yield: 82%).

$^1$H-NMR(CDCl$_3$)δ: 0.96(6H,t,J=7.4 Hz), 1.28-1.71(4H, m), 1.66-1.86(1H,m), 1.84-1.96(2H,m), 3.35-3.51(2H,m), 3.50-3.67(1H,m), 5.02-5.21(2H,m), 7.27-7.42(5H,m).

Reference Example 26

(2S,3S)-2,3-diethylpyrrolidin-3-ol 0.5 oxalate

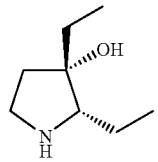

0.5 (CO$_2$H)$_2$

By an operation in the same manner as in Reference Example 4 and using benzyl (2S,3S)-2,3-diethyl-3-hydroxy-pyrrolidine-1-carboxylate (2.19 g) and 50% water containing-10% Pd/C (0.22 g), the title compound was obtained as a colorless solid (yield: 1.40 g, yield: 94%).

$^1$H-NMR(DMSO-d$_6$)δ: 0.80-1.01(6H,m), 1.27-1.66(5H, m), 1.74-1.88(2H,m), 2.69-2.84(1H,m), 2.90-3.14(2H,m), 4.57-5.31(1H,m).

Reference Example 27 benzyl (2S,3R)-3-cyclopropyl-2-ethyl-3-hydroxypyrrolidine-1-carboxylate

By an operation in the same manner as in Reference Example 3 and using cerium chloride (8.64 g), 0.5 mol/L cyclopropylmagnesium bromide—THF solution (58.0 mL) and benzyl (2S)-2-ethyl-3-oxopyrrolidine-1-carboxylate (2.37 g), the title compound was obtained as colorless oil (yield: 2.01 g, yield: 73%).

$^1$H-NMR(CDCl$_3$)δ: 0.29-0.53(4H,m), 0.86-1.14(4H,m), 1.20-1.32(1H,m), 1.49-1.73(1H,m), 1.65-1.85(1H,m), 1.80-2.00(2H,m), 3.36-3.60(3H,m), 5.05-5.22(2H,m), 7.26-7.43 (5H,m).

Reference Example 28

(2S,3R)-3-cyclopropyl-2-ethylpyrrolidin-3-ol 0.5 oxalate

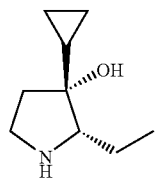

0.5 (CO$_2$H)$_2$

By an operation in the same manner as in Reference Example 4 and using benzyl (2S,3R)-3-cyclopropyl-2-ethyl-3-hydroxypyrrolidine-1-carboxylate (2.01 g) and 50% water containing-10% Pd/C (0.20 g), the title compound was obtained as a colorless solid (yield: 1.35 g, yield: 96%).

$^1$H-NMR(DMSO-d$_6$+TFA)δ: 0.22-0.51(4H,m), 0.79-1.10 (4H,m), 1.49-2.01(4H,m), 3.00-3.26(3H,m), 8.63(1H,brs), 9.16(1H,brs).

Reference Example 29 ethyl 4-{[(benzyloxy)carbonyl]amino}-2,2-dimethyl-3-hydroxypentanoate

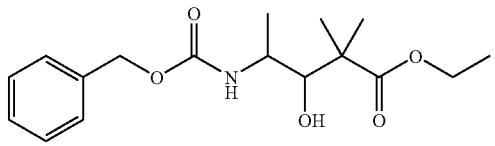

To a solution (100 mL) of ethyl 4-{[(benzyloxy)carbonyl]amino}-2,2-dimethyl-3-oxopentanoate (5.76 g) in methanol was added sodium borohydride (940 mg) at 0° C., and the mixture was stirred at room temperature for 17 hr. Saturated aqueous ammonium chloride solution was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=50/1→1/3) to give the title compound as a colorless solid (yield: 4.26 g, yield: 74%).

$^1$H-NMR(CDCl$_3$)δ: 1.01(3H,d,J=6.8 Hz), 1.12-1.40(10H, m), 3.39-3.64(1H,m), 3.76-4.24(3H,m), 4.85-5.33(3H,m), 7.22-7.42(5H,m).

Reference Example 30 ethyl 4-{[(benzyloxy)carbonyl]amino}-2,2-dimethyl-3-(tert-butyldimethylsilyloxy)pentanoate

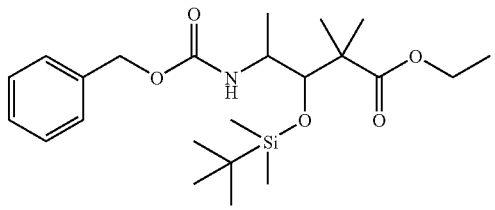

To a solution (80 mL) of ethyl 4-{[(benzyloxy)carbonyl]amino}-2,2-dimethyl-3-hydroxypentanoate (5.7 g) and 2,6-lutidine (2.27 mL) in THF was added under ice-cooling tert-butyldimethylsilyl trifluoromethanesulfonate (3.44 mL), and the mixture was warmed to room temperature and stirred for 17 hr. The reaction mixture was added to water, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=50/1→2/1) to give the title compound as colorless oil (yield: 5.42 g, yield: 70%).

$^1$H-NMR(CDCl$_3$)δ: 0.03-0.20(6H,m), 0.88-0.95(9H,m), 1.06-1.33(12H,m), 3.73-4.19(4H,m), 4.55-5.22(3H,m), 7.26-7.41(5H,m).

Reference Example 31 benzyl [2-(tert-butyldimethylsilyloxy)-4-hydroxy-1,3,3-trimethylbutyl]carbamate

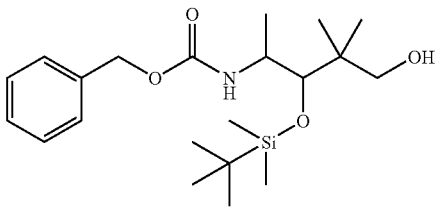

To a mixed solution of ethyl 4-{[(benzyloxy)carbonyl]amino}-2,2-dimethyl-3-(tert-butyldimethylsilyloxy)pentanoate (5.42 g) and calcium chloride (2.06 g) in THF (50 mL)-ethanol (25 mL) was added sodium borohydride (1.56 g) and the mixture was stirred at room temperature for 13 hr. The reaction mixture was added to water, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=50/1→1/1) to give the title compound as a colorless solid (yield: 1.38 g, yield: 28%).

$^1$H-NMR(CDCl$_3$)δ: 0.04-0.06(6H,m), 0.86(3H,s), 0.93(9H,s), 0.98(3H,s), 1.14(3H,d,J=6.8 Hz), 3.34-3.46(1H, m), 3.50-3.66(2H,m), 3.77-3.82(1H,m), 3.92-4.03(1H,m), 4.68-4.80(1H,m), 5.03-5.17(2H,m), 7.28-7.42(5H,m).

Reference Example 32 benzyl (2RS,3SR)-3-hydroxy-2,4,4-trimethylpyrrolidine-1-carboxylate

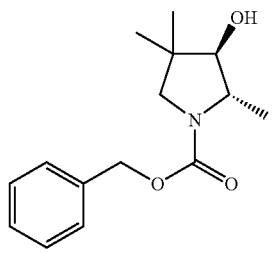

A solution (20 mL) of benzyl [2-(tert-butyldimethylsilyloxy)-4-hydroxy-1,3,3-trimethylbutyl]carbamate (1.38 g) and triethylamine (0.73 mL) in THF was added mesyl chloride (0.352 mL) at 0° C., and the mixture was stirred at 0° C. for 45 min. The reaction mixture was added to water, and the mixture was extracted with ethyl acetate. The extract was washed with saturated brine, dried over anhydrous magnesium sulfate, and concentrated under reduced pressure. To a solution (20 mL) of the residue in THF was added 1M potassium tert-butoxide—THF solution (3.8 mL). After stirring at room temperature for 1 hr, water was added and the mixture was extracted with ethyl acetate. The extract was washed with saturated brine, dried over anhydrous magnesium sulfate, and concentrated under reduced pressure. To a solution (10 mL) of the residue in THF was added 1M tetrabutylammonium fluoride—THF solution (4 mL), and the mixture was stirred at room temperature for 17 hr. The reaction mixture was added to water, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=50/1→1/2) to give the title compound as a colorless solid (yield: 842 mg, yield: 92%).

$^1$H-NMR(CDCl$_3$)δ: 0.96(3H,s), 1.06(3H,s), 1.32-1.48 (1H,m), 3.01-3.15(1H,m), 3.40-3.61(3H,m), 5.07-5.20(2H, m), 7.26-7.40(5H,m).

Reference Example 33

(2RS,3SR)-2,4,4-trimethylpyrrolidin-3-ol 0.5 oxalate

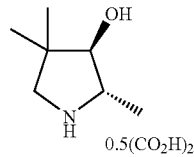

A suspension (20 mL) of benzyl (2RS,3SR)-3-hydroxy-2, 4,4-trimethylpyrrolidine-1-carboxylate (842 mg) and 10% palladium carbon (50% water-containing, 110 mg) in methanol was stirred under a hydrogen atmosphere for 1.5 hr. The reaction mixture was filtered, oxalic acid (144 mg) was added to the filtrate, and the mixture was concentrated under reduced pressure to give the title compound as a colorless solid (yield: 512 mg, yield: 92%).

$^1$H-NMR(d$_6$-DMSO+TFA)δ: 0.92(3H,s), 1.03(3H,s), 1.31 (3H,d,J=6.8 Hz), 2.88-3.11(2H,m), 3.12-3.33(1H,m), 3.40 (1H,d,J=9.1 Hz), 8.49(1H,brs), 9.05(1H,brs).

Reference Example 34 benzyl (2S,3S,5R)-3-hydroxy-2,5-dimethylpyrrolidine-1-carboxylate

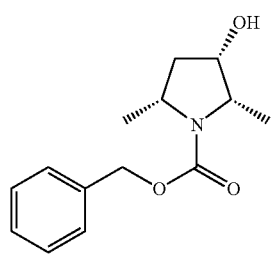

To a solution (12 mL) of benzyl (2S,3S,5S)-3-hydroxy-2-methyl-5-[(trimethylsilyl)methyl]pyrrolidine-1-carboxylate (222 mg) synthesized according to the method described in Journal of Organic Chemistry, vol. 59, pages 1958-1960 (1994), potassium tert-butoxide (130 mg) and 18-crown-6-ether (53 mg) in DMSO was added water (0.6 mL), and the mixture was stirred at 100° C. for 17 hr. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=50/1→2/3) to give the title compound as colorless oil (yield: 112 mg, yield: 65%).

$^1$H-NMR(CDCl$_3$)δ: 1.23(3H,d,J=6.4 Hz), 1.35(3H,d, J=6.1 Hz), 1.52-1.73(1H,m), 2.25-2.40(1H,m), 3.79-3.94 (1H,m), 3.95-4.10(1H,m), 4.22-4.36(1H,m), 5.06-5.19(2H, m), 7.26-7.42(5H,m).

Reference Example 35

(2S,3S,5R)-2,5-dimethylpyrrolidin-3-ol 0.5 oxalate

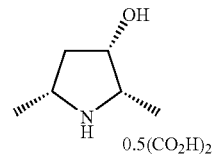

By an operation in the same manner as in Reference Example 33 and using benzyl (2S,3S,5R)-3-hydroxy-2,5-dimethylpyrrolidine-1-carboxylate (785 mg), 10% palladium carbon (50% water-containing, 80 mg) and oxalic acid (142 mg), the title compound was obtained as a colorless solid (yield: 485 mg, yield: 96%).

$^1$H-NMR(d$_6$-DMSO+TFA)δ: 1.16-1.40(1H,m), 1.22(3H, d,J=6.8 Hz), 1.32(3H,d,J=6.8 Hz), 1.42-1.57(1H,m), 2.33-2.52(1H,m), 3.28-3.47(1H,m), 3.46-3.66(1H,m), 4.05-4.22 (1H,m), 8.21(1H,brs), 9.13(1H,brs).

Reference Example 36 benzyl (2S,5R)-2,5-dimethyl-3-oxopyrrolidine-1-carboxylate

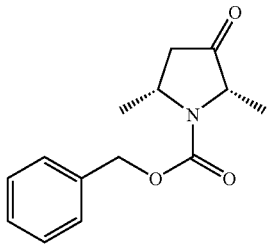

To a solution (20 mL) of benzyl (2S,3S,5R)-3-hydroxy-2, 5-dimethylpyrrolidine-1-carboxylate (1.30 g) in acetonitrile were added tetrapropylammonium perruthenate (92 mg), 4-methylmorpholine N-oxide (1.22 g) and molecular sieves 4A powder (1.32 g), and the mixture was stirred at room temperature for 2 hr. The reaction mixture was concentrated, the residue was suspended in ethyl acetate and filtered through celite. The filtrate was concentrated under reduced pressure, and the residue was purified by silica gel column chromatography (eluent: hexane/ethyl acetate=30/1→1/1) to give the title compound as colorless oil (yield: 1.30 g, yield: 100%).

$^1$H-NMR(CDCl$_3$)δ: 1.30(3H,d,J=6.6 Hz), 1.39(3H,d, J=7.0 Hz), 2.18-2.32(1H,m), 2.77-2.92(1H,m), 3.96-4.10 (1H,m), 4.41-4.55(1H,m), 5.15-5.25(2H,m), 7.29-7.42(5H, m).

Reference Example 37 benzyl (2S,3S,5R)-3-hydroxy-2,3,5-trimethylpyrrolidine-1-carboxylate

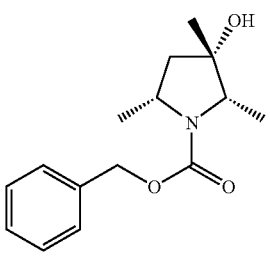

A suspension (8 mL) of cerium chloride (2.09 g) in THF was cooled to −78° C., and 1M methylmagnesium bromide— THF solution (7.2 mL) was added dropwise. The reaction mixture was stirred at −78° C. for 30 min and a solution (4 mL) of benzyl (2S,3S,5R)-2,5-dimethyl-3-oxopyrrolidine-1-carboxylate (600 mg) in THF was added dropwise. After the completion of the dropwise addition, the reaction mixture was warmed to room temperature over 2.5 hr. 1M Hydrochloric acid was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=50/1→1/1) to give the title compound as a colorless oil (yield: 450 mg, yield: 70%).

$^1$H-NMR(CDCl$_3$)δ: 1.24(3H,d,J=6.6 Hz), 1.31(3H,s), 1.34(3H,d,J=6.2 Hz), 1.36-1.49(1H,m), 1.7(1H,dd,J=12.7, 7.4 Hz), 1.98-2.12(1H,m), 3.58-3.75(1H,m), 3.76-3.92(1H, m), 5.03-5.23(2H,m), 7.27-7.43(5H,m).

Example 1

2-fluoro-4-[(2S,3S)-3-hydroxy-2,3-dimethylpyrrolidin-1-yl]benzonitrile

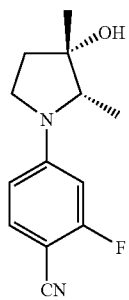

A solution (2 mL) of (2S,3S)-2,3-dimethylpyrrolidin-3-ol 0.5 oxalate (228 mg), 2,4-difluorobenzonitrile (292 mg) and lithium carbonate (206 mg) in DMSO was stirred at 80° C. for 18 hr. Water was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=9:1→2:1) and recrystallized from hexane-isopropyl ether to give the title compound as a colorless solid (yield: 188 mg, yield: 57%).

$^1$H-NMR(CDCl$_3$)δ: 1.21(3H,d,J=6.6 Hz), 1.37(3H,s), 1.59(1H,s), 1.95-2.04(1H,m), 2.14-2.26(1H,m), 6.23(1H,dd, J=12.9, 2.1 Hz), 6.31(1H,dd,J=8.7, 2.1 Hz), 7.35(1H,dd, J=8.7, 7.8 Hz).
IR(KBr):3324,2973,2209,1609 cm$^{-1}$.
mp:103-104° C.

Example 2

2-fluoro-4-[(2S,3S)-3-hydroxy-2,3-dimethylpyrrolidin-1-yl]-3-methylbenzonitrile

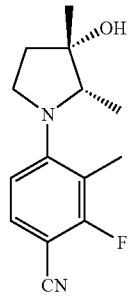

By an operation in the same manner as in Example 1 and using (2S,3S)-2,3-dimethylpyrrolidin-3-ol 0.5 oxalate (228 mg), 2,4-difluoro-3-methylbenzonitrile (321 mg) and lithium carbonate (206 mg), the title compound was obtained as a colorless solid (yield: 194 mg, yield: 56%).

$^1$H-NMR(CDCl$_3$)δ: 1.08(3H,d,J=6.3 Hz), 1.41(3H,s), 1.66(1H,s), 1.84-2.02(2H,m), 2.19(3H,d,J=2.4 Hz), 2.95(1H, dt,J=9.6, 2.1 Hz), 3.50(1H,q,J=6.3 Hz), 3.85-3.95(1H,m), 6.60(1H,d,J=8.6 Hz), 7.30(1H,t,J=8.6 Hz).
IR(KBr):3470,2976,2224,1613 cm$^{-1}$.
mp:68-69° C.

Example 3

4-[(2S,3S)-3-hydroxy-2,3-dimethylpyrrolidin-1-yl]-3-(trifluoromethyl)benzonitrile

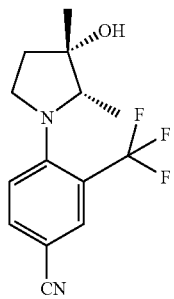

By an operation in the same manner as in Example 1 and using (2S,3S)-2,3-dimethylpyrrolidin-3-ol 0.5 oxalate (228 mg), 4-fluoro-3-(trifluoromethyl)benzonitrile (397 mg) and lithium carbonate (206 mg), the title compound was obtained as a colorless oil (yield: 220 mg, yield: 55%).

$^1$H-NMR(CDCl$_3$)δ: 1.09(3H,d,J=6.0 Hz), 1.40(3H,s), 1.71(1H,s), 1.85-2.08(2H,m), 3.10-3.20(1H,m), 3.53(1H,q, J=6.3 Hz), 3.80-3.95(1H,m), 7.02(1H,d,J=8.7 Hz), 7.61(1H, dd,J=8.7, 2.0 Hz), 7.87(1H,d,J=2.0 Hz).

IR(KBr):3441,2975,2222,1615 cm$^{-1}$.

Example 4

4-[(2S,3S)-3-hydroxy-2,3-dimethylpyrrolidin-1-yl]-2-methoxybenzonitrile

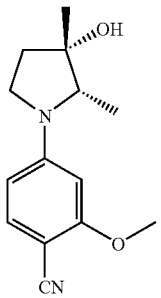

By an operation in the same manner as in Example 1 and using (2S,3S)-2,3-dimethylpyrrolidin-3-ol 0.5 oxalate (228 mg), 4-fluoro-2-methoxybenzonitrile (317 mg) and lithium carbonate (206 mg), the title compound was obtained as a colorless solid (yield: 170 mg, yield: 49%).

$^1$H-NMR(CDCl$_3$)δ: 1.22(3H,d,J=6.6 Hz), 1.38(3H,s), 1.92-2.03(1H,m), 2.12-2.25(1H,m), 3.20-3.30(1H,m), 3.45-3.60(2H,m), 3.89(3H,s), 5.96(1H,d,J=2.4 Hz), 6.12(1H,dd, J=9.0, 2.4 Hz), 7.31(1H,d,J=9.0 Hz).

IR(KBr):3441,2975,2218,1622 cm$^{-1}$.
mp:117-118° C.

Example 5

2,6-difluoro-4-[(2S,3S)-3-hydroxy-2,3-dimethylpyrrolidin-1-yl]benzonitrile

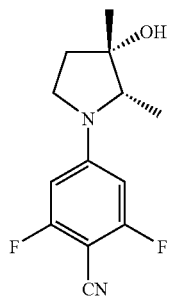

By an operation in the same manner as in Example 1 and using (2S,3S)-2,3-dimethylpyrrolidin-3-ol 0.5 oxalate (300 mg), 2,4,6-trifluorobenzonitrile (882 mg) and lithium carbonate (276 mg), the title compound was obtained as a colorless solid (yield: 263 mg, yield: 56%).

$^1$H-NMR(CDCl$_3$)δ: 1.21(3H,d,J=6.6 Hz), 1.38(3H,s), 1.95-2.15(1H,m), 2.16-2.30(1H,m), 3.15-3.26(1H,m), 3.40-3.55(2H,m), 6.07(2H,d,J=10.8 Hz).

IR(KBr):3526,2982,2226,1651 cm$^{-1}$.
mp:142-143° C.

Example 6

4-[(2S, 3S)-3-ethyl-3-hydroxy-2-methylpyrrolidin-1-yl]-2-fluorobenzonitrile

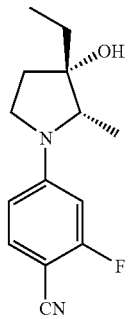

By an operation in the same manner as in Example 1 and using (2S,3S)-3-ethyl-2-methylpyrrolidin-3-ol 0.5 oxalate (257 mg), 2,4-difluorobenzonitrile (411 mg) and lithium carbonate (218 mg), the title compound was obtained as a colorless solid (yield: 250 mg, yield: 68%).

$^1$H-NMR(CDCl$_3$)δ: 1.00(3H,t,J=7.5 Hz), 1.21(3H,d,J=6.6 Hz), 1.50-1.70(3H,m), 2.00-2.20(2H,m), 3.19(1H,q,J=8.1 Hz), 3.40-3.50(1H,m), 3.59(1H,q,J=6.3 Hz), 6.24(1H,dd, J=12.6,2.1 Hz), 6.31(1H,dd,J=8.7,2.1 Hz), 7.36(1H,t,J=8.7 Hz).

IR(KBr):3416,2973,2218,1622 cm$^{-1}$.
mp:97-98° C.

Example 7

4-[(2S,3S)-3-ethyl-3-hydroxy-2-methylpyrrolidin-1-yl]-2,6-difluorobenzonitrile

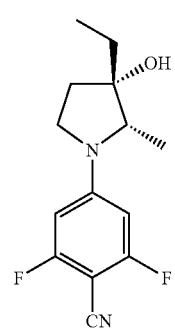

By an operation in the same manner as in Example 1 and using (2S,3S)-3-ethyl-2-methylpyrrolidin-3-ol 0.5 oxalate (257 mg), 2,4,6-trifluorobenzonitrile (464 mg) and lithium carbonate (218 mg), the title compound was obtained as a colorless solid (yield: 207 mg, yield: 53%).

$^1$H-NMR(CDCl$_3$)δ: 1.01(3H,t,J=7.2 Hz), 1.21(3H,d,J=6.3 Hz), 1.50-1.70(3H,m), 2.00-2.20(2H,m), 3.12-3.26(1H,m), 3.40-3.60(2H,m), 6.08(2H,d,J=8.1 Hz).

IR(KBr):3596,2942,2222,1644 cm$^{-1}$.
mp:140-141° C.

Example 8

4-[(2S,3S)-3-ethyl-3-hydroxy-2-methylpyrrolidin-1-yl]-2-methoxybenzonitrile

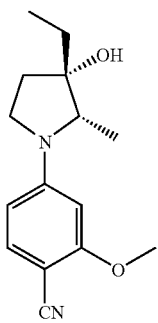

By an operation in the same manner as in Example 1 and using (2S,3S)-3-ethyl-2-methylpyrrolidin-3-ol 0.5 oxalate (257 mg), 4-fluoro-2-methoxybenzonitrile (447 mg) and lithium carbonate (218 mg), the title compound was obtained as colorless oil (yield: 305 mg, yield: 79%).

$^1$H-NMR(CDCl$_3$)δ: 1.01(3H,t,J=7.5 Hz), 1.50-1.70(3H,m), 2.00-2.20(2H,m), 3.22(1H,q,J=8.1 Hz), 3.44-3.54(1H,m), 3.62(1H,q,J=6.0 Hz), 3.89(3H,m), 5.97(1H,d,J=2.1 Hz), 6.13(1H,dd,J=8.7,2.1 Hz), 7.32(1H,d,J=8.7 Hz).

IR(KBr):3615,2973,2209,1613 cm$^{-1}$.

Example 9

4-[(2S,3S)-3-ethyl-3-hydroxy-2-methylpyrrolidin-1-yl]-3-(trifluoromethyl)benzonitrile

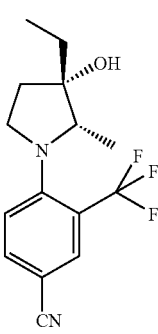

By an operation in the same manner as in Example 1 and using (2S,3S)-3-ethyl-2-methylpyrrolidin-3-ol 0.5 oxalate (257 mg), 4-fluoro-3-(trifluoromethyl)benzonitrile (419 mg) and lithium carbonate (218 mg), the title compound was obtained as colorless oil (yield: 218 mg, yield: 49%).

$^1$H-NMR(CDCl$_3$)δ: 1.00-1.10(6H,m), 1.50-2.00(5H,m), 3.18(1H,t,J=8.7 Hz), 3.59(1H,q,J=6.3 Hz), 3.82-3.98(1H,m), 6.01(1H,d,J=8.7 Hz), 7.60(1H,dd,J=8.7,2.1 Hz), 7.86(1H,d,J=2.1 Hz).

IR(KBr):3497,2975,2222,1613 cm$^{-1}$.

Example 10

4-[(2S,3S)-3-ethyl-3-hydroxy-2-methylpyrrolidin-1-yl]-2-fluoro-3-methylbenzonitrile

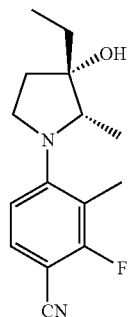

By an operation in the same manner as in Example 1 and using (2S,3S)-3-ethyl-2-methylpyrrolidin-3-ol 0.5 oxalate (257 mg), 2,4-difluoro-3-methylbenzonitrile (340 mg) and lithium carbonate (218 mg), the title compound was obtained as colorless oil (yield: 184 mg, yield: 47%).

$^1$H-NMR(CDCl$_3$)δ: 1.00-1.09(6H,m), 1.50-2.00(5H,m), 2.19(3H,d,J=2.7 Hz), 2.98(1H,dt,J=6.0,1.5 Hz), 3.54(1H,q,J=6.3 Hz), 3.84-3.95(1H,m), 6.59(1H,d,J=8.7 Hz), 7.29(1H,t,J=8.7 Hz).

IR(KBr):3499,2971,2222,1615 cm$^{-1}$.

Example 11

4-[(2S,3S)-3-hydroxy-2-methyl-3-propylpyrrolidin-1-yl]-3-(trifluoromethyl)benzonitrile

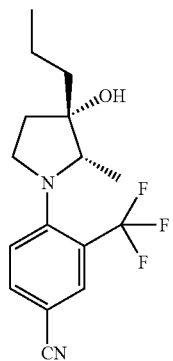

By an operation in the same manner as in Example 1 and using (2S,3S)-2-methyl-3-propylpyrrolidin-3-ol 0.5 oxalate (250 mg), 4-fluoro-3-(trifluoromethyl)benzonitrile (499 mg) and lithium carbonate (195 mg), the title compound was obtained as colorless oil (yield: 383 mg, yield: 93%).

$^1$H-NMR(CDCl$_3$)δ: 1.00(3H,t,J=6.9 Hz), 1.08(3H,d,J=6.6 Hz), 1.40-2.05(7H,m), 3.18(1H,t,J=9.0 Hz), 3.47(1H,q,J=6.3 Hz), 3.80-3.92(1H,m), 7.01(1H,d,J=8.7 Hz), 7.61(1H,dd,J=8.7,2.4 Hz), 7.87(1H,d,J=2.4 Hz)

IR(KBr):3486,2961,2222,1613 cm$^{-1}$..

Example 12

2-fluoro-4-[(2S,3S)-3-hydroxy-2-methyl-3-propylpyrrolidin-1-yl]benzonitrile

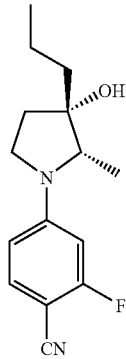

By an operation in the same manner as in Example 1 and using (2S,3S)-2-methyl-3-propylpyrrolidin-3-ol 0.5 oxalate (250 mg), 2,4-difluorobenzonitrile (367 mg) and lithium carbonate (195 mg), the title compound was obtained as colorless oil (yield: 287 mg, yield: 83%).

$^1$H-NMR(CDCl$_3$)δ: 0.96(3H,t,J=6.6 Hz), 1.20(3H,d,J=6.3 Hz), 1.40-1.60(5H,m), 2.00-2.20(2H,m), 3.15-3.25(1H,m), 3.42-3.52(1H,m), 3.58(1H,q,J=6.3 Hz), 6.24(1H,dd,J=12.6, 2.1 Hz), 6.31(1H,dd,J=8.7,2.1 Hz), 7.36(1H,t,J=8.7 Hz).

IR(KBr):3459,2959,2218,1622 cm$^{-1}$.

Example 13

4-[(2S,3S)-3-hydroxy-2-methyl-3-propylpyrrolidin-1-yl]-2-methoxybenzonitrile

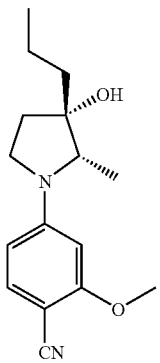

By an operation in the same manner as in Example 1 and using (2S,3S)-2-methyl-3-propylpyrrolidin-3-ol 0.5 oxalate (250 mg), 4-fluoro-2-methoxybenzonitrile (399 mg) and lithium carbonate (195 mg), the title compound was obtained as colorless oil (yield: 303 mg, yield: 83%).

$^1$H-NMR(CDCl$_3$)δ: 0.96(3H,t,J=6.6 Hz), 1.21(3H,d,J=6.3 Hz), 1.40-1.60(5H,m), 2.00-2.20(2H,m), 3.23(1H,q,J=7.1 Hz), 3.45-3.55(1H,m), 3.62(1H,q,J=6.3 Hz), 3.89(3H,s), 5.97(1H,d,J=2.1 Hz), 6.12(1H,dd,J=8.7,2.1 Hz), 7.32(1H,d,J=8.7 Hz).

IR(KBr):3449,2959,2209,1611 cm$^{-1}$.

Example 14

2,6-difluoro-4-[(2S,3S)-3-hydroxy-2-methyl-3-propylpyrrolidin-1-yl]benzonitrile

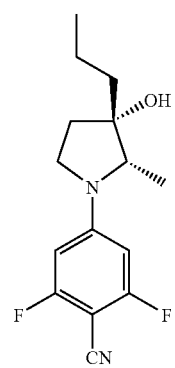

By an operation in the same manner as in Example 1 and using (2S,3S)-2-methyl-3-propylpyrrolidin-3-ol 0.5 oxalate (250 mg), 2,4,6-trifluorobenzonitrile (414 mg) and lithium carbonate (195 mg), the title compound was obtained as colorless oil (yield: 233 mg, yield: 63%).

$^1$H-NMR(CDCl$_3$)δ: 0.96(3H,t,J=6.9 Hz), 1.20(3H,d,J=6.6 Hz), 1.40-1.60(5H,m), 2.00-2.20(2H,m), 3.15-3.25(1H,m), 3.40-3.47(1H,m), 3.54(1H,q,J=6.2 Hz), 6.08(2H,d,J=10.8 Hz).

IR(KBr):3459,2963,2226,1644 cm$^{-1}$.

Example 15

2-chloro-4-[(2S,3S)-3-hydroxy-2,3-dimethylpyrrolidin-1-yl]-3-methylbenzonitrile

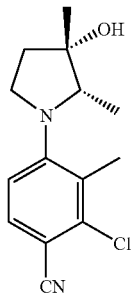

By an operation in the same manner as in Example 1 and using (2S,3S)-2,3-dimethylpyrrolidin-3-ol 0.5 oxalate (260 mg), 2-chloro-4-fluoro-3-methylbenzonitrile (550 mg) and lithium carbonate (240 mg), the title compound was obtained as a colorless solid (yield: 320 mg, yield: 75%).

$^1$H-NMR(CDCl$_3$)δ: 1.05(3H,d,J=6.0 Hz), 1.41(3H,s), 1.69(1H,s), 1.85-2.10(2H,m), 2.34(3H,s), 2.82(1H,dt,J=9.6, 5.7 Hz), 3.44(1H,q,J=6.3 Hz), 3.80-3.85(1H,m), 6.78(1H,d, J=8.7 Hz), 7.40(1H,d,J=8.7 Hz).

IR(KBr):3609,2975,2230,1586 cm$^{-1}$.

mp:109-110° C.

Example 16

2-chloro-4-[(2S,3S)-3-hydroxy-2,3-dimethylpyrrolidin-1-yl]benzonitrile

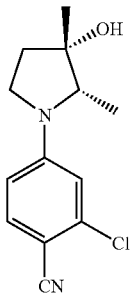

By an operation in the same manner as in Example 1 and using (2S,3S)-2,3-dimethylpyrrolidin-3-ol 0.5 oxalate (1.50 g), 2-chloro-4-fluorobenzonitrile (3.04 g) and lithium carbonate (1.04 g), the title compound was obtained as a colorless solid (yield: 1.70 g, yield: 72%).

$^1$H-NMR(CDCl$_3$)δ: 1.21(3H,d,J=6.3 Hz), 1.37(3H,s), 1.63(1H,s), 1.90-2.05(1H,m), 2.14-2.25(1H,m), 3.15-3.26 (1H,m), 3.40-3.60(2H,m), 6.41(1H,dd,J=8.7,1.8 Hz), 6.54 (1H,d,J=1.8 Hz), 7.40(1H,d,J=8.7 Hz).

IR(KBr):3406,2973,2216,1601 cm$^{-1}$.

mp:127-128° C.

Example 17

2-fluoro-4-[(2S,3S)-3-hydroxy-2-methyl-3-(trifluoromethyl)pyrrolidin-1-yl]benzonitrile

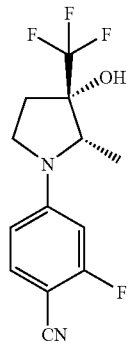

By an operation in the same manner as in Example 1 and using (2S,3S)-2-methyl-3-(trifluoromethyl)pyrrolidin-3-ol 0.5 oxalate (200 mg), 2,4-difluorobenzonitrile (258 mg) and lithium carbonate (138 mg), the title compound was obtained as a colorless solid (yield: 120 mg, yield: 45%).

$^1$H-NMR(CDCl$_3$)δ: 1.30(3H,d,J=6.3 Hz), 2.20-2.35(1H, m), 2.42-2.55(2H,m), 3.35-3.45(1H,m), 3.50-3.65(1H,m), 4.10(1H,q,J=6.6 Hz), 6.25-6.37(2H,m), 7.39(1H,dd,J=8.7, 7.5 Hz).

IR(KBr): 3378,2988,2224,1622 cm$^{-1}$.

mp:148-149° C.

Example 18

2-chloro-4-[(2S,3S)-3-hydroxy-2-methyl-3-(trifluoromethyl)pyrrolidin-1-yl]benzonitrile

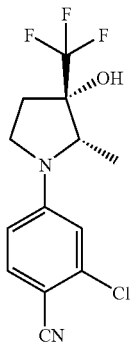

By an operation in the same manner as in Example 1 and using (2S,3S)-2-methyl-3-(trifluoromethyl)pyrrolidin-3-ol 0.5 oxalate (200 mg), 2-chloro-4-fluorobenzonitrile (289 mg) and lithium carbonate (138 mg), the title compound was obtained as a colorless solid (yield: 100 mg, yield: 35%).

$^1$H-NMR(CDCl$_3$)δ: 1.29(3H,d,J=6.6 Hz), 2.20-2.31(1H, m), 2.42-2.55(2H,m), 3.36-3.45(1H,m), 3.56-3.64(1H,m), 4.12(1H,q,J=6.6 Hz), 6.45(1H,dd,J=8.7,1.5 Hz), 6.58(1H,d, J=1.5 Hz), 7.44(1H,d,J=8.7 Hz).

IR(KBr):3341,2986,2224,1601 cm$^{-1}$.

mp:149-150° C.

Example 19

2-fluoro-4-[(2S,3S)-3-hydroxy-2-isopropyl-3-methylpyrrolidin-1-yl]benzonitrile

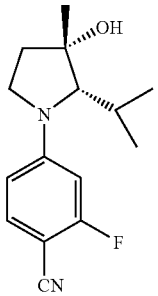

By an operation in the same manner as in Example 1 and using (2S,3S)-2-isopropyl-3-methylpyrrolidin-3-ol 0.5 oxalate (150.6 mg), 2,4-difluorobenzonitrile (112 mg) and lithium carbonate (126 mg), the title compound was obtained as a colorless solid (yield: 145 mg, yield: 69%).

$^1$H-NMR(CDCl$_3$)δ: 0.95(3H,d,J=6.9 Hz), 1.13(3H,d, J=6.9 Hz), 1.32(3H,s), 1.58(1H,s), 1.93-2.00(1H,m), 2.10-2.34(2H,m), 3.10-3.19(1H,m), 3.27(1H,d,J=5.7 Hz), 3.42-3.49(1H,m), 6.25(1H,dd,J=12.6,2.4 Hz), 6.32(1H,dd,J=8.7, 2.4 Hz), 7.33(1H,t,J=8.7 Hz)

IR(KBr):3459,2965,2218,1624,1518 cm$^{-1}$..

Example 20

2,6-difluoro-4-[(2S,3S)-3-hydroxy-2-isopropyl-3-methylpyrrolidin-1-yl]benzonitrile

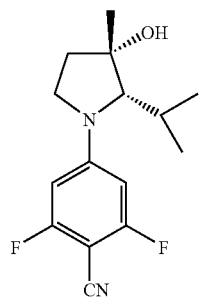

By an operation in the same manner as in Example 1 and using (2S,3S)-2-isopropyl-3-methylpyrrolidin-3-ol 0.5 oxalate (150.6 mg), 2,4,6-trifluorobenzonitrile (126 mg) and lithium carbonate (126 mg), the title compound was obtained as a colorless solid (yield: 168 mg, yield: 75%).

$^1$H-NMR(CDCl$_3$)δ: 0.95(3H,d,J=6.9 Hz), 1.13(3H,d, J=6.9 Hz), 1.32(3H,s), 1.79(1H,s), 1.94-2.01(1H,m), 2.11-2.35(2H,m), 3.10-3.19(1H,m), 3.22(1H,d,J=5.7 Hz), 3.40-3.48(1H,m), 6.10(2H,d,J=11.4 Hz).

IR(KBr):3433,2967,2226,1644,1524 cm$^{-1}$.

Example 21

4-[(2S,3S)-3-hydroxy-2-isopropyl-3-methylpyrrolidin-1-yl]-2-methoxybenzonitrile

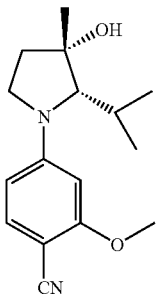

By an operation in the same manner as in Example 1 and using (2S,3S)-2-isopropyl-3-methylpyrrolidin-3-ol 0.5 oxalate (150.6 mg), 4-fluoro-2-methoxybenzonitrile (121 mg) and lithium carbonate (126 mg), the title compound was obtained as a colorless solid (yield: 20 mg, yield: 9.1%).

$^1$H-NMR(CDCl$_3$)δ: 0.96(3H,d,J=6.9 Hz), 1.13(3H,d, J=6.9 Hz), 1.32(3H,s), 1.57(1H,s), 1.92-1.99(1H,m), 2.15-2.33(2H,m), 3.13-3.22(1H,m), 3.31(1H,d,J=5.4 Hz), 3.45-3.52(1H,m), 3.88(3H,s), 5.98(1H,d,J=2.1 Hz), 6.13(1H,dd, J=8.7,2.1 Hz), 7.33(1H,d,J=8.7 Hz).

IR(KBr):3447,2961,2211,1609,1518 cm$^{-1}$.

Example 22

2-chloro-4-[(2S,3S)-3-hydroxy-2-isopropyl-3-methylpyrrolidin-1-yl]benzonitrile

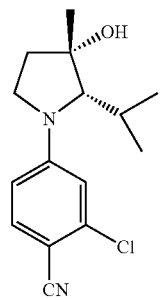

By an operation in the same manner as in Example 1 and using (2S,3S)-2-isopropyl-3-methylpyrrolidin-3-ol 0.5 oxalate (132 mg), 2-chloro-4-fluorobenzonitrile (109 mg) and lithium carbonate (111 mg), the title compound was obtained as colorless oil (yield: 133 mg, yield: 68%).

$^1$H-NMR(CDCl$_3$)δ: 0.95(3H,d,J=6.9 Hz), 1.13(3H,d, J=6.9 Hz), 1.32(3H,s), 1.69(1H,s), 1.93-2.00(1H,m), 2.11-2.34(2H,m), 3.10-3.20(1H,m), 3.29(1H,d,J=5.7 Hz), 3.43-3.50(1H,m), 6.44(1H,dd,J=9.0,2.4 Hz), 6.56(1H,d,J=2.4 Hz), 7.39(1H,d,J=9.0 Hz).

IR(KBr):3451,2965,2218,1599,1510 cm$^{-1}$.

Example 23

4-[(2S,3S)-3-ethyl-3-hydroxy-2-isopropylpyrrolidin-1-yl]-2,6-difluorobenzonitrile

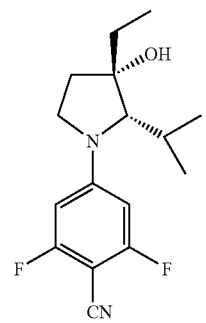

By an operation in the same manner as in Example 1 and using (2S,3S)-3-ethyl-2-isopropylpyrrolidin-3-ol 0.5 oxalate (203 mg), 2,4,6-trifluorobenzonitrile (157 mg) and lithium carbonate (163 mg), the title compound was obtained as colorless oil (yield: 143 mg, yield: 49%).

$^1$H-NMR(CDCl$_3$)δ: 0.95(3H,d,J=6.9 Hz), 0.96(3H,t,J=7.5 Hz), 1.12(3H,d,J=6.9 Hz), 1.47-1.56(2H,m), 1.59(1H,s), 2.07-2.26(3H,m), 3.05-3.15(1H,m), 3.28(1H,d,J=6.0 Hz), 3.39-3.46(1H,m), 6.09(2H,d,J=11.4 Hz).

IR(KBr):3486,2965,2226,1644,1524 cm$^{-1}$.

Example 24

4-[(2S,3S)-3-ethyl-3-hydroxy-2-isopropylpyrrolidin-1-yl]-2-methoxybenzonitrile

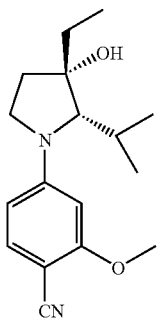

By an operation in the same manner as in Example 1 and using (2S,3S)-3-ethyl-2-isopropylpyrrolidin-3-ol 0.5 oxalate (203 mg), 4-fluoro-2-methoxybenzonitrile (151 mg) and lithium carbonate (163 mg), the title compound was obtained as colorless oil (yield: 22 mg, yield: 7.6%).

$^1$H-NMR(CDCl$_3$)δ: 0.95(3H,d,J=6.6 Hz), 0.95(3H,t,J=7.2 Hz), 1.13(3H,d,J=6.6 Hz), 1.47-1.54(2H,m), 1.56(1H,s), 2.03-2.25(3H,m), 3.09-3.18(1H,m), 3.36(1H,d,J=5.7 Hz), 3.43-3.50(1H,m), 3.88(3H,s), 5.97(1H,d,J=2.1 Hz), 6.13(1H,dd,J=8.7,2.1 Hz), 7.30(1H,d,J=8.7 Hz).

IR(KBr):3455,2963,2211,1609,1518 cm$^{-1}$.

Example 25

4-[(2S,3S)-3-ethyl-3-hydroxy-2-isopropylpyrrolidin-1-yl]-2-(trifluoromethyl)benzonitrile

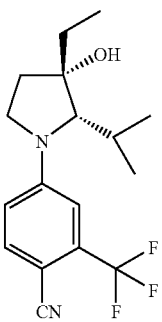

By an operation in the same manner as in Example 1 and using (2S,3S)-3-ethyl-2-isopropylpyrrolidin-3-ol 0.5 oxalate (203 mg), 4-fluoro-2-(trifluoromethyl)benzonitrile (189 mg) and lithium carbonate (163 mg), the title compound was obtained as colorless oil (yield: 180 mg, yield: 55%).

$^1$H-NMRCDCl$_3$)δ: 0.95(3H,d,J=6.9 Hz), 0.96(3H,t,J=7.2 Hz), 1.14(3H,d,J=6.9 Hz), 1.47-1.56(2H,m), 1.64(1H,s), 2.07-2.28(3H,m), 3.11-3.20(1H,m), 3.40(1H,d,J=5.7 Hz), 3.47-3.54(1H,m), 6.65(1H,dd,J=8.7,2.7 Hz), 6.80(1H,d,J=2.7 Hz), 7.54(1H,d,J=8.7 Hz).

IR(KBr):3476,2963,2218,1613,1520 cm$^{-1}$.

Example 26

4-[(2S,3S)-3-ethyl-3-hydroxy-2-isopropylpyrrolidin-1-yl]-2-fluorobenzonitrile

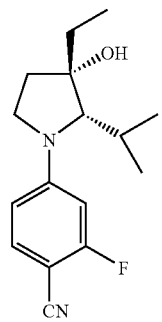

By an operation in the same manner as in Example 1 and using (2S,3S)-3-ethyl-2-isopropylpyrrolidin-3-ol 0.5 oxalate (162 mg), 2,4-difluorobenzonitrile (112 mg) and lithium carbonate (126 mg), the title compound was obtained as colorless oil (yield: 136 mg, yield: 62%).

$^1$H-NMR(CDCl$_3$)δ: 0.95(3H,d,J=6.9 Hz), 0.95(3H,t,J=7.3 Hz), 1.12(3H,d,J=6.9 Hz), 1.44-1.55(2H,m), 1.54(1H,s), 2.04-2.26(3H,m), 3.05-3.15(1H,m), 3.33(1H,d,J=5.7 Hz), 3.40-3.48(1H,m), 6.24(1H,dd,J=12.9,2.4 Hz), 6.32(1H,dd,J=8.7,2.4 Hz), 7.33(1H,t,J=7.8 Hz).

IR(KBr):3472,2963,2218,1624,1518 cm$^{-1}$.

Example 27

2-chloro-4-[(2S,3S)-3-ethyl-3-hydroxy-2-isopropylpyrrolidin-1-yl]benzonitrile

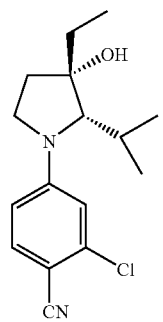

By an operation in the same manner as in Example 1 and using (2S,3S)-3-ethyl-2-isopropylpyrrolidin-3-ol 0.5 oxalate (162 mg), 2-chloro-4-fluorobenzonitrile (125 mg) and lithium carbonate (126 mg), the title compound was obtained as pale-brown oil (yield: 151 mg, yield: 65%).

$^1$H-NMR(CDCl$_3$)δ: 0.95(3H,d,J=6.9 Hz), 0.95(3H,t,J=7.4 Hz), 1.12(3H,d,J=6.9 Hz), 1.46-1.55(2H,m), 1.57(1H,s), 2.04-2.26(3H,m), 3.06-3.15(1H,m), 3.35(1H,d,J=5.7 Hz), 3.41-3.48(1H,m), 6.43(1H,dd,J=8.7,2.4 Hz), 6.55(1H,d,J=2.4 Hz), 7.38(1H,t,J=8.7 Hz).

IR(KBr):3465,2963,2218,1599,1508 cm$^{-1}$.

Example 28

4-[(2S,3R)-3-cyclopropyl-3-hydroxy-2-isopropylpyrrolidin-1-yl]-2,6-difluorobenzonitrile

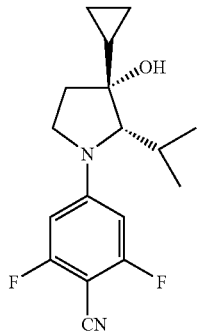

By an operation in the same manner as in Example 1 and using (2S,3R)-3-cyclopropyl-2-isopropylpyrrolidin-3-ol 0.5 oxalate (215 mg), 2,4,6-trifluorobenzonitrile (157 mg) and lithium carbonate (163 mg), the title compound was obtained as a colorless solid (yield: 115 mg, yield: 38%).

$^1$H-NMR(CDCl$_3$)δ: 0.27-0.48(4H,m), 0.94(3H,d,J=6.9 Hz), 0.94-1.04(1H,m), 1.10(3H,d,J=6.9 Hz), 1.46(1H,s), 2.06-2.21(2H,m), 2.25-2.36(1H,m), 3.16-3.27(2H,m), 3.42-3.50(1H,m), 6.09(2H,d,J=11.4 Hz).

IR(KBr):3486,2961,2226,1644,1522 cm$^{-1}$.

Example 29

4-[(2S,3R)-3-cyclopropyl-3-hydroxy-2-isopropylpyrrolidin-1-yl]-2-(trifluoromethyl)benzonitrile

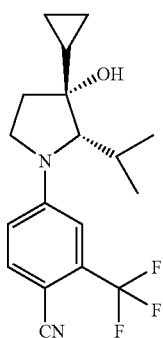

By an operation in the same manner as in Example 1 and using (2S,3R)-3-cyclopropyl-2-isopropylpyrrolidin-3-ol 0.5 oxalate (215 mg), 4-fluoro-2-(trifluoromethyl)benzonitrile (189 mg) and lithium carbonate (163 mg), the title compound was obtained as a pale-brown solid (yield: 227 mg, yield: 67%).

$^1$H-NMR(CDCl$_3$)δ: 0.28-0.47(4H,m), 0.94(3H,d,J=6.9 Hz), 0.94-1.07(1H,m), 1.11(3H,d,J=6.9 Hz), 1.56(1H,s), 2.08-2.25(2H,m), 2.27-2.37(1H,m), 3.23-3.33(2H,m), 3.51-3.58(1H,m), 6.67(1H,dd,J=8.7,2.4 Hz), 6.82(1H,d,J=2.4 Hz), 7.55(1H,d,J=8.7 Hz).

IR(KBr):3476,2963,2218,1613,1518 cm$^{-1}$.

Example 30

4-[(2S,3R)-3-cyclopropyl-3-hydroxy-2-isopropylpyrrolidin-1-yl]-2-fluorobenzonitrile

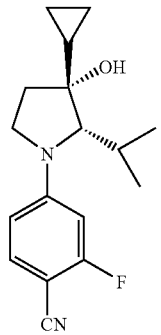

By an operation in the same manner as in Example 1 and using (2S,3R)-3-cyclopropyl-2-isopropylpyrrolidin-3-ol 0.5 oxalate (215 mg), 2,4-difluorobenzonitrile (139 mg) and lithium carbonate (163 mg), the title compound was obtained as a pale-brown solid (yield: 114 mg, yield: 40%).

$^1$H-NMR(CDCl$_3$)δ: 0.24-0.46(4H,m), 0.94(3H,d,J=7.2 Hz), 0.94-1.03(1H,m), 1.10(3H,d,J=7.2 Hz), 1.49(1H,s), 2.04-2.21(2H,m), 2.25-2.35(1H,m), 3.18-3.27(2H,m), 3.44-3.51(1H,m), 6.25(1H,dd,J=12.9,2.1 Hz), 6.33(1H,dd,J=8.7, 2.1 Hz), 7.34(1H,t,J=8.3 Hz).

IR(KBr):3484,2961,2218,1620,1518 cm$^{-1}$.

Example 31

2-chloro-4-[(2S,3R)-3-cyclopropyl-3-hydroxy-2-isopropylpyrrolidin-1-yl]benzonitrile

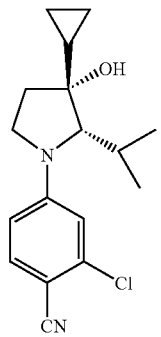

By an operation in the same manner as in Example 1 and using (2S,3R)-3-cyclopropyl-2-isopropylpyrrolidin-3-ol 0.5 oxalate (215 mg), 2-chloro-4-fluorobenzonitrile (156 mg) and lithium carbonate (163 mg), the title compound was obtained as a pale-brown solid (yield: 130 mg, yield: 43%).

$^1$H-NMR(CDCl$_3$)δ: 0.25-0.46(4H,m), 0.94(3H,d,J=7.2 Hz), 0.94-1.01(1H,m), 1.10(3H,d,J=7.2 Hz), 1.48(1H,s), 2.05-2.21(2H,m), 2.24-2.35(1H,m), 3.18-3.28(2H,m), 3.45-3.52(1H,m), 6.44(1H,dd,J=8.7,2.4 Hz), 6.56(1H,d,J=2.4 Hz), 7.39(1H,t,J=8.7 Hz).

IR(KBr):3480,2961,2216,1599,1510 cm$^{-1}$.

Example 32

4-[(2S,3R)-3-cyclopropyl-3-hydroxy-2-methylpyrrolidin-1-yl]-2-fluorobenzonitrile

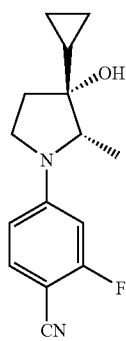

By an operation in the same manner as in Reference Example 4 and using benzyl (2S,3R)-3-cyclopropyl-3-hydroxy-2-methylpyrrolidine-1-carboxylate (1.64 g) and 50% water containing-10% Pd/C (0.30 g), (2S,3R)-3-cyclopropyl-2-methylpyrrolidin-3-ol 0.5 oxalate was obtained as a colorless solid (yield: 677.5 mg, yield: 69%).

By an operation in the same manner as in Example 1 and using (2S,3R)-3-cyclopropyl-2-methylpyrrolidin-3-ol 0.5 oxalate (200 mg), 2,4-difluorobenzonitrile (255 mg) and lithium carbonate (180 mg), the title compound was obtained as a colorless solid (yield: 188 mg, yield: 59%).

$^1$H-NMR(CDCl$_3$)δ: 0.30-0.58(4H,m), 0.97-1.13(1H,m), 1.20(3H,d,J=6.4 Hz), 1.41(1H,brs), 1.95-2.23(2H,m), 3.21-3.37(1H,m), 3.42-3.60(2H,m), 6.18-6.39(2H,m), 7.36(1H,t, J=8.2 Hz).

IR(KBr):3443,2975,2218,1549 cm$^{-1}$.
mp:112-113° C.

Example 33

4-[(2S,3R)-3-cyclopropyl-3-hydroxy-2-methylpyrrolidin-1-yl]-2,6-difluorobenzonitrile

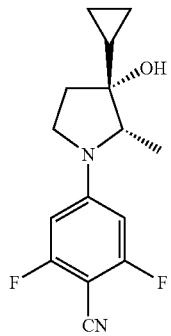

By an operation in the same manner as in Example 1 and using (2S,3R)-3-cyclopropyl-2-methylpyrrolidin-3-ol 0.5 oxalate (200 mg), 2,4,6-trifluorobenzonitrile (288 mg) and lithium carbonate (180 mg), the title compound was obtained as a colorless solid (yield: 172 mg, yield: 51%).

$^1$H-NMR(CDCl$_3$)δ: 0.31-0.45(2H,m), 0.42-0.57(2H,m), 0.98-1.14(1H,m), 1.20(3H,d,J=6.4 Hz), 1.35(1H,s), 1.97-2.23(2H,m), 3.21-3.35(1H,m), 3.40-3.55(2H,m), 6.09(2H,d, J=10.9 Hz).

IR(KBr):3443,2226,1644,1526 cm$^{-1}$.
mp:130-131° C.

Example 34

4-[(2S,3R)-3-cyclopropyl-3-hydroxy-2-methylpyrrolidin-1-yl]-2-methoxybenzonitrile

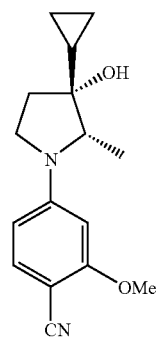

By an operation in the same manner as in Example 1 and using (2S,3R)-3-cyclopropyl-2-methylpyrrolidin-3-ol 0.5 oxalate (200 mg), 2-methoxy-4-fluorobenzonitrile (277 mg) and lithium carbonate (180 mg), the title compound was obtained as a pale-yellow solid (yield: 192 mg, yield: 58%).

$^1$H-NMR(CDCl$_3$)δ: 0.32-0.54(4H,m), 1.00-1.14(1H,m), 1.22(3H,d,J=6.4 Hz), 1.47-1.55(1H,m), 1.96-2.22(2H,m), 3.24-3.39(1H,m), 3.44-3.63(2H,m), 3.89(3H,s), 5.98(1H,d, J=2.3 Hz), 6.14(1H,dd,J=8.8,2.3 Hz), 7.32(1H,d,J=8.9 Hz).

IR(KBr):3486,2975,2209,1615 cm$^{-1}$.
mp:115-116° C.

Example 35

4-[(2S,3R)-3-cyclopropyl-3-hydroxy-2-methylpyrrolidin-1-yl]-2-fluoro-3-methylbenzonitrile

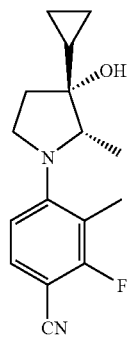

By an operation in the same manner as in Example 1 and using (2S,3R)-3-cyclopropyl-2-methylpyrrolidin-3-ol 0.5 oxalate (260 mg), 2,4-difluoro-3-methylbenzonitrile (364 mg) and lithium carbonate (234 mg), the title compound was obtained as a colorless solid (yield: 106 mg, yield: 24%).

¹H-NMR(CDCl₃)δ: 0.34-0.48(1H,m), 0.43-0.63(3H,m), 0.96-1.09(1H,m), 1.11(3H,d,J=6.2 Hz), 1.43(1H,s), 1.69-1.82(2H,m), 2.18(3H,d,J=2.6 Hz), 2.92-3.06(1H,m), 3.69(1H,q,J=6.2 Hz), 3.84-3.98(1H,m), 6.61(1H,d,J=8.5 Hz), 7.23-7.37(1H,m).
IR(KBr):3486,2975,2224,1613 cm⁻¹.
mp:127-128° C.

Example 36

2-fluoro-4-[(2S,3R)-3-hydroxy-2-methyl-3-vinylpyrrolidin-1-yl]benzonitrile

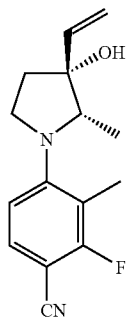

To tert-butyl (2S,3R)-3-hydroxy-2-methyl-3-vinylpyrrolidine-1-carboxylate (684 mg, 2.85 mmol) was added trifluoroacetic acid (3.0 ml). The mixture was stirred at room temperature for 15 min, and concentrated under reduced pressure to give (2S,3R)-2-methyl-3-vinylpyrrolidin-3-ol (yield: 1.11 g).

By an operation in the same manner as in Example 1 and using (2S,3R)-2-methyl-3-vinylpyrrolidin-3-ol (554 mg), 2,4-difluorobenzonitrile (300 mg) and lithium carbonate (350 mg), the title compound was obtained as a colorless solid (yield: 177 mg, yield: 50%).

¹H-NMR(CDCl₃)δ: 1.23(3H,d,J=6.4 Hz), 1.78-1.91(1H,m), 2.02-2.17(1H,m), 2.15-2.31(1H,m), 3.19-3.33(1H,m), 3.49-3.62(1H,m), 3.71(1H,q,J=6.4 Hz), 5.20(1H,d,J=10.7 Hz), 5.31(1H,d,J=17.3 Hz), 6.00(1H,dd,J=17.3,10.7 Hz), 6.26(1H,dd,J=12.7,2.4 Hz), 6.34(1H,dd,J=8.7,2.4 Hz), 7.30-7.42(1H,m).
IR(KBr):3436,2980,2218,1620 cm⁻¹.
mp:85-86° C.

Example 37

2-fluoro-4-[(2S,3R)-3-hydroxy-2-methyl-3-vinylpyrrolidin-1-yl]-3-methylbenzonitrile

By an operation in the same manner as in Example 1 and using (2S,3R)-2-methyl-3-vinylpyrrolidin-3-ol (556 mg), 2,4-difluoro-3-methylbenzonitrile (350 mg) and lithium carbonate (350 mg), the title compound was obtained as a colorless solid (yield: 84.6 mg, yield: 23%).

¹H-NMR(CDCl₃)δ: 1.03(3H,d,J=6.4 Hz), 1.75(1H,s), 1.90-2.14(2H,m), 2.20(3H,d,J=2.7 Hz), 2.97-3.12(1H,m), 3.66(1H,q,J=6.4 Hz), 3.94-4.08(1H,m), 5.29(1H,d,J=11.7 Hz), 5.48(1H,d,J=16.3 Hz), 5.88-6.05(1H,m), 6.60(1H,d,J=8.7 Hz), 7.23-7.36(1H,m).
IR(KBr):3480,2976,2224,1615 cm⁻¹.
mp:114-115° C.

Example 38

4-[(2S,3S)-2-ethyl-3-hydroxy-3-methylpyrrolidin-1-yl]-2-fluorobenzonitrile

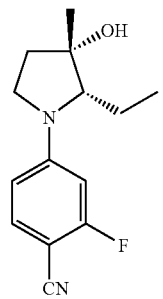

By an operation in the same manner as in Example 1 and using (2S,3S)-2-ethyl-3-methylpyrrolidin-3-ol 0.5 oxalate (200 mg), 2,4-difluorobenzonitrile (240 mg) and lithium carbonate (187 mg), the title compound was obtained as pale-yellow oil (yield: 188.6 mg, yield: 66%).

¹H-NMR(CDCl₃)δ: 1.02(3H,t,J=7.6 Hz), 1.37(3H,s), 1.48-1.72(2H,m), 1.72-1.91(1H,m), 1.91-2.07(1H,m), 2.13-2.32(1H,m), 3.09-3.25(1H,m), 3.31(1H,dd,J=8.0,3.8 Hz), 3.39-3.53(1H,m), 6.21(1H,dd,J=12.9,2.3 Hz), 6.29(1H,dd,J=8.7,2.3 Hz), 7.29-7.43(1H,m).
IR(KBr):3438,2969,2218,1520 cm⁻¹.

Example 39

4-[(2S,3S)-2-ethyl-3-hydroxy-3-methylpyrrolidin-1-yl]-2,6-difluorobenzonitrile

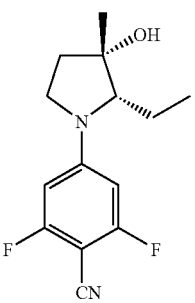

By an operation in the same manner as in Example 1 and using (2S,3S)-2-ethyl-3-methylpyrrolidin-3-ol 0.5 oxalate (200 mg), 2,4,6-trifluorobenzonitrile (270 mg) and lithium carbonate (187 mg), the title compound was obtained as a colorless solid (yield: 187.5 mg, yield: 61%).

$^1$H-NMR(CDCl$_3$)δ: 1.02(3H,t,J=7.4 Hz), 1.37(3H,s), 1.49-1.67(2H,m), 1.73-1.91(1H,m), 1.92-2.07(1H,m), 2.15-2.30(1H,m), 3.12-3.24(1H,m), 3.27(1H,dd,J=8.0,3.8 Hz), 3.38-3.51(1H,m), 6.06(2H,d,J=11.4 Hz).

IR(KBr):3457,2971,2226,1644 cm$^{-1}$.

mp:104-105° C.

Example 40

4-[(2S,3S)-2-ethyl-3-hydroxy-3-methylpyrrolidin-1-yl]-2-(trifluoromethyl)benzonitrile

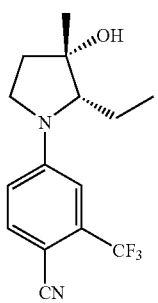

By an operation in the same manner as in Example 1 and using (2S,3S)-2-ethyl-3-methylpyrrolidin-3-ol 0.5 oxalate (200 mg), 4-fluoro-2-(trifluoromethyl)benzonitrile (325 mg) and lithium carbonate (187 mg), the title compound was obtained as pale-yellow oil (yield: 306.6 mg, yield: 90%).

$^1$H-NMR(CDCl$_3$)δ: 1.03(3H,t,J=7.6 Hz), 1.38(3H,s), 1.48-1.74(2H,m), 1.74-1.93(1H,m), 1.95-2.07(1H,m), 2.17-2.33(1H,m), 3.14-3.31(1H,m), 3.38(1H,dd,J=7.6,3.8 Hz), 3.46-3.58(1H,m), 6.61(1H,dd,J=8.7,2.3 Hz), 6.78(1H,d,J=2.3 Hz), 7.57(1H,d,J=8.7 Hz).

IR(KBr):3438,2971,2218,1615 cm$^1$.

Example 41

2-chloro-4-[(2S,3S)-2-ethyl-3-hydroxy-3-methylpyrrolidin-1-yl]benzonitrile

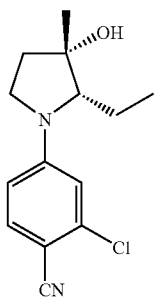

By an operation in the same manner as in Example 1 and using (2S,3S)-2-ethyl-3-methylpyrrolidin-3-ol 0.5 oxalate (195 mg), 2-chloro-4-fluorobenzonitrile (320 mg) and lithium carbonate (200 mg), the title compound was obtained as a colorless solid (yield: 221.4 mg, yield: 75%).

$^1$H-NMR(CDCl$_3$)δ: 1.02(3H,t,J=7.4 Hz), 1.37(3H,s), 1.48-1.67(1H,m), 1.63-1.89(2H,m), 1.91-2.09(1H,m), 2.13-2.30(1H,m), 3.10-3.25(1H,m), 3.33(1H,dd,J=7.8,3.6 Hz), 3.40-3.54(1H,m), 6.35-6.45(1H,m), 6.53(1H,d,J=2.3 Hz), 7.40(1H,d,J=8.7 Hz).

IR(KBr):3413,2969,2216,1599 cm$^{-1}$.

mp:77-78° C.

Example 42

4-[(2S,3S)-2-ethyl-3-hydroxy-3-methylpyrrolidin-1-yl]-2-methoxybenzonitrile

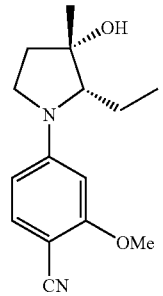

By an operation in the same manner as in Example 1 and using (2S,3S)-2-ethyl-3-methylpyrrolidin-3-ol 0.5 oxalate (210 mg), 4-fluoro-2-methoxybenzonitrile (320 mg) and lithium carbonate (210 mg), the title compound was obtained as a pale-yellow solid (yield: 195.8 mg, yield: 62%).

$^1$H-NMR(CDCl$_3$)δ: 1.03(3H,t,J=7.6 Hz), 1.37(3H,s), 1.51-1.72(1H,m), 1.73-1.91(2H,m), 1.91-2.03(1H,m), 2.13-2.29(1H,m), 3.13-3.28(1H,m), 3.33(1H,dd,J=8.0,3.4 Hz), 3.42-3.56(1H,m), 3.88(3H,s), 5.96(1H,d,J=1.9 Hz), 6.10(1H,dd,J=8.7,1.9 Hz), 7.31(1H,d,J=8.7 Hz).

IR(KBr):3439,2967,2209,1613 cm$^{-1}$.

mp:110-111° C.

Example 43

2-chloro-4-[(2S,3S)-2-ethyl-3-hydroxy-3-methylpyrrolidin-1-yl]-3-methylbenzonitrile

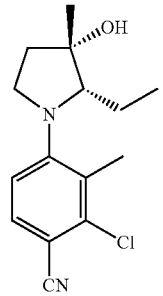

By an operation in the same manner as in Example 1 and using (2S,3S)-2-ethyl-3-methylpyrrolidin-3-ol 0.5 oxalate (210 mg), 2-chloro-4-fluoro-3-methylbenzonitrile (300 mg) and lithium carbonate (215 mg), the title compound was obtained as pale-yellow oil (yield: 91.2 mg, yield: 27%).

¹H-NMR(CDCl₃)δ: 0.96(3H,t,J=7.8 Hz), 1.37-1.53(1H, m), 1.50(3H,s), 1.61-1.76(2H,m), 1.86-2.02(2H,m), 2.33(3H,s), 2.76-2.88(1H,m), 3.34(1H,dd,J=8.3,3.0 Hz), 3.74-3.92(1H,m), 6.78(1H,d,J=8.7 Hz), 7.40(1H,d,J=8.7 Hz).

IR(KBr):3478,2969,2220,1586 cm⁻¹.

Example 44

2-fluoro-4-[(2S,3S)-2-ethyl-3-hydroxy-3-methylpyrrolidin-1-yl]-3-methylbenzonitrile

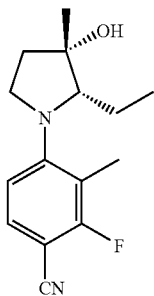

By an operation in the same manner as in Example 1 and using (2S,3S)-2-ethyl-3-methylpyrrolidin-3-ol 0.5 oxalate (220 mg), 2,4-difluoro-3-methylbenzonitrile (290 mg) and lithium carbonate (210 mg), the title compound was obtained as pale-yellow oil (yield: 97.3 mg, yield: 29%).

¹H-NMR(CDCl₃)δ: 0.97(3H,t,J=7.8 Hz), 1.41-1.55(1H, m), 1.50(3H,s), 1.60-1.75(2H,m), 1.86-2.00(2H,m), 2.18 (3H,d,J=2.7 Hz), 2.89-3.03(1H,m), 3.40(1H,dd,J=8.5,3.2 Hz), 3.80-3.95(1H,m), 6.59(1H,d,J=8.7 Hz), 7.23-7.35(1H, m).

IR(KBr):3478,2967,2224,1615 cm⁻¹.

Example 45

4-[(2S,3S)-2,3-diethyl-3-hydroxypyrrolidin-1-yl]-2-fluorobenzonitrile

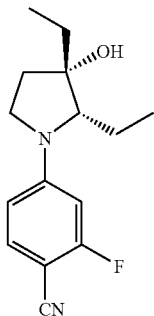

By an operation in the same manner as in Example 1 and using (2S,3S)-2,3-diethylpyrrolidin-3-ol 0.5 oxalate (196 mg), 2,4-difluorobenzonitrile (284 mg) and lithium carbonate (202 mg), the title compound was obtained as pale-yellow oil (yield: 208 mg, yield: 76%).

¹H-NMR(CDCl₃)δ: 0.92-1.08(6H,m), 1.48-1.67(3H,m), 1.65-1.93(2H,m), 2.01-2.23(2H,m), 3.07-3.22(1H,m), 3.31-3.52(2H,m), 6.16-6.26(1H,m), 6.25-6.34(1H,m), 7.34(1H,t, J=8.1 Hz).

IR(KBr):3470,2969,2218,1520 cm⁻¹.

Example 46

4-[(2S,3S)-2,3-diethyl-3-hydroxypyrrolidin-1-yl]-2,6-difluorobenzonitrile

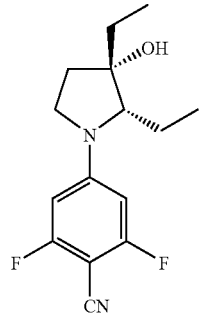

By an operation in the same manner as in Example 1 and using (2S,3S)-2,3-diethylpyrrolidin-3-ol 0.5 oxalate (197 mg), 2,4,6-trifluorobenzonitrile (295 mg) and lithium carbonate (192 mg), the title compound was obtained as a colorless solid (yield: 157 mg, yield: 54%).

¹H-NMR(CDCl₃)δ: 0.92-1.08(6H,m), 1.45-1.76(4H,m), 1.75-1.94(1H,m), 2.02-2.23(2H,m), 3.07-3.22(1H,m), 3.32 (1H,dd,J=7.8,3.6 Hz), 3.36-3.49(1H,m), 6.05(2H,d,J=11.0 Hz).

IR(KBr):3457,2971,2226,1644 cm⁻¹.

mp:66-67° C.

Example 47

4-[(2S,3S)-2,3-diethyl-3-hydroxypyrrolidin-1-yl]-2-(trifluoromethyl)benzonitrile

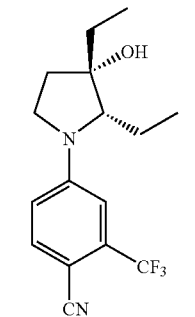

By an operation in the same manner as in Example 1 and using (2S,3S)-2,3-diethylpyrrolidin-3-ol 0.5 oxalate (193 mg), 4-fluoro-2-(trifluoromethyl)benzonitrile (364 mg) and lithium carbonate (221 mg), the title compound was obtained as pale-yellow oil (yield: 219 mg, yield: 82%).

¹H-NMR(CDCl₃)δ: 0.93-1.08(6H,m), 1.47-1.69(3H,m), 1.69-1.97(2H,m), 2.02-2.25(2H,m), 3.13-3.29(1H,m), 3.36-3.57(2H,m), 6.61(1H,dd,J=8.7,2.7 Hz), 6.78(1H,d,J=2.7 Hz), 7.56(1H,d,J=8.7 Hz).

IR(KBr):3457,2969,2218,1615 cm⁻¹.

Example 48

2-chloro-4-[(2S,3S)-2,3-diethyl-3-hydroxypyrrolidin-1-yl]benzonitrile

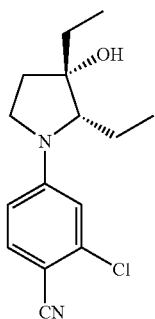

By an operation in the same manner as in Example 1 and using (2S,3S)-2,3-diethylpyrrolidin-3-ol 0.5 oxalate (204 mg), 2-chloro-4-fluorobenzonitrile (314 mg) and lithium carbonate (205 mg), the title compound was obtained as pale-yellow oil (yield: 262 mg, yield: 87%).

$^1$H-NMR(CDCl$_3$)δ: 0.92-1.06(6H,m), 1.47-1.66(3H,m), 1.62-1.75(1H,m), 1.74-1.94(1H,m), 1.99-2.22(2H,m), 3.07-3.24(1H,m), 3.33-3.51(2H,m), 6.39(1H,dd,J=8.8,2.3 Hz), 6.52(1H,d,J=2.3 Hz), 7.40(1H,d,J=8.8 Hz).

IR(KBr):3478,2967,2216,1599 cm$^{-1}$.

Example 49

4-[(2S,3S)-2,3-diethyl-3-hydroxypyrrolidin-1-yl]-2-methoxybenzonitrile

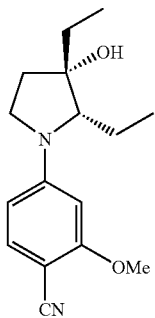

By an operation in the same manner as in Example 1 and using (2S,3S)-2,3-diethylpyrrolidin-3-ol 0.5 oxalate (201 mg), 4-fluoro-2-methoxybenzonitrile (250 mg) and lithium carbonate (180 mg), the title compound was obtained as a colorless solid (yield: 158 mg, yield: 54%).

$^1$H-NMR(CDCl$_3$)δ: 0.93-1.07(6H,m), 1.49-1.69(3H,m), 1.69-1.93(2H,m), 2.01-2.22(2H,m), 3.10-3.25(1H,m), 3.32-3.52(2H,m), 3.88(3H,s), 5.91-5.98(1H,m), 6.10(1H,dd, J=8.7, 2.3 Hz), 7.24-7.36(1H,m).

IR(KBr):3438,2967,2209,1613 cm$^{-1}$.

mp:91-92° C.

Example 50

2-chloro-4-[(2S,3S)-2,3-diethyl-3-hydroxypyrrolidin-1-yl]-3-methylbenzonitrile

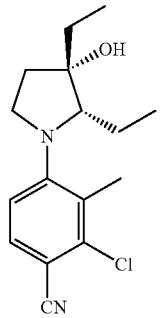

By an operation in the same manner as in Example 1 and using (2S,3S)-2,3-diethylpyrrolidin-3-ol 0.5 oxalate (201 mg), 2-chloro-4-fluoro-3-methylbenzonitrile (294 mg) and lithium carbonate (250 mg), the title compound was obtained as pale-yellow oil (yield: 95.6 mg, yield: 31%).

$^1$H-NMR(CDCl$_3$)δ: 0.93(3H,t,J=7.5 Hz), 1.06(3H,t,J=7.5 Hz), 1.33-1.51(1H,m), 1.54-1.78(3H,m), 1.78-1.99(3H,m), 2.33(3H,s), 2.79-2.92(1H,m), 3.40(1H,dd,J=8.1,3.2 Hz), 3.75-3.91(1H,m), 6.78(1H,d,J=8.7 Hz), 7.39(1H,d,J=8.7 Hz).

IR(KBr):3476,2969,2220,1586 cm$^{-1}$.

Example 51

2-fluoro-4-[(2S,3S)-2,3-diethyl-3-hydroxypyrrolidin-1-yl]-3-methylbenzonitrile

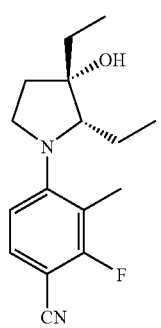

By an operation in the same manner as in Example 1 and using (2S,3S)-2,3-diethylpyrrolidin-3-ol 0.5 oxalate (200 mg), 2,4-difluoro-3-methylbenzonitrile (279 mg) and lithium carbonate (220 mg), the title compound was obtained as pale-yellow oil (yield: 151 mg, yield: 52%).

$^1$H-NMR(CDCl$_3$)δ: 0.94(3H,t,J=7.6 Hz), 1.06(3H,t,J=7.4 Hz), 1.37-1.53(1H,m), 1.54-1.78(3H,m), 1.78-2.00(3H,m), 2.18(3H,d,J=2.4 Hz), 2.92-3.06(1H,m), 3.46(1H,dd,J=8.3, 2.2 Hz), 3.79-3.95(1H,m), 6.59(1H,d,J=8.7 Hz), 7.23-7.35 (1H,m)

IR(KBr):3478,2969,2224,1613 cm$^{-1}$..

Example 52

4-[(2S,3R)-3-cyclopropyl-2-ethyl-3-hydroxypyrrolidin-1-yl]-2-methoxybenzonitrile

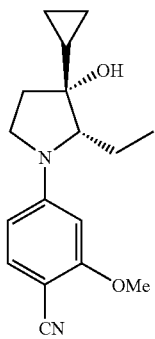

By an operation in the same manner as in Example 1 and using (2S,3R)-3-cyclopropyl-2-ethylpyrrolidin-3-ol 0.5 oxalate (185 mg), 4-fluoro-2-methoxybenzonitrile (290 mg) and lithium carbonate (198 mg), the title compound was obtained as a pale-yellow solid (yield: 144 mg, yield: 55%).

$^1$H-NMR(CDCl$_3$)δ: 0.27-0.52(4H,m), 0.95-1.13(1H,m), 1.00(3H,t,J=7.4 Hz), 1.32-1.38(1H,m), 1.48-1.66(1H,m), 1.72-1.89(1H,m), 2.00-2.13(1H,m), 2.14-2.29(1H,m), 3.19-3.34(2H,m), 3.43-3.54(1H,m), 3.89(3H,s), 5.95(1H,d,J=2.3 Hz), 6.10(1H,dd,J=8.7,2.3 Hz), 7.33(1H,d,J=8.7 Hz).

IR(KBr):3461,2965,2211,1609 cm$^{-1}$.

mp:140-141° C.

Example 53 rac-4-[(2R,3S)-3-hydroxy-2,4,4-trimethylpyrrolidin-1-yl]-2-methoxybenzonitrile

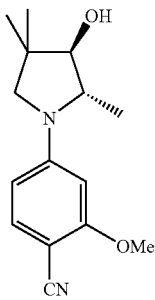

A suspension (5 mL) of (2R,3S)-2,4,4-trimethylpyrrolidin-3-ol 0.5 oxalate (152 mg), 4-fluoro-2-methoxybenzonitrile (183 mg) and lithium carbonate (155 mg) in DMSO was stirred at 100° C. for 15 hr, added to water, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=50/1→2/3) to give the title compound as a colorless solid (yield: 103 mg, yield: 45%).

$^1$H-NMR(CDCl$_3$)δ: 0.99(3H,s), 1.17(3H,s), 1.39(3H,d,J=6.0 Hz), 1.70(1H,d,J=6.0 Hz), 3.17-3.33(2H,m), 3.54-3.72 (2H,m), 3.88(3H,s), 5.96(1H,d,J=7.2 Hz), 6.11(1H,dd,J=8.7, 2.1 Hz), 7.32(1H,d,J=8.7 Hz).

IR(KBr):3418,2963,2211,1609 cm$^{-1}$.

mp:139-142° C.

Example 54 rac-4-[(2R,3S)-3-hydroxy-2,4,4-trimethylpyrrolidin-1-yl]-2-(trifluoromethyl)benzonitrile

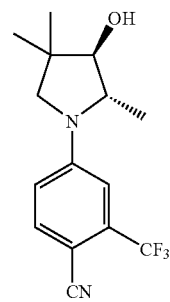

By an operation in the same manner as in Example 53 and using (2R,3S)-2,4,4-trimethylpyrrolidin-3-ol 0.5 oxalate (146 mg), 4-fluoro-2-(trifluoromethyl)benzonitrile (255 mg) and lithium carbonate (140 mg), the title compound was obtained as a colorless solid (yield: 106 mg, yield: 42%).

$^1$H-NMR(CDCl$_3$)δ: 0.99(3H,s), 1.19(3H,s), 1.40(3H,d, J=6.0 Hz), 1.81(1H,d,J=5.7 Hz), 3.19-3.38(2H,m), 3.57-3.76 (2H,m), 6.63(1H,dd,J=8.5,2.4 Hz), 6.79(1H,d,J=2.4 Hz), 7.57(1H,d,J=8.5 Hz).

IR(KBr):3430,2967,2220,1613 cm$^{-1}$.

mp:115-116° C.

Example 55 rac-2-fluoro-4-[(2R,3S)-3-hydroxy-2,4,4-trimethylpyrrolidin-1-yl]-3-methylbenzonitrile

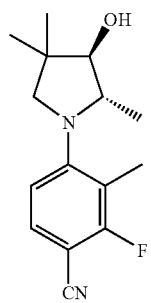

By an operation in the same manner as in Example 53 and using (2RS,3SR)-2,4,4-trimethylpyrrolidin-3-ol 0.5 oxalate (214 mg), 2,4-difluoro-3-methylbenzonitrile (240 mg) and lithium carbonate (246 mg), the title compound was obtained as a colorless solid (yield: 112 mg, yield: 35%).

$^1$H-NMR(CDCl$_3$)δ: 0.95(3H,s), 1.13(3H,s), 1.18(3H,d, J=5.7 Hz), 1.68(1H,d,J=6.1 Hz), 2.13(3H,d,J=2.3 Hz), 2.91 (1H,d,J=9.5 Hz), 3.51(1H,d,J=9.5 Hz), 3.55-3.71(2H,m), 6.54(1H,d,J=8.3 Hz), 7.23-7.33(1H,m).

IR(KBr):3428,2967,2224,1613 cm$^{-1}$.

mp:118-119° C.

Example 56

4-[(2S,3S,5R)-3-hydroxy-2,5-dimethylpyrrolidin-1-yl]-2-methoxybenzonitrile

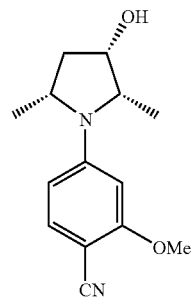

By an operation in the same manner as in Example 53 and using (2S,3S,5R)-2,5-dimethylpyrrolidin-3-ol 0.5 oxalate (62 mg), 4-fluoro-2-methoxybenzonitrile (70 mg) and lithium carbonate (63 mg), the title compound was obtained as a colorless solid (yield: 7 mg, yield: 7.3%).

$^1$H-NMR(CDCl$_3$)δ: 1.28(3H,d,J=6.4 Hz), 1.37(3H,d, J=6.1 Hz), 1.75-1.90(1H,m), 1.95-2.05(1H,m), 2.43-2.57 (1H,m), 3.77-3.96(2H,m), 3.87(3H,s), 4.38(1H,q,J=7.4 Hz), 6.00-6.05(1H,m), 6.17(1H,dd,J=8.7,1.9 Hz), 7.31(1H,d, J=8.7 Hz).

IR(KBr):3426,2973,2211,1609 cm$^{-1}$.

Example 57

2-chloro-4-[(2S,3S,5R)-3-hydroxy-2,5-dimethylpyrrolidin-1-yl]benzonitrile

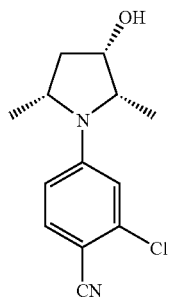

By an operation in the same manner as in Example 53 and using (2S,3S,5R)-2,5-dimethylpyrrolidin-3-ol 0.5 oxalate (144 mg), 2-chloro-4-fluorobenzonitrile (254 mg) and lithium carbonate (193 mg), the title compound was obtained as colorless oil (yield: 61 mg, yield: 27%).

$^1$H-NMR(CDCl$_3$)δ: 1.27(3H,d,J=6.4 Hz), 1.36(3H,d, J=6.4 Hz), 1.61-1.71(1H,m), 1.75-1.91(1H,m), 2.43-2.59 (1H,m), 3.74-3.93(2H,m), 4.32-4.45(1H,m), 6.46(1H,dd, J=8.8,2.4 Hz), 6.59(1H,d,J=2.4 Hz), 7.41(1H,d,J=8.8 Hz).

IR(KBr):3401,2218,1599 cm$^{-1}$.

Example 58

4-[(2S,3S,5R)-3-hydroxy-2,5-dimethylpyrrolidin-1-yl]-2-(trifluoromethyl)benzonitrile

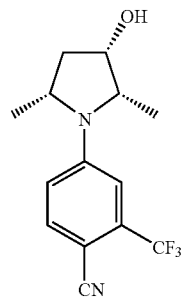

By an operation in the same manner as in Example 53 and using (2S,3S,5R)-2,5-dimethylpyrrolidin-3-ol 0.5 oxalate (153 mg), 4-fluoro-2-(trifluoromethyl)benzonitrile (277 mg) and lithium carbonate (200 mg), the title compound was obtained as colorless oil (yield: 121 mg, yield: 45%).

$^1$H-NMR(CDCl$_3$)δ: 1.30(3H,d,J=6.4 Hz), 1.38(3H,d, J=6.4 Hz), 1.65-1.73(1H,m), 1.77-1.94(1H,m), 2.43-2.61 (1H,m), 3.80-3.98(2H,m), 4.33-4.49(1H,m), 6.68(1H,dd, J=8.8,2.5 Hz), 6.84(1H,d,J=2.5 Hz), 7.57(1H,d,J=8.8 Hz).

IR(KBr):3407,2220,1611 cm$^{-1}$.

Example 59

2-fluoro-4-[(2S,3S,5R)-3-hydroxy-2,5-dimethylpyrrolidin-1-yl]-3-methylbenzonitrile

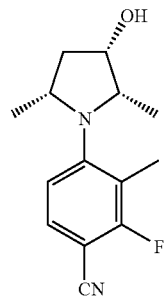

By an operation in the same manner as in Example 53 and using (2S,3S,5R)-2,5-dimethylpyrrolidin-3-ol 0.5 oxalate (189 mg), 2,4-difluoro-3-methylbenzonitrile (510 mg) and lithium carbonate (200 mg), the title compound was obtained as colorless oil (yield: 20 mg, yield: 6.8%).

$^1$H-NMR(CDCl$_3$)δ: 0.92(3H,d,J=6.4 Hz), 1.00(3H,d, J=6.1 Hz), 1.50-1.68(2H,m), 1.72-1.85(1H,m), 2.25-2.36 (3H,m), 3.02-3.21(2H,m), 4.15(1H,brs), 7.05-7.16(1H,m), 7.40(1H,t,J=8.0 Hz).

IR(KBr):3382,2222,1615 cm$^{-1}$.

Example 60

2-chloro-4-[(2S,3S,5R)-3-hydroxy-2,3,5-trimethylpyrrolidin-1-yl]benzonitrile

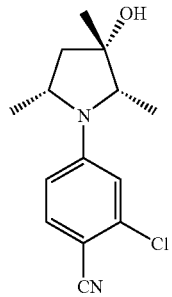

By an operation in the same manner as in Reference Example 51 and using benzyl (2S,3S,5R)-3-hydroxy-2,3,5-trimethylpyrrolidine-1-carboxylate (450 mg), 10% palladium carbon (50% water-containing, 40 mg) and oxalic acid (77 mg), (2S,3S,5R)-2,3,5-trimethylpyrrolidin-3-ol 0.5 oxalate was obtained as a colorless solid (yield: 285.3 mg, yield: 96%). By an operation in the same manner as in Reference Example 53 and using (2S,3S,5R)-2,3,5-trimethylpyrrolidin-3-ol 0.5 oxalate (50 mg), 2-chloro-4-fluorobenzonitrile (67 mg) and lithium carbonate (46.7 mg), the title compound was obtained as a colorless solid (yield: 36.3 mg, yield: 48%).

$^1$H-NMR(CDCl$_3$)δ: 1.29(3H,d,J=6.2 Hz), 1.30(3H,s), 1.35(3H,d,J=6.0 Hz), 1.49-1.54(1H,m), 1.95(1H,dd,J=12.6, 7.6 Hz), 2.22(1H,dd,J=12.6,6.6 Hz), 3.48(1H,q,J=6.6 Hz), 3.66-3.82(1H,m), 6.46(1H,dd,J=8.8,2.5 Hz), 6.59(1H,d, J=2.5 Hz), 7.36-7.47(1H,m).

mp:132-133° C.

Example 61

2-fluoro-4-[(2S,3S,5R)-3-hydroxy-2,3,5-trimethylpyrrolidin-1-yl]benzonitrile

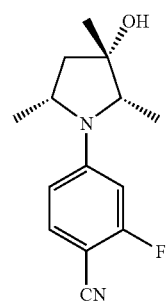

By an operation in the same manner as in Example 53 and using (2S,3S,5R)-2,3,5-trimethylpyrrolidin-3-ol 0.5 oxalate (93 mg), 2,4-difluorobenzonitrile (120 mg) and lithium carbonate (93 mg), the title compound was obtained as a colorless solid (yield: 76 mg, yield: 57%).

$^1$H-NMR(CDCl$_3$)δ: 1.29(3H,d,J=6.6 Hz), 1.30(3H,s), 1.35(3H,d,J=6.2 Hz), 1.54-1.64(1H,m), 1.96(1H,dd,J=12.6, 7.6 Hz), 2.22(1H,dd,J=12.6,7.6 Hz), 3.47(1H,q,J=6.6 Hz), 3.65-3.81(1H,m), 6.28(1H,dd,J=13.0,2.3 Hz), 6.35(1H,dd, J=8.8,2.3 Hz), 7.35(1H,dd,J=8.8,7.7 Hz).

mp:125-128° C.

Example 62

4-[(2S,3S,5R)-3-hydroxy-2,3,5-trimethylpyrrolidin-1-yl]-2-(trifluoromethyl)benzonitrile

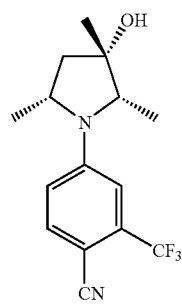

By an operation in the same manner as in Example 53 and using (2S,3S,5R)-2,3,5-trimethylpyrrolidin-3-ol 0.5 oxalate (83 mg), 4-fluoro-2-(trifluoromethyl)benzonitrile (203 mg) and lithium carbonate (93 mg), the title compound was obtained as a colorless solid (yield: 61.9 mg, yield: 44%).

$^1$H-NMR(CDCl$_3$)δ: 1.31(3H,d,J=6.6 Hz), 1.32(3H,s), 1.37(3H,d,J=6.2 Hz), 1.48-1.53(1H,m), 1.98(1H,dd,J=12.6, 7.7 Hz), 2.24(1H,dd,J=12.6,7.7 Hz), 3.46-3.58(1H,m), 3.73-3.89(1H,m), 6.67(1H,dd,J=8.9,2.5 Hz), 6.83(1H,d,J=2.5 Hz), 7.58(1H,d,J=8.9 Hz).

mp:115-117° C.

Example 63

4-[(2S,3S,5R)-3-hydroxy-2,3,5-trimethylpyrrolidin-1-yl]-2-methoxybenzonitrile

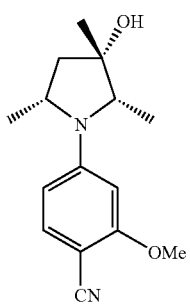

To a solution (5 mL) of 2-fluoro-4-[(2S,3S,5R)-3-hydroxy-2,3,5-trimethylpyrrolidin-1-yl]benzonitrile (47.6 mg) in DMSO was added sodium methoxide (35 mg) and the mixture was stirred at 100° C. for 3.5 hr. Sodium methoxide (130 mg) was added, and the mixture was stirred at 100° C. for 4.5 hr. The reaction mixture was added to water, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=50/1→2/3) to give the title compound as a colorless solid (yield: 25.1 mg, yield: 50%).

$^1$H-NMR(CDCl$_3$)δ: 1.30(3H,d,J=6.6 Hz), 1.31(3H,s), 1.36(3H,d,J=6.0 Hz), 1.48-1.60(1H,m), 1.95(1H,dd,J=12.5, 7.6 Hz), 2.21(1H,dd,J=12.5,7.6 Hz), 3.51(1H,q,J=6.6 Hz), 3.69-3.84(1H,m), 3.88(3H,s), 6.02(1H,d,J=2.2 Hz), 6.16(1H,dd,J=8.7,2.2 Hz), 7.32(1H,d,J=8.7 Hz).

mp:121-123° C.

Experimental Example 1

AR Binding Inhibitory Test (Wild-Type)

To a solution containing a wild-type androgen receptor (AR) was added 3 nM radiolabeled mibolerone and 100 nM compound. After the solution was incubated at 4° C. for 3 hr, B (Bound)/F (Free) separation was performed by the dextran/charcoal method. The label count of B was measured, and the inhibitory rate of the compound was calculated. The results are shown in Table 1.

TABLE 1

| Example compound No. | Inhibitory rate (%) at 100 nM |
|---|---|
| 1 | 95 |
| 7 | 98 |
| 18 | 100 |
| 20 | 98 |
| 32 | 98 |
| 60 | 92 |

Experimental Example 2

Evaluation of the Compound in Reporter Assay System to be Used Cos7 cell

Cos-7(5,000,000 cells) were sown in a flask (150 cm$^2$), and cultured in a culture medium (DMEM medium containing 10% Dextran Charcoal (DCC)-Fetal Bovine Serum (FBS) and 2 mM glutamine) for 24 hr. A vector DNA containing AR gene, and a vector DNA prepared by binging luciferase gene at the downstream of an androgen responsive promoter derived from MMTV (Mouse Mammary Tumor Virus) were co-transfected by the liposome method. After culture for 4 hr, the cells were harvested, 10,000 cells were plated on a 96 well plate and cultured for 2 hr, after which 1 μM of 5α-dihydrotestosterone or 100 nM of a compound was added thereto. After culture for 24 hr, luciferase activity was determined. The induction rate by the compound was determined with the luciferase activity induced by addition of 1 μM of 5α-dihydrotestosterone as 100. The results are shown in Table 2.

TABLE 2

| Example Compound No. | Induction rate (%) at 100 nM |
|---|---|
| 1 | 65 |
| 7 | 107 |
| 18 | 89 |
| 20 | 59 |
| 32 | 77 |
| 60 | 37 |

Formulation Example 1

Injection Containing Compound Described in Example 1

| (1) compound described in Example 1 | 5.0 mg |
| (2) sodium chloride | 20.0 mg |
| (3) distilled water | amount to make total amount 2 ml |

The compound (5.0 mg) described in Example 1 and sodium chloride (20.0 mg) are dissolved in distilled water, and water is added to the total amount of 2.0 ml. The solution is filtrated, and aseptically filled in a 2 ml ampoule. The ampoule is sterilized and tightly sealed to give a solution for injection.

INDUSTRIAL APPLICABILITY

The compound of the present invention has a superior action as an androgen receptor modulator (particularly agonist), and is useful for the prophylaxis or treatment of hypogonadism, male climacteric disorder, frailty, cachexia, osteoporosis and the like, for which administration of androgen is effective.

This application is based on application Nos. 2006-324538 and 2007-205966 filed in Japan, the contents of which are incorporated hereinto by reference.

The invention claimed is:

1. A compound represented by the formula (I)

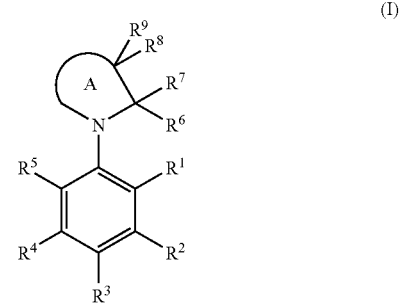

wherein
R$^1$ is a hydrogen atom or alkyl optionally having substituent(s);
R$^2$ is a hydrogen atom, a halogen atom, alkyl optionally having substituent(s) or alkoxy optionally having substituent(s);
R$^3$ is cyano;
R$^4$ is a hydrogen atom or a halogen atom;
R$^5$ is a hydrogen atom;
R$^6$ is a hydrogen atom;
R$^7$ is alkyl optionally having substituent(s);
R$^8$ is a hydrogen atom, alkyl optionally having substituent(s), alkenyl optionally having substituent(s) or cycloalkyl optionally having substituent(s);
R$^9$ is hydroxy; and
ring A is a 5- or 6-membered ring optionally having substituent(s) other than R$^6$ to R$^9$ (except 2-chloro-4-[(2S, 3S)-3-hydroxy-2-methylpyrrolidin-1-yl]-3-methylbenzonitrile, 2-chloro-4-[(2S,3S)-3-hydroxy-2- methylpyrrolidin-1-yl]benzonitrile, 4-[(2S,3S)-3-hydroxy-2-methylpyrrolidin-1-yl]benzonitrile, 2-chloro-4-[(2S,3S)-3-hydroxy-2-methylpyrrolidin-1-yl]-5-methylbenzonitrile, 2-chloro-3-ethyl-4-[(2S,3S)-3-hydroxy-2-methylpyrrolidin-1-yl]benzonitrile, 4-[(2S,3S)-3-hydroxy-2-methylpyrrolidin-1-yl]-2-(trifluoromethyl)benzonitrile, 4-[(2S,3S)-3-hydroxy-2-methylpyrrolidin-1-yl]-3-(trifluoromethyl)benzonitrile, 4-[(2S,3S)-3-hydroxy-2-isopropylpyrrolidin-1-yl]-2-(trifluoromethyl)benzonitrile, 4-[(2S,3R)-3-hydroxy-2-isopropylpyrrolidin-1-yl]-2-(trifluoromethyl)benzonitrile, and 2-chloro-4-[(2S)-3-hydroxy-2-methylpiperidin-1-yl]benzonitrile), or a salt thereof.

2. The compound of claim 1 or a salt thereof, wherein ring A is a 5-membered ring optionally having $C_{1-6}$ alkyl(s) other than $R^6$ to $R^9$.

3. The compound of claim 1, wherein $R^1$ is (i) a hydrogen atom or (ii) $C_{1-6}$ alkyl optionally having halogen atom(s);
$R^2$ is a hydrogen atom, a halogen atom, $C_{1-6}$ alkyl optionally having halogen atom(s) or $C_{1-6}$ alkoxy;
$R^7$ is $C_{1-6}$ alkyl;
$R^8$ is a hydrogen atom, $C_{1-6}$ alkyl optionally having halogen atom(s), $C_{2-6}$ alkenyl or $C_{3-8}$ cycloalkyl; and
ring A is a pyrrolidine ring optionally having 1 or 2 $C_{1-6}$ alkyl(s) other than $R^6$ to $R^9$.

4. A compound below or a salt thereof:
2-fluoro-4-[(2S,3S)-3-hydroxy-2,3-dimethylpyrrolidin-1-yl]benzonitrile, 2-fluoro-4-[(2S,3S)-3-hydroxy-2,3-dimethylpyrrolidin-1-yl]-3-methylbenzonitrile, 4-[(2S,3S)-3-ethyl-3-hydroxy-2-methylpyrrolidin-1-yl]-2,6-difluorobenzonitrile, 2-chloro-4-[(2S,3S)-3-hydroxy-2-methyl-3-(trifluoromethyl)pyrrolidin-1-yl]benzonitrile, 2,6-difluoro-4-[(2S,3S)-3-hydroxy-2-isopropyl-3-methylpyrrolidin-1-yl]benzonitrile, or 4-[(2S,3R)-3-cyclopropyl-3-hydroxy-2-methylpyrrolidin-1-yl]-2-fluorobenzonitrile.

5. A composition comprising the compound of claim 1, or a salt thereof.

6. The composition of claim 5, which is an agent for the treatment of hypogonadism, male climacteric disorder, frailty, cachexia or osteoporosis.

7. The composition of claim 5, which is a frailty suppressive agent, a muscle enhancing agent, a muscle increasing agent, a cachexia suppressive agent, a body weight decrease suppressive agent, an agent for the treatment of prostatomegaly, muscular atrophy disorder or muscle decrease caused by a disease, or a prostate weight decreasing agent.

8. A method for the treatment of hypogonadism, male climacteric disorder, frailty, cachexia or osteoporosis, comprising administering, to a mammal, an effective amount of the compound of claim 1, or a salt thereof.

* * * * *